US010399959B2

(12) United States Patent
Takeuchi et al.

(10) Patent No.: US 10,399,959 B2
(45) Date of Patent: *Sep. 3, 2019

(54) ACID-ADDITION SALT OF TRK-INHIBITING COMPOUND

(71) Applicant: ONO PHARMACEUTICAL CO., LTD., Osaka-shi, Osaka (JP)

(72) Inventors: Jun Takeuchi, Osaka (JP); Satoshi Itadani, Osaka (JP); Masahiro Ikura, Osaka (JP); Masato Higashino, Osaka (JP); Hideomi Kijima, Osaka (JP); Shizuka Ono, Osaka (JP); Tetsuya Yasuhiro, Osaka (JP); Takeshi Nagaura, Osaka (JP)

(73) Assignee: ONO PHARMACEUTICAL CO., LTD., Osaka-Shi, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/504,514

(22) PCT Filed: Aug. 17, 2015

(86) PCT No.: PCT/JP2015/072990
§ 371 (c)(1),
(2) Date: Feb. 16, 2017

(87) PCT Pub. No.: WO2016/027754
PCT Pub. Date: Feb. 25, 2016

(65) Prior Publication Data
US 2017/0240527 A1 Aug. 24, 2017

(30) Foreign Application Priority Data

Aug. 18, 2014 (JP) ................................ 2014-165622

(51) Int. Cl.
| | | |
|---|---|---|
| *C07D 401/12* | (2006.01) |
| *C07D 401/14* | (2006.01) |
| *A61K 45/00* | (2006.01) |
| *A61K 31/506* | (2006.01) |
| *C07C 309/04* | (2006.01) |
| *A61K 45/06* | (2006.01) |
| *C07C 309/29* | (2006.01) |
| *C07C 309/30* | (2006.01) |

(52) U.S. Cl.
CPC .......... *C07D 401/12* (2013.01); *A61K 31/506* (2013.01); *A61K 45/00* (2013.01); *A61K 45/06* (2013.01); *C07C 309/04* (2013.01); *C07C 309/29* (2013.01); *C07C 309/30* (2013.01); *C07D 401/14* (2013.01); *C07B 2200/13* (2013.01)

(58) Field of Classification Search
CPC .................................................. C07D 401/12
See application file for complete search history.

(56) References Cited

U.S. PATENT DOCUMENTS

| 9,463,192 B2 | 10/2016 | Takeuchi et al. |
| 9,498,453 B2 | 11/2016 | Takeuchi et al. |
| 9,763,943 B2 | 9/2017 | Takeuchi et al. |
| 9,993,479 B2 | 6/2018 | Takeuchi et al. |
| 2016/0000783 A1 | 1/2016 | Takeuchi et al. |
| 2016/0280684 A1 | 9/2016 | Takeuchi et al. |
| 2017/0027939 A1 | 2/2017 | Takeuchi et al. |
| 2017/0340634 A1 | 11/2017 | Takeuchi et al. |
| 2018/0256573 A1 | 9/2018 | Takeuchi et al. |

FOREIGN PATENT DOCUMENTS

| CN | 102596957 A | 7/2012 |
| EP | 2 960 234 A1 | 12/2015 |
| RU | 2667907 C2 | 9/2018 |
| WO | WO-03/068228 A1 | 8/2003 |
| WO | WO-2011/006074 A1 | 1/2011 |
| WO | WO-2013/161919 A1 | 12/2015 |

OTHER PUBLICATIONS

Botchkarev et al, Neurotrophins in Skin Biology and Pathology, Journal of Investigative Dermatology, 2006, p. 1719-1727, vol. 126.
Di Mola et al, Nerve growth factor and Trk high affinity receptor(TrkA) gene expression in inflammatory bowel disease, Gut, 2000, p. 670-678, vol. 46.
Evans et al, Proof of Concept Trial of Tanezumab for the Treatment of Symptoms Associated with Interstital Cystitis, Journal of Urology, 2011, p. 1716-1721, vol. 185.
Ghilardi et al, Administration of a tropomyosin receptor kinase inhibitor attenuates sarcoma-induced nerve sprouting, neuroma formation and bone cancer pain. Molecular Pain, 2010, p. 87, vol. 6.
Ghilardi et al, Sustained blockade of neurotrophin receptors TrkA, TrkB and TrkC reduces non-malignant skeletal pain but not the maintenance of sensory and sympathetic nerve fibers, Bone, 2011, p. 389-398, vol. 48.
Hefit et al, Novel class of pain drugs based on antagonism of NGF, Trends in Pharmacological Sciences, Feb. 2006, p. 85-91, vol. 27.
Huang et al, Trk Receptors: Roles in Neuronal Signal Transduction, Annual Review of Biochemistry, Mar. 2003, p. 609-642, vol. 72.
Katz et al, Efficacy and safety of tanezumab in the treatment of lower back pain, PAIN, 2011, p. 2248-2258, vol. 152.

(Continued)

*Primary Examiner* — Yong S. Chong
(74) *Attorney, Agent, or Firm* — Foley & Lardner LLP

(57) ABSTRACT

In order to provide a prophylactic and/or therapeutic agent for Trk-related diseases, the present invention provides a compound which has a selective Trk-inhibiting activity and persistently inhibits NGF vascular hyper permeability and does not have a drug interaction and in addition thereto, is excellent in solubility and absorbability against free bases. The compound of the present invention has a selective Trk-inhibiting activity and persistently inhibits NGF vascular hyper permeability and does not have a drug interaction and is excellent in solubility and absorbability against free bases, and is therefore useful as a prophylactic and/or therapeutic agent for Trk-related diseases.

13 Claims, 9 Drawing Sheets

(56) References Cited

OTHER PUBLICATIONS

Lane et al, Tanezumab for the Treatment of Pain from Osteoarthritis of the Knee, The New England Journal of Medicine, 2010, p. 1521-1531, vol. 363.
Raap et al, The role of neurotrophins in the pathophysiology of allergic rhinitis, Current Opinion in Allergy and Clinical Immunology, 2010, p. 8-13, vol. 10.
Scuri et al, The Role of Neurotrophins in Inflammation and Allergy, Inflammation and Allergy Drug Targets, 2010, p. 173-180, vol. 9.
Shelton et al, Nerve growth factor mediates hyperalgesia and cachexia in auto-immune arthiritis, PAIN, 2005, p. 8-16, vol. 116.
Vaisnavi et al, Oncogenic and drug-sensitive NTRK1 rearrangements in lung cancer, Nature Medicine, 2013, p. 1469-1472, vol. 19.
Wang et al, Trk kinase inhibitors as new treatments for cancer and pain, Expert Opinions on Therapeutic Patents, 2009, p. 305-319, vol. 19.
Wild et al, Antibodies to Nerve Growth Factor Reverse Established Tactile Allodynia in Rodent Models of Neuropathic Pain without Tolerance, Journal of Pharmacological and Experimental Therapeutics, 2007, p. 282-287, vol. 322.
Zhu et al, Nerve Growth Factor Modulates TRPV1 Expression and Function and Mediates Pain in Chronic Pancreatitis, Gastroenterology, 2011, p. 370-377, vol. 141.
Extended European Search Report dated Feb. 1, 2018 in corresponding application No. 15832999.5.
Chinese Office Action dated Jul. 10, 2018 in corresponding application No. 201580044302.1.
Berge et al, Pharmaceutical Salts, Pharmaceutical Sciences, 1977, vol. 66, pp. 1-19.
Morissette et al, High-throughput crystallization: polymorphs, salts, co-crystals and solvates of pharmaceutical solids, Advanced Drug Delivery Reviews, 2004, vol. 56, pp. 275-300.
Russian Office Action and Search Report dated Mar. 6, 2019 in corresponding application No. 2017104918.

[FIG. 1]
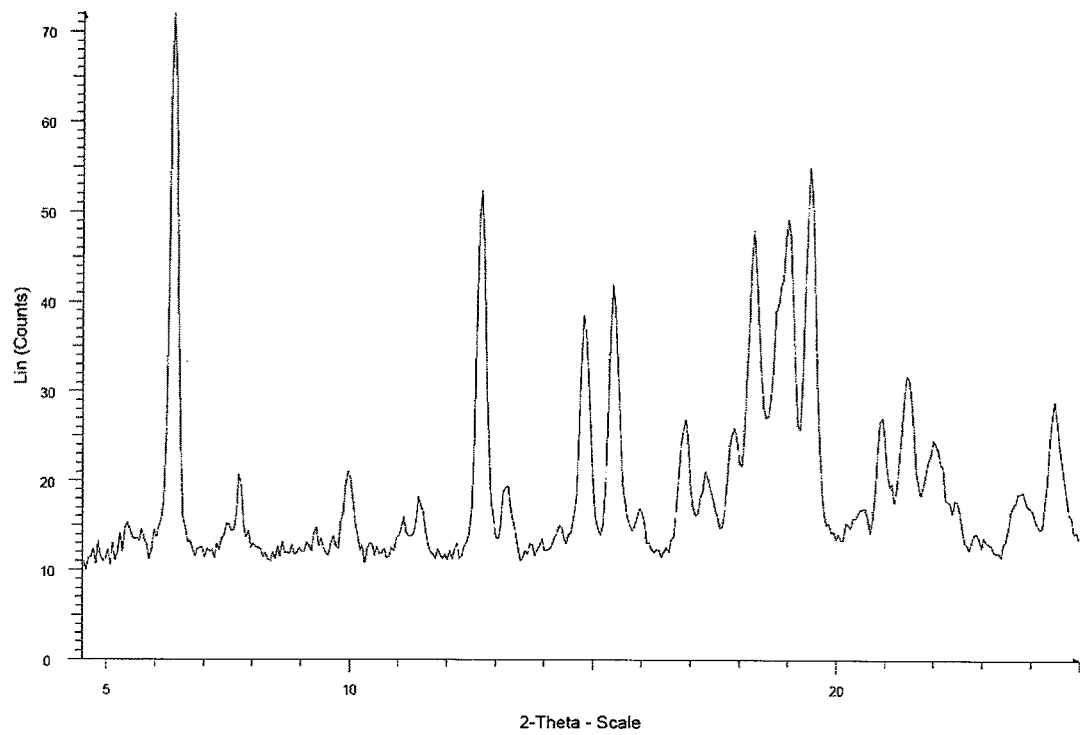
[FIG. 2]
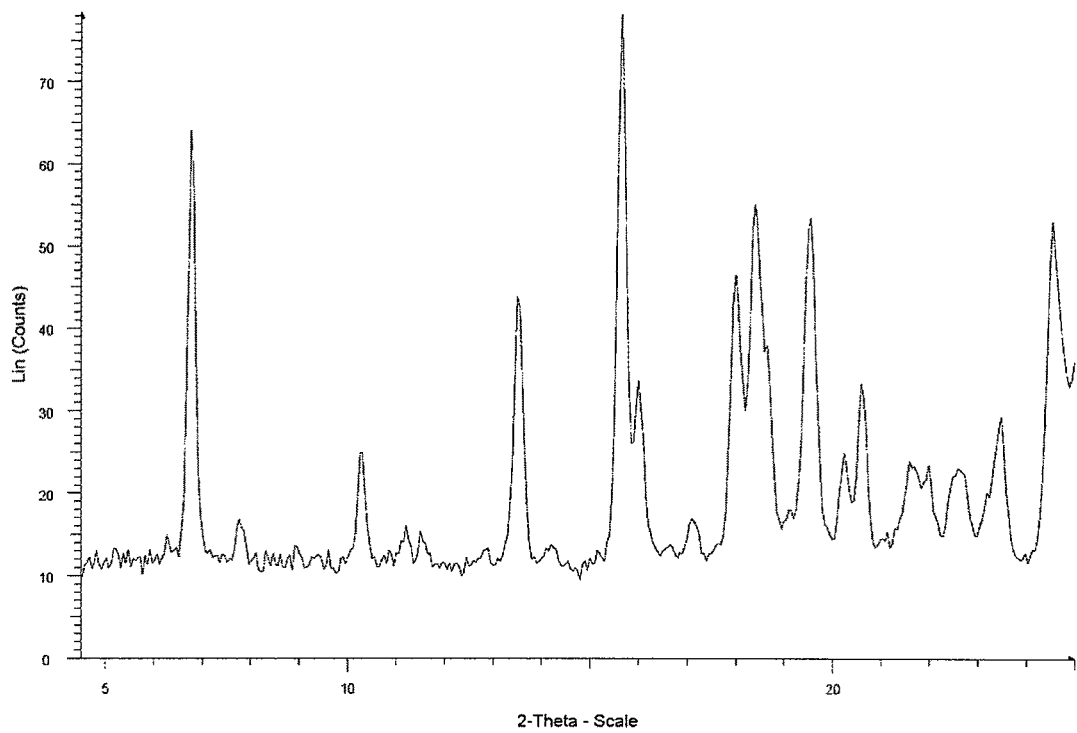

[FIG. 3]
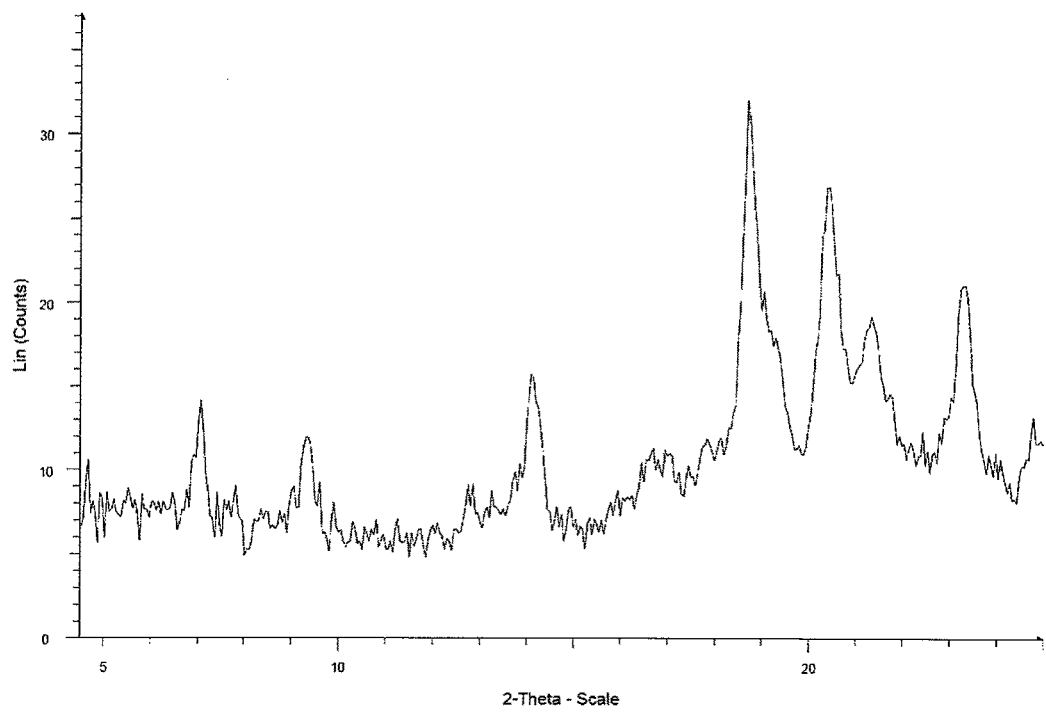
[FIG. 4]
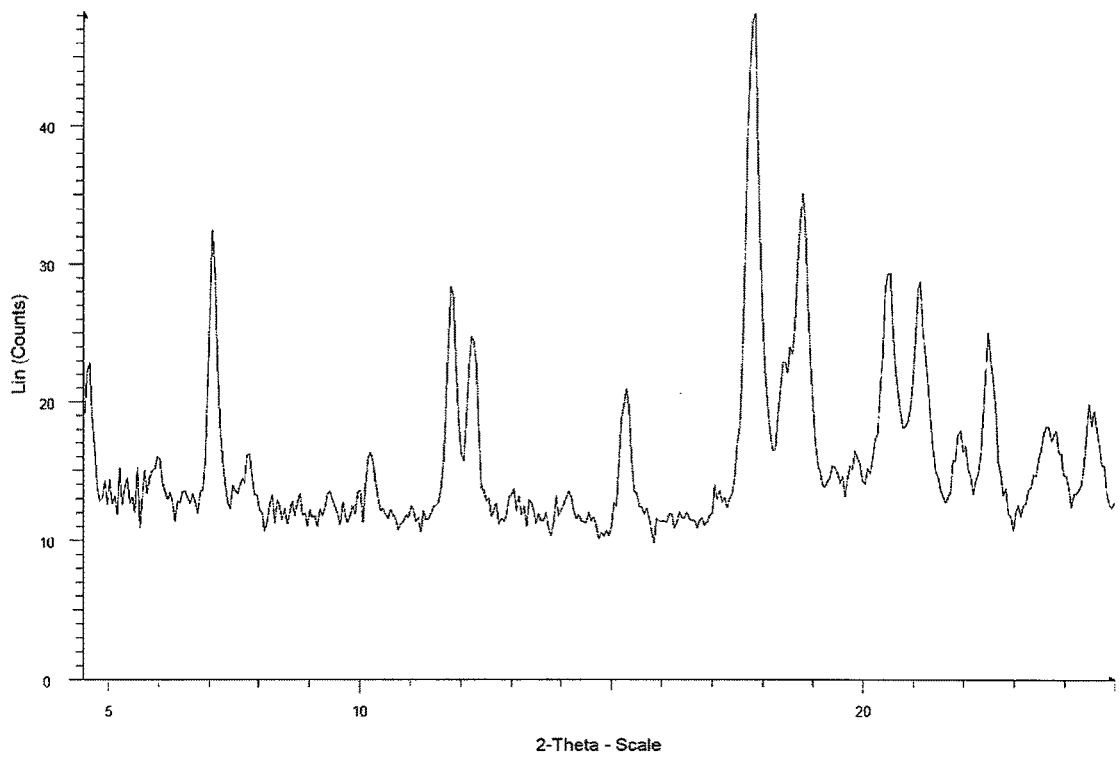

[FIG. 5]
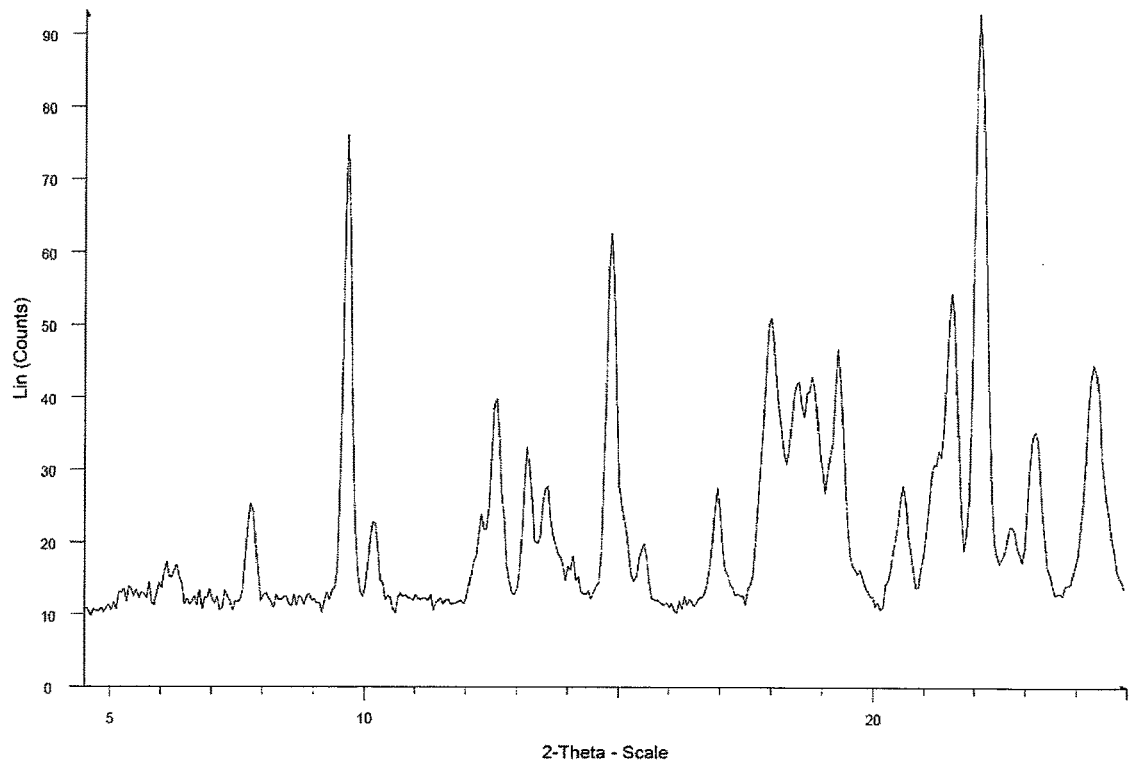
[FIG. 6]
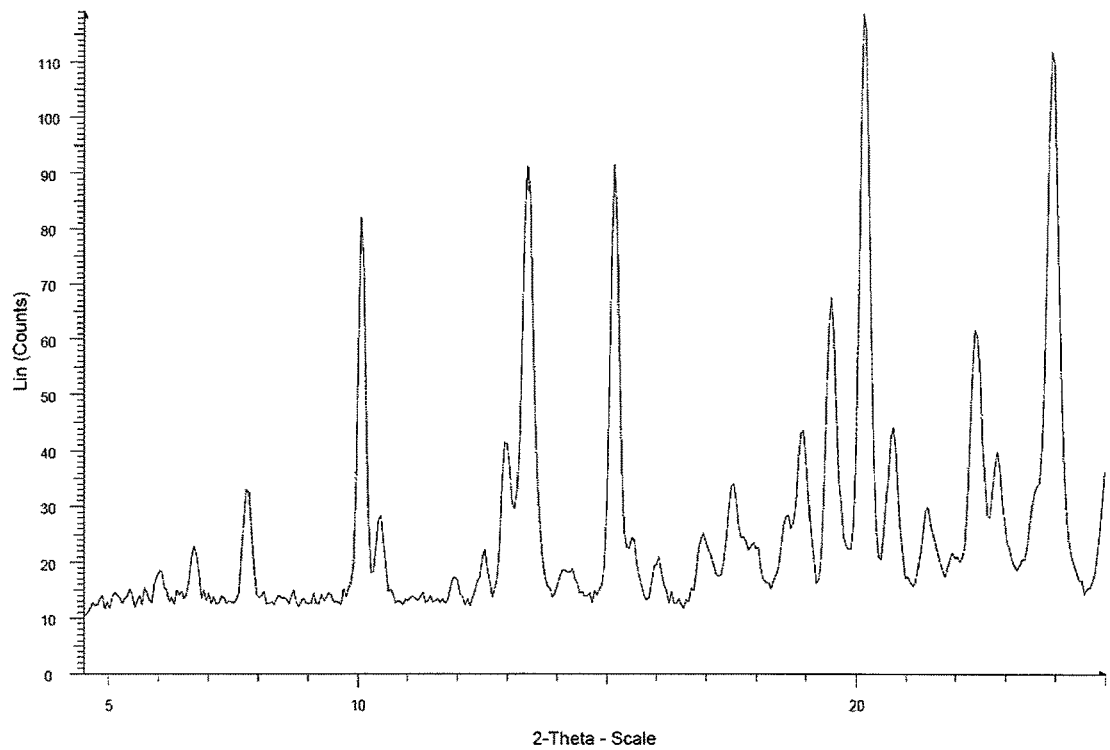

[FIG. 7]
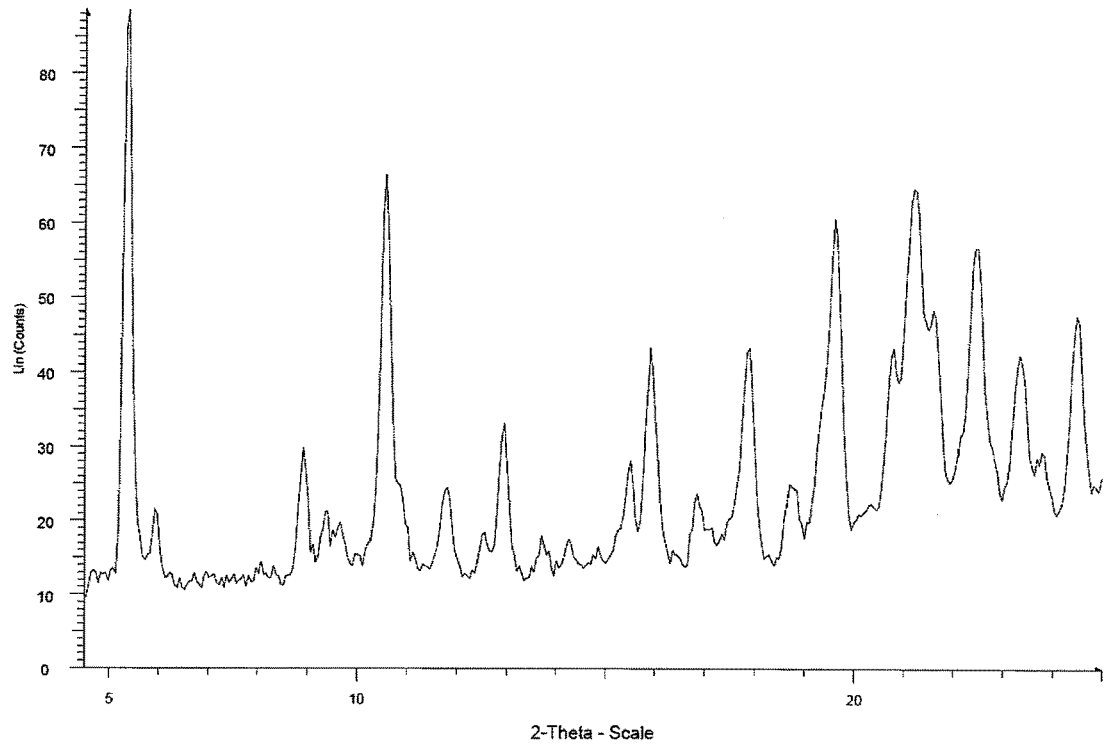
[FIG. 8]
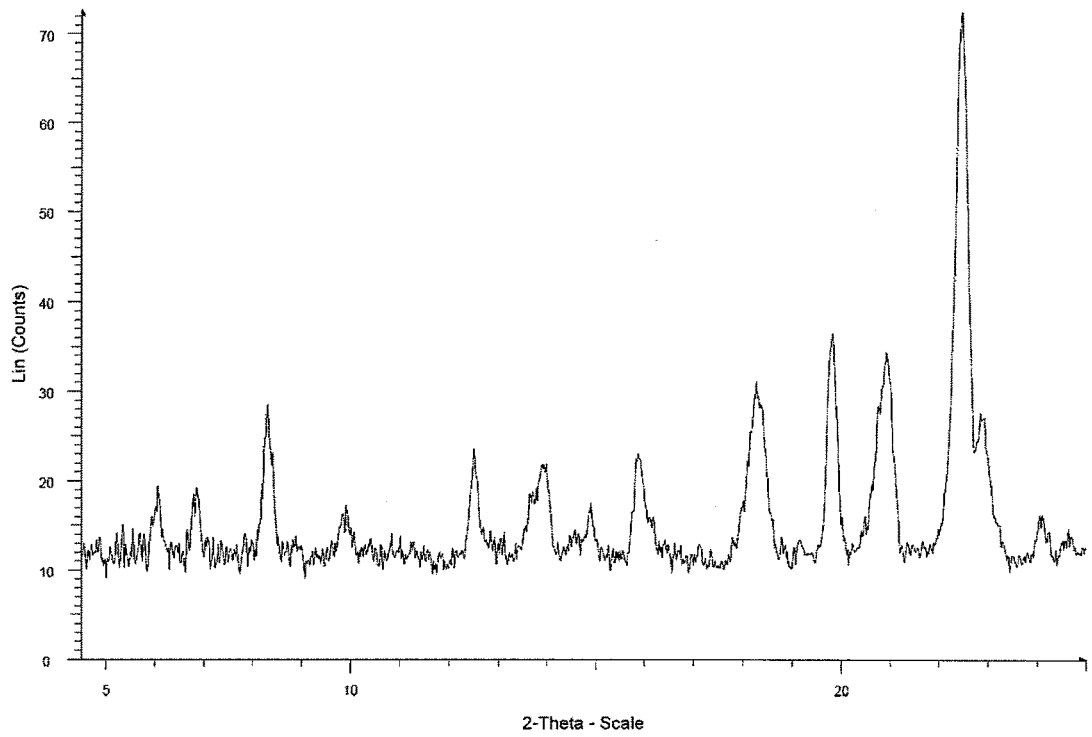

[FIG. 9]
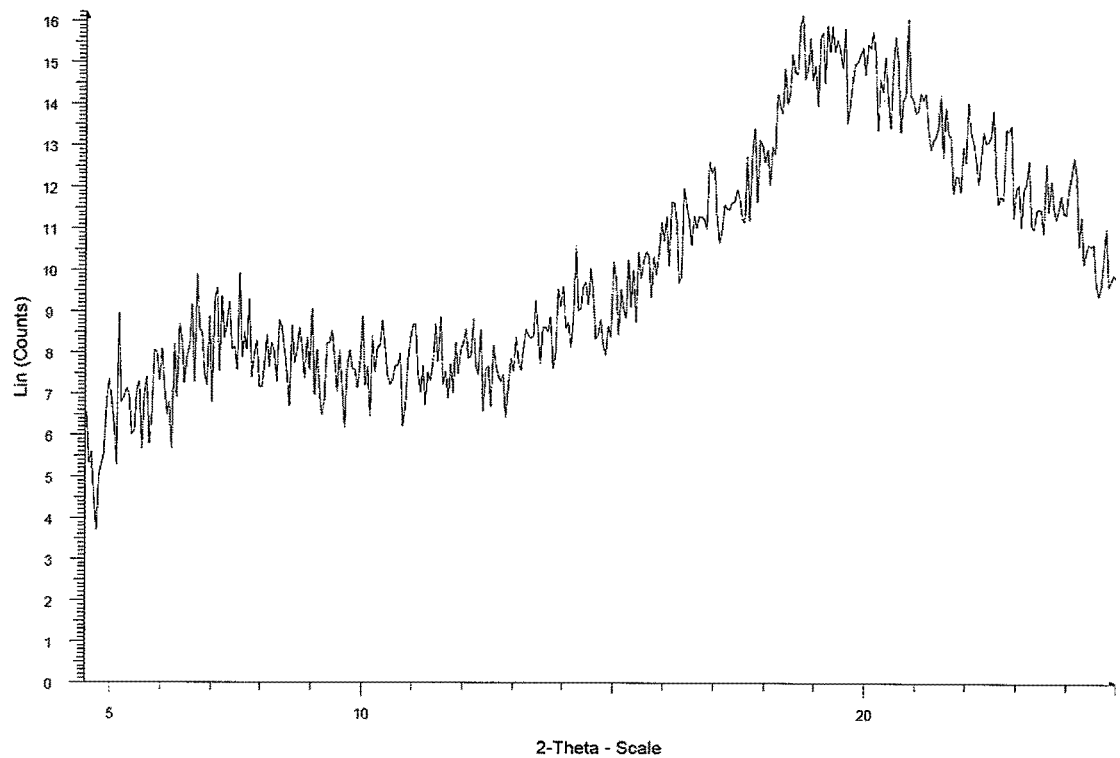
[FIG. 10]
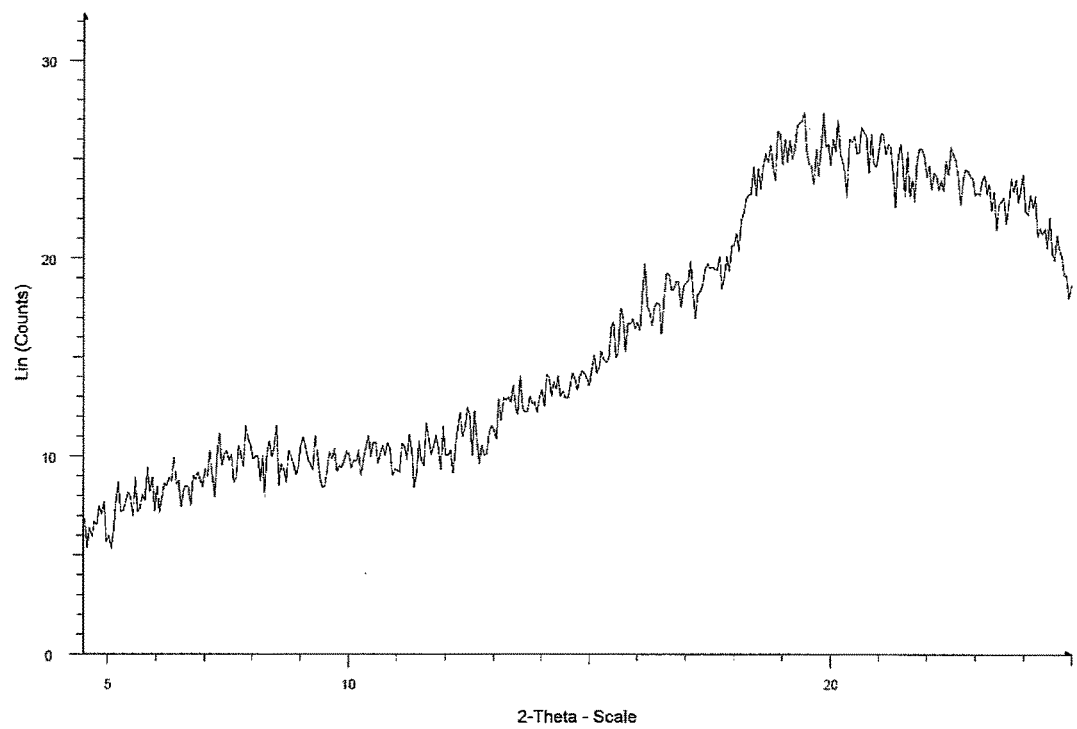

[FIG. 11]
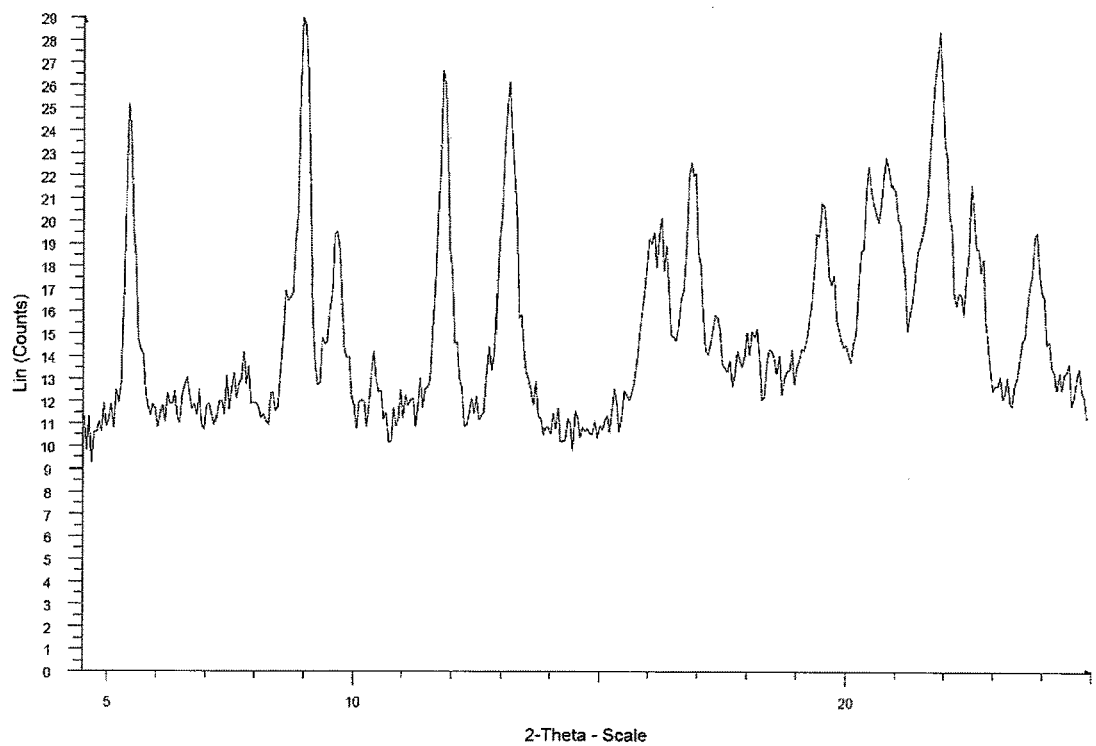
[FIG. 12]
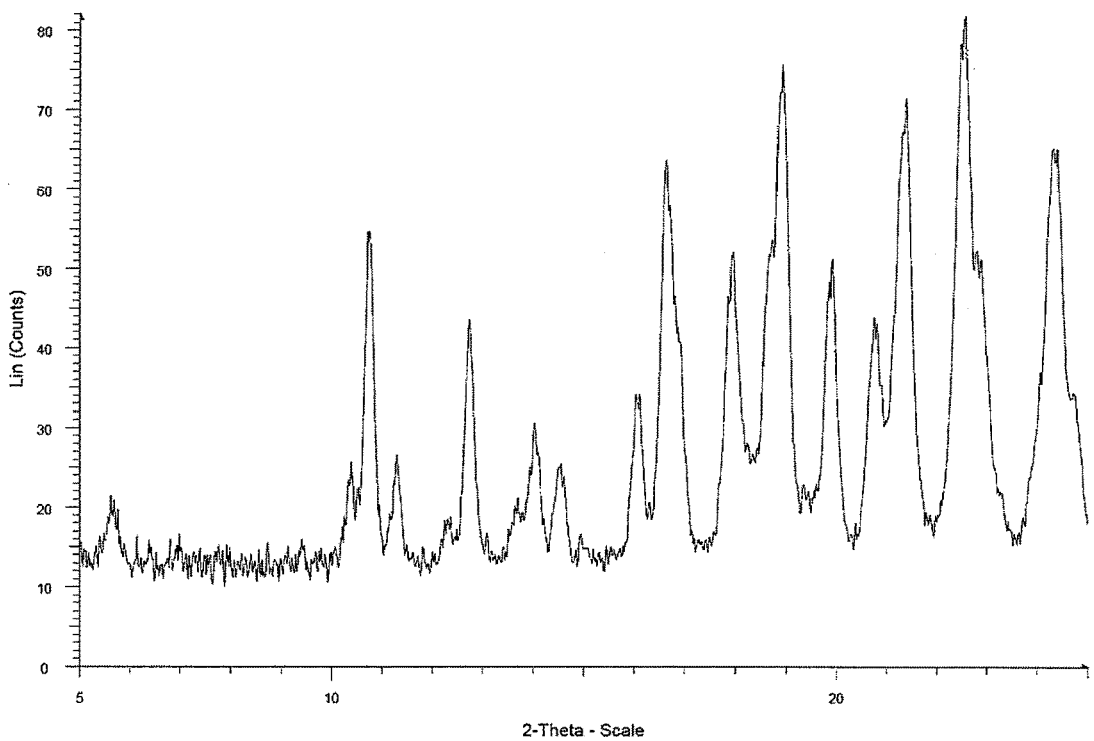

[FIG. 13]
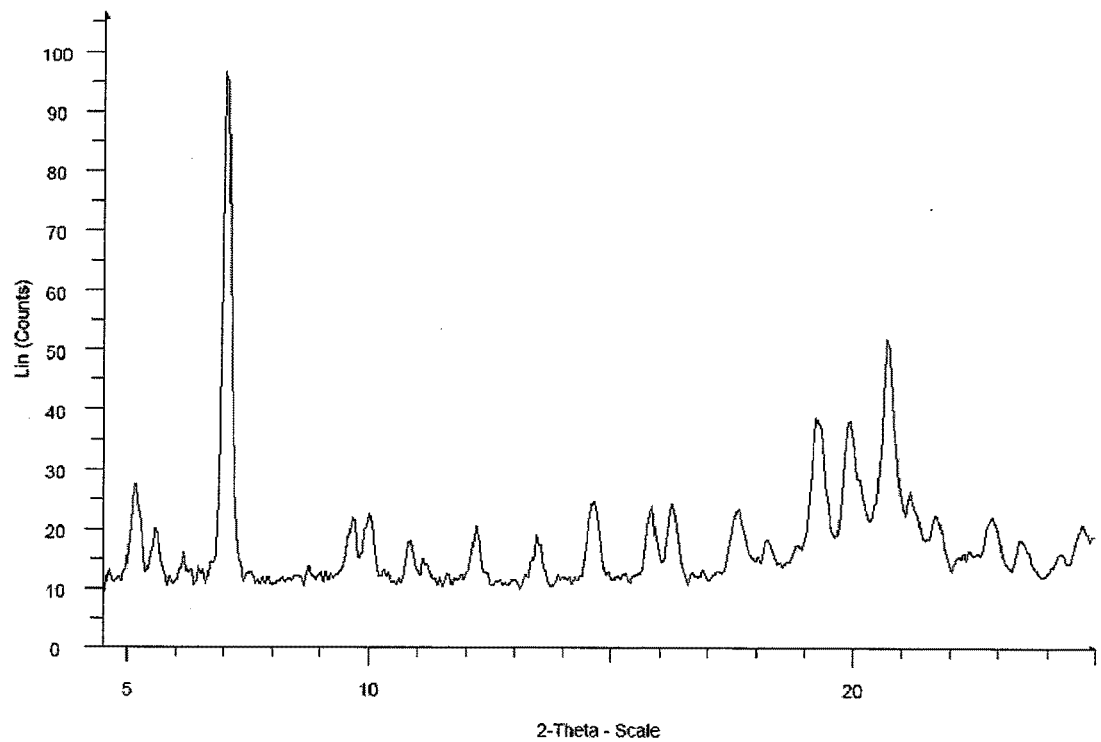
[FIG. 14]
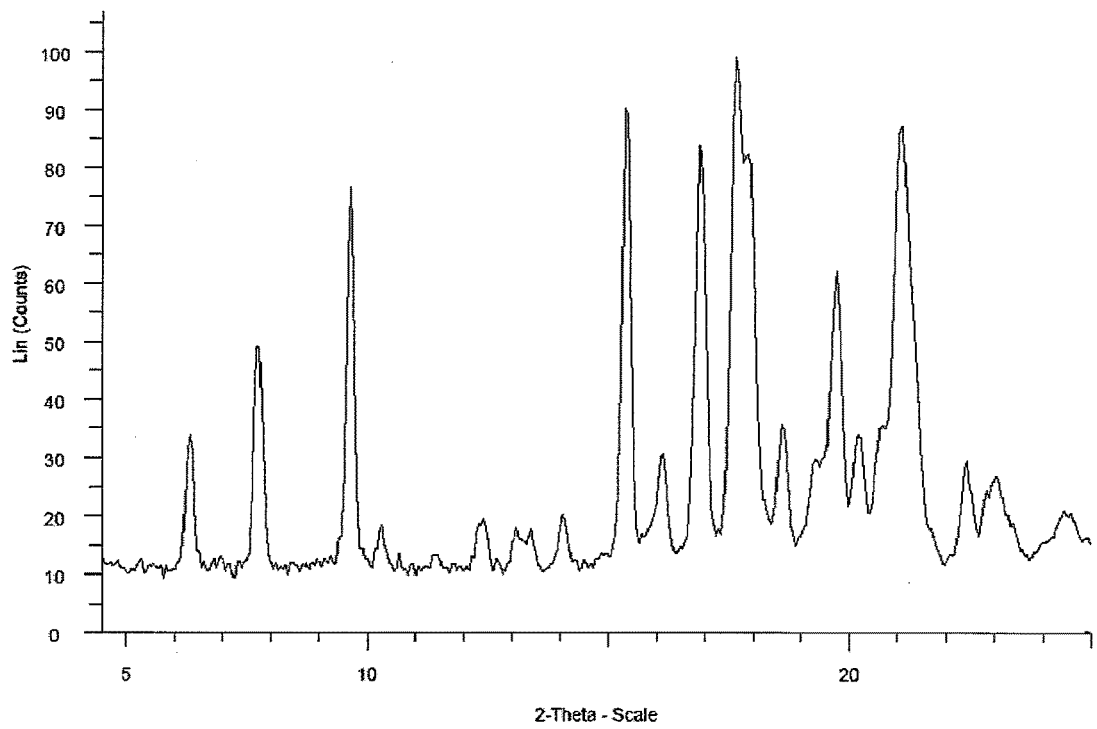

[FIG. 15]
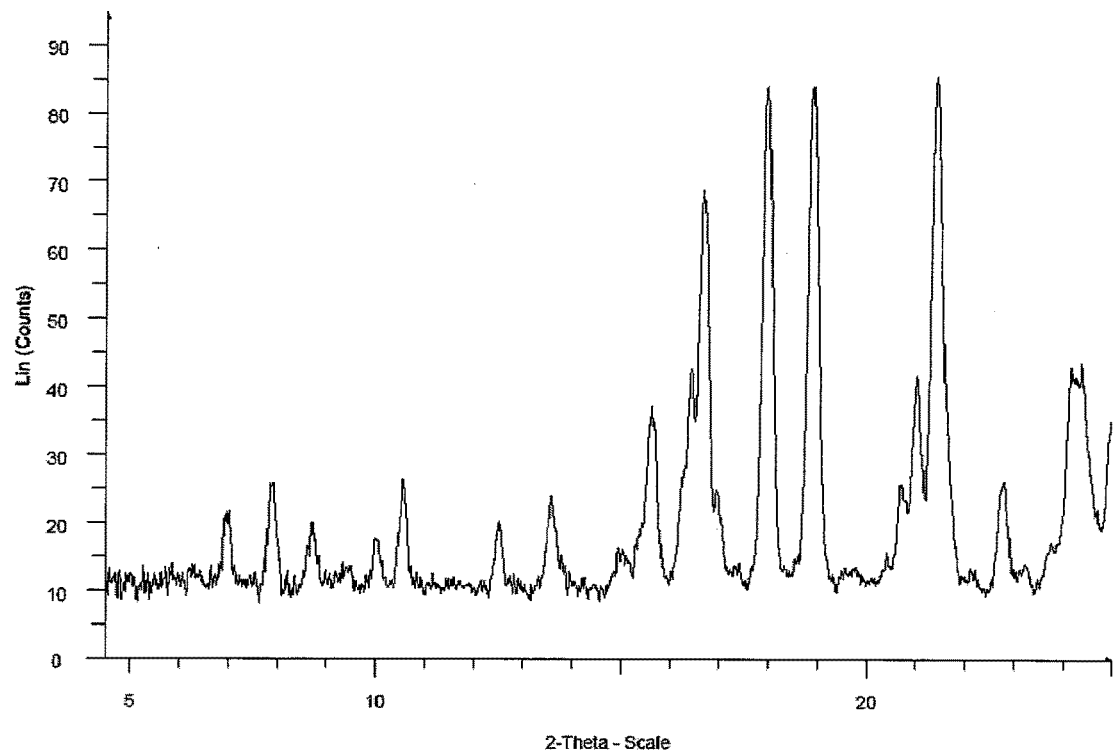
[FIG. 16]
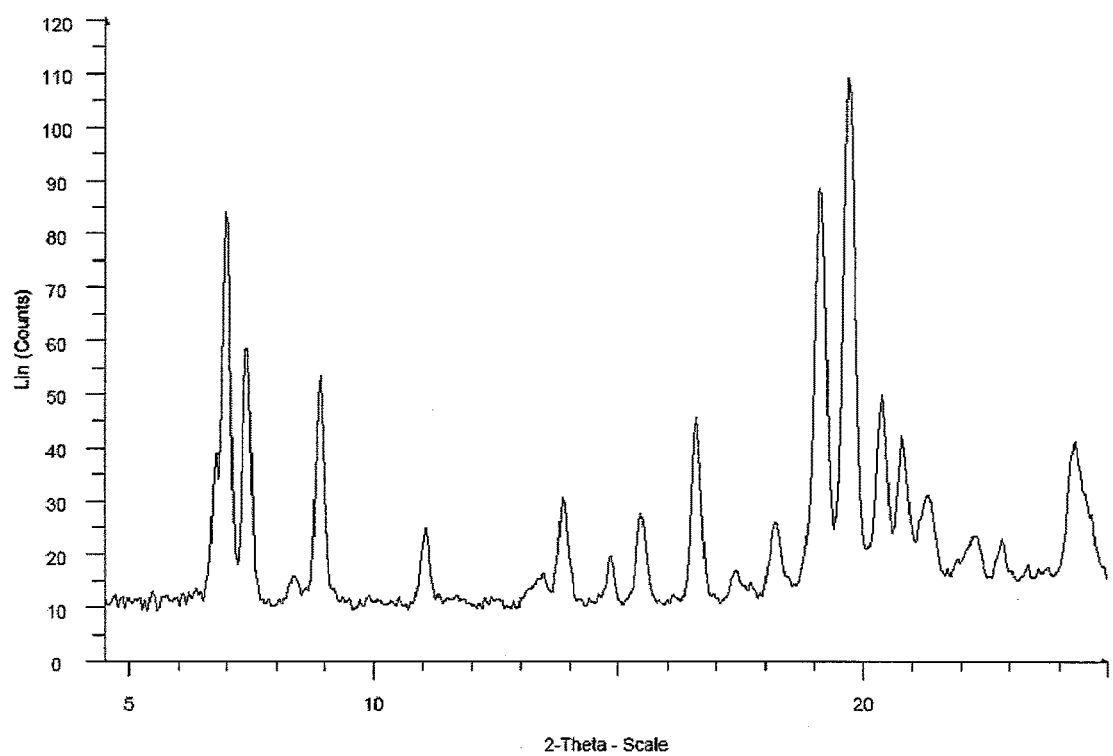

[FIG. 17]
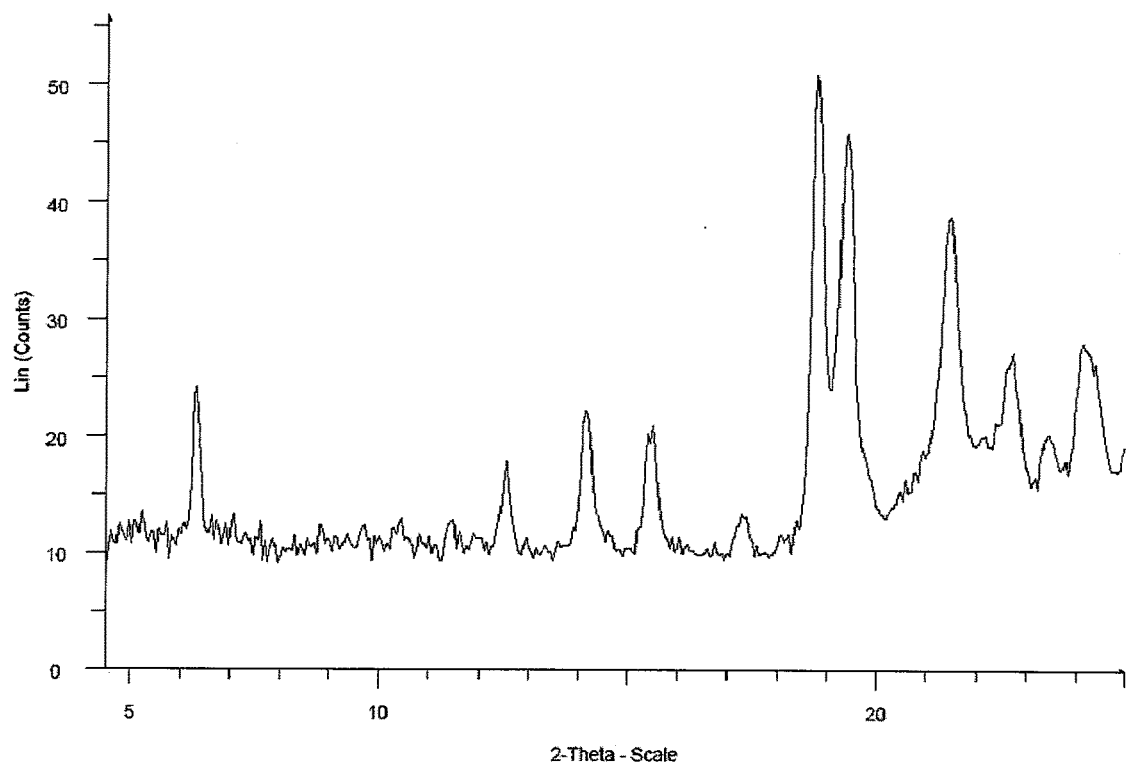
[FIG. 18]
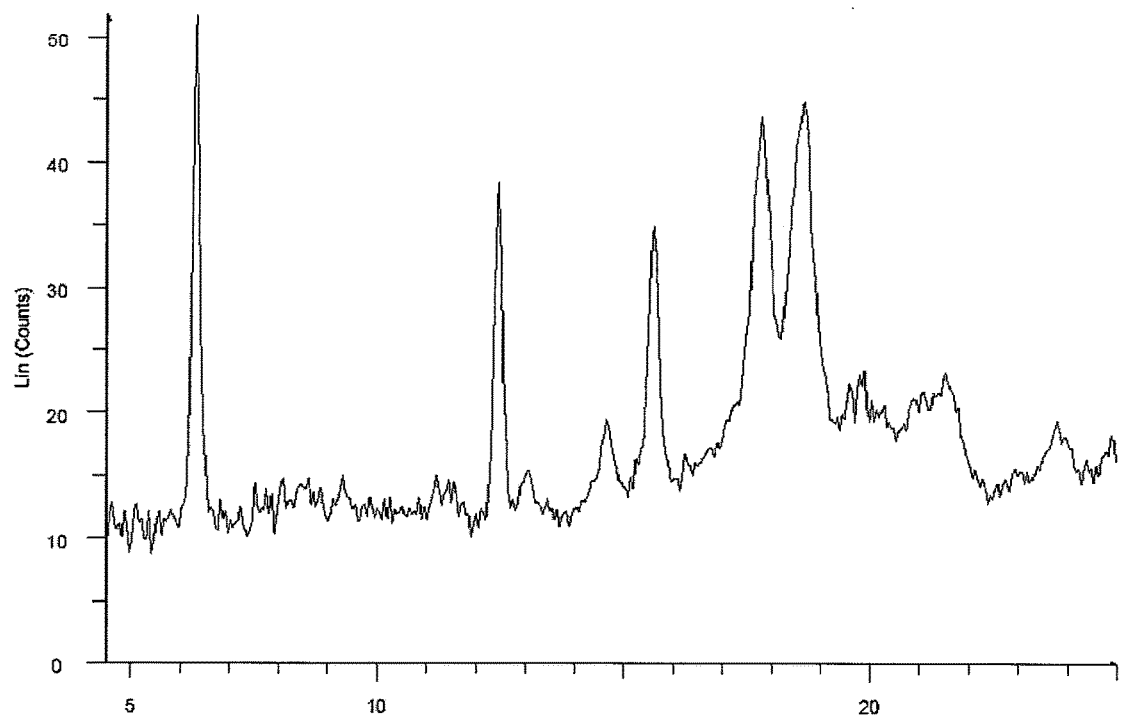

ACID-ADDITION SALT OF TRK-INHIBITING COMPOUND

CROSS-REFERENCE TO RELATED APPLICATIONS

The present application is a U.S. National Phase of International Patent Application No. PCT/JP2015/072990, filed Aug. 17, 2015, which claims priority to Japanese Patent Application No. 2014-165622, filed Aug. 18, 2014, the entireties of which are incorporated herein by reference.

TECHNICAL FIELD

The present invention relates to an acid-addition salt of 1-{2-[4-(2-amino-5-chloro-3-pyridinyl)phenoxy]-5-pyrimidinyl}-3-[2-(methylsulfonyl)-5-(trifluoromethyl)phenyl]urea, 1-{2-[4-(2-amino-5-fluoropyridin-3-yl)phenoxy]pyrimidin-5-yl}-3-[2-(pyridin-3-yl)-5-(trifluoromethyl)phenyl]urea, or 1-(2-(1H-pyrazol-1-yl)-5-(trifluoromethyl)phenyl)-3-(2-(4-(2-amino-5-chloropyridin-3-yl)phenoxy)pyrimidin-5-yl)urea, which exhibits Trk-inhibiting activity and is useful as a prophylactic and/or therapeutic agent for pain, cancer, and the like (hereinafter sometimes abbreviated as "the present compound"), and a crystal thereof, and a pharmaceutical composition thereof.

BACKGROUND ART

The tropomyosin receptor kinase (hereinafter abbreviated as "Trk") family is classified as receptor tyrosine kinases and comprises TrkA which is a high-affinity receptor of nerve growth factor (hereinafter abbreviated as NGF), TrkB which is a high-affinity receptor of brain-derived neutrophic factor (BDNF) and neurotrophin (hereinafter abbreviated as NT)-4/5, and TrkC which is a high-affinity receptor of NT-3. All of the Trk receptors are highly expressed in nerve tissues and are involved in differentiation and maintenance of functions of nerve cells (see Non-Patent Document 1). Meanwhile, it has been known that activation of TrkA in peripheral nerves by NGF initiates hyperalgesia (see Non-Patent Document 2), and based on clinical and non-clinical test results using anti-NGF antibodies or non-clinical test results using low-molecular weight Trk inhibitors, involvement of TrkA has been reported in nociceptive pain of osteoarthritis, chronic low back pain, rheumatoid arthritis, bone fracture, interstitial cystitis, and chronic pancreatitis, neuropathic pain as well as cancer pain combining the both types of pain described above (see Non-Patent Documents 3 to 10). Moreover, the Trk receptors are expressed on cancer cells, such as neuroblastoma, thyroid cancer, lung cancer, breast cancer, pancreatic cancer, colon cancer, prostate cancer, etc., and a possibility of involvement in proliferation, migration, and metastasis of cancer cells is also reported. Especially, fused genes resulting from fusion of TrkA or TrkC with an MPRIP, CD74, TPM3, TPR, TFG, or ETV6 gene are discovered from a part of patients of thyroid cancer, lung cancer, breast cancer, colon cancer, or the like. It is reported that in the cancer having such a fused gene, the Trk kinase is always activated, and a compound having Trk-inhibiting activity inhibits the proliferation of cancer cells. In addition, the Trk receptor is also expressed in inflammatory cells, such as mast cells, eosinophils, etc., immunocompetent cells, such as T cells, B cells, etc., and keratinocytes, and so on, and is reported to be potentially involved in inflammatory diseases, such as ulcerative colitis, Crohn's disease, etc., allergic diseases, such as asthma, rhinitis, atopic dermatitis, and other diseases, such as psoriasis, (see Non-Patent Documents 11 to 15). Therefore, compounds having Trk-inhibiting activity may be possibly applied to therapy of nociceptive pain, neuropathic pain and pain combining the both types of pain, cancer, inflammatory diseases, allergic diseases, psoriasis, and so on.

In view of the foregoing, supposing that drugs capable of inhibiting Trk are created, it is expected that Trk-inhibitors may provide new types of prophylactic and/or therapeutic agents for pain and the like.

Meanwhile, Patent Document 1 discloses a method for treating or preventing a disease in a human or other mammal regulated by tyrosine kinase, comprising administering, to a human or other mammal in need thereof, a compound of the following formula (Ia), a salt thereof, an isomer thereof, or a prodrug thereof.

The general formula (Ia) is as follows:

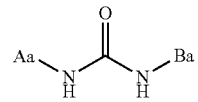

(Ia)

In the formula,

Aa is selected from the group consisting of the following (i) to (iii) and the like:

(i) phenyl which is optionally substituted with 1 to 3 substituents independently selected from the group consisting of $Ra^1$, $ORa^1$, a halogen, and the like;

(ii) naphthyl which is optionally substituted with 1 to 3 substituents independently selected from the group consisting of $Ra^1$, $ORa^1$, a halogen, and the like; and (iii) a 5- to 6-membered monocyclic heteroaryl group having 1 to 3 hetero atoms independently selected from the group consisting of O, N, and S, which is optionally substituted with 1 to 3 substituents independently selected from the group consisting of $Ra^1$, $ORa^1$, a halogen, and the like; and Ba is selected from the group consisting of the following (i) to (iii) and the like:

(i) phenyl which is optionally substituted with 1 to 3 substituents independently selected from the group consisting of —La-Ma, a $C_1$-$C_5$ linear or branched alkyl, a halogen, and the like;

(ii) naphthyl which is optionally substituted with 1 to 3 substituents independently selected from the group consisting of —La-Ma, a $C_1$-$C_5$ linear or branched alkyl, a halogen, and the like; and (iii) a 5- to 6-membered monocyclic heteroaryl group having 1 to 3 hetero atoms independently selected from the group consisting of O, N, and S, which is optionally substituted with 1 to 3 substituents independently selected from the group consisting of —La-Ma, a $C_1$-$C_5$ linear or branched alkyl, a halogen, and the like;

La is selected from the group consisting of —$(CH_2)_{ma}$—O—$(CH_2)_{la}$—, —$(CH_2)_{ma}$—C(O)—$(CH_2)_{la}$—, and the like, wherein the variables ma and la are an integer independently selected from 0 to 4;

Ma is selected from the group consisting of the following (i) to (iii) and the like:

(i) phenyl which is optionally substituted with 1 to 3 substituents independently selected from the group consisting of $Ra^1$, $ORa^1$, a halogen, and the like;

(ii) naphthyl which is optionally substituted with 1 to 3 substituents independently selected from the group consisting of $Ra^1$, $ORa^1$, a halogen, and the like; and (iii) a 5- to 6-membered monocyclic heteroaryl group having 1 to 3 hetero atoms independently selected from the group consisting of O, N, and S, which is optionally substituted with 1 to 3 substituents independently selected from the group consisting of $Ra^1$, $ORa^1$, a halogen, and the like;

wherein $Ra^1$ is independently selected from the group consisting of (a) hydrogen, (b) a $C_1$-$C_6$ alkyl, (c) phenyl, (d) a 5- to 6-membered monocyclic heteroaryl or a 8- to 10-membered bicyclic heteroaryl, each having 1 to 4 hetero atoms selected from the group consisting of O, N, and S, (e) a $C_1$-$C_3$ alkyl-phenyl, and (f) an alkyl-heteroaryl having 1 to 4 hetero atoms selected from the group consisting of O, N, and S; and when $Ra^1$ is not hydrogen, then $Ra^1$ is optionally substituted with 1 to 3 substituents independently selected from the group consisting of a $C_1$-$C_5$ linear, branched, or cyclic alkyl, a $C_1$-$C_3$ alkoxy, hydroxy, amino, a $C_1$-$C_3$ alkylamino, a $C_2$-$C_6$ dialkylamino, a halogen, cyano, and nitro; and the definitions of the groups are partially abstracted.

Patent Document 1 discloses that the compound therein inhibits KDR and is used for a method of treatment of diseases mediated by VEGF induced signal transduction pathways in a human or other mammals, particularly retinopathy or retinopathy of prematurity. However, it is neither disclosed nor suggested that the compound disclosed in the foregoing patent document has Trk-inhibiting activity, and the foregoing patent document does not specifically disclose the present compound, too.

In addition, Patent Document 2 discloses a Trk-inhibiting compound represented by the following formula (Ib) or a salt thereof and a drug containing the same as an active ingredient.

The general formula (Ib) is as follows:

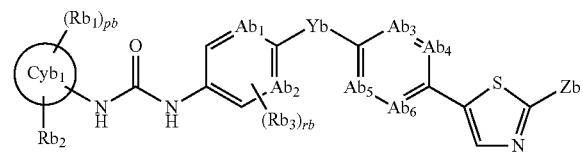

(Ib)

In the formula, the ring $Cyb_1$ represents a $C_3$-$C_{10}$ monocyclic carbon ring or bicyclic carbon ring, or a 4- to 10-membered monocyclic heterocyclic ring or bicyclic heterocyclic ring; $Rb_1$ represents a halogen, a $C_1$-$C_6$ alkyl group which may be substituted with a halogen, or the like; $Rb_2$ represents (1) a $C_1$-$C_6$ alkyl group which may be substituted with a substituent selected from the group consisting of (i) a halogen, (ii) a hydroxyl group, and the like, (2) a hydrogen atom, (3) a hydroxyl group, (4) a carboxyl group, (5) an amino group, (6)

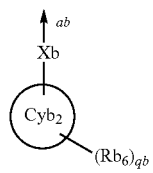

or the like; the arrow ab represents bonding to the ring $Cyb_1$; Xb represents a bond, an oxygen atom, C=O, or NH; the ring $Cyb_2$ represents a $C_3$-$C_{10}$ monocyclic carbon ring or bicyclic carbon ring, or a 4- to 10-membered monocyclic heterocyclic ring or bicyclic heterocyclic ring; $Rb_6$ represents (1) a $C_1$-$C_6$ alkyl group which may be substituted with a substituent selected from the group consisting of (i) a halogen, (ii) a hydroxyl group, and the like, (2) a halogen, (3) a $C_1$-$C_4$ alkoxy group, or the like; $Ab_1$ and $Ab_2$ each independently represent =$CRb_3$—, =CH—, or =N—; $Ab_3$, $Ab_4$, $Ab_5$, and $Ab_6$ each independently represent =$CRb_4$— or =N—; $Rb_3$ represents a halogen or the like; $Rb_4$ represents a halogen or the like; Yb represents an oxygen atom, a sulfur atom which may be oxidized, a methylene group, or C=O; Zb represents

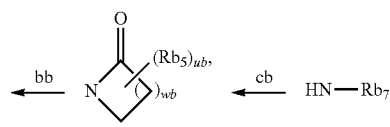

or the like; $Rb_5$ represents a halogen, a hydroxyl group, or a $C_1$-$C_4$ alkyl group which may be substituted with a hydroxyl group; $Rb_7$s each independently represents a $C_1$-$C_6$ alkyl group which may be substituted with a substituent selected from the group consisting of a halogen, a hydroxyl group, and the like, a hydrogen atom, or the like; the arrows bb and cb, and the like represent bonding to the thiazole ring; pb represents an integer of 0 to 5; qb represents an integer of 0 to 7; rb represents an integer of 0 to 2; wb represents an integer of 1 to 5; and ub represents an integer of 0 to 2, provided that when pb, qb, rb, and ub each represent an integer of 2 or more, then $Rb_1$, $Rb_6$, $Rb_3$, and $Rb_5$ may be each independently the same as or different from each other; and the definitions of the groups are partially abstracted.

The Patent Document 2 discloses that this compound therein inhibits Trk, whereby it may become a prophylactic and/or therapeutic agent for pain and the like.

The present invention relates to an acid-addition salt of 1-{2-[4-(2-amino-5-chloro-3-pyridinyl)phenoxy]-5-pyrimidinyl}-3-[2-(methylsulfonyl)-5-(trifluoromethyl)phenyl]urea, 1-{2-[4-(2-amino-5-fluoropyridin-3-yl)phenoxy]pyrimidin-5-yl}-3-[2-(pyridin-3-yl)-5-(trifluoromethyl)phenyl]urea, or 1-(2-(1H-pyrazol-1-yl)-5-(trifluoromethyl)phenyl)-3-(2-(4-(2-amino-5-chloropyridin-3-yl)phenoxy)pyrimidin-5-yl)urea, and any of the cited references neither disclose nor suggest that the foregoing acid-addition salt has a selective Trk-inhibiting action and persistently inhibits NGF vascular hyper permeability and does not have a drug interaction and in addition thereto, is excellent in solubility and absorbability against these free bases.

CITED REFERENCES

Patent Documents

Patent Document 1: WO 2003/068228
Patent Document 2: WO 2013/161919

Non-Patent Documents

Non-Patent Document 1: *Annual Review of Biochemistry*, Vol. 72, pp. 609-642, 2003
Non-Patent Document 2: *Trends in Pharmacological Sciences*, Vol. 27, pp. 85-91, 2006

Non-Patent Document 3: *New England Journal of Medicine*, Vol. 363, pp. 1521-1531, 2010
Non-Patent Document 4: *Pain*, Vol. 152, pp. 2248-2258, 2011
Non-Patent Document 5: *Journal of Urology*, Vol. 185, pp. 1716-1721, 2011
Non-Patent Document 6: *Pain*, Vol. 116, pp. 8-16, 2005
Non-Patent Document 7: *Bone*, Vol. 48, pp. 389-398, 2011
Non-Patent Document 8: *Molecular Pain*, Vol. 6, p. 87, 2010
Non-Patent Document 9: *Journal of Pharmacological and Experimental Therapeutics*, Vol. 322, pp. 282-287, 2007
Non-Patent Document 10: *Gastroenterology*, Vol. 141, pp. 370-377, 2011
Non-Patent Document 11: *Expert Opinion Therapeutic Patents*, Vol. 19, pp. 305-319, 2009
Non-Patent Document 12: *Gut*, Vol. 46, pp. 670-679, 2000
Non-Patent Document 13: *Current Opinion in Allergy and Clinical Immunology*, Vol. 10, pp. 8-13, 2010
Non-Patent Document 14: *Inflammation and Allergy Drug Targets*, Vol. 9, pp. 173-180, 2010
Non-Patent Document 15: *Journal of Investigative Dermatology*, Vol. 126, pp. 1719-1727, 2006
Non-Patent Document 16: *Nature Medicine*, Vol. 19, pp. 1469-1472, 2013

DISCLOSURE OF THE INVENTION

Problems to be Solved by the Invention

In order to provide a prophylactic and/or therapeutic agent for Trk-related diseases, a problem of the present invention is to develop a compound which has a selective Trk-inhibiting activity and persistently inhibits NGF vascular hyper permeability and does not have a drug interaction and in addition thereto, is excellent in solubility and absorbability against free bases. A compound having such properties has been desired.

Means for Solving the Problems

In order to solve the above-described problem, the present inventors made extensive and intensive investigations. As a result, it has been found that the present compound is a compound which has a selective Trk-inhibiting activity and persistently inhibits NGF vascular hyper permeability and does not have a drug interaction and in addition thereto, is excellent in solubility and absorbability against free bases, leading to accomplishment of the present invention.

Specifically, the present invention relates to the followings:

[1] An acid-addition salt of a compound represented by the formula (A):

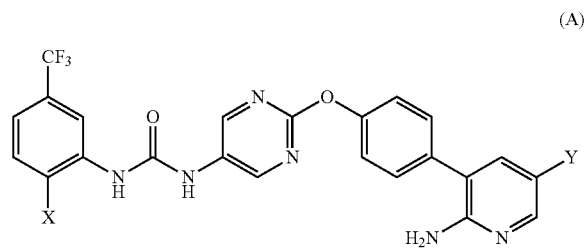

(A)

wherein X is a methanesulfonyl group, a 3-pyridyl group, or a 1-pyrazolyl group; when X is a methanesulfonyl group or a 1-pyrazolyl group, then Y is a chlorine atom; and when X is a 3-pyridyl group, then Y is a fluorine atom.

[2] The salt as set forth in the above item [1], which is an acid-addition salt of 1-{2-[4-(2-amino-5-chloro-3-pyridinyl)phenoxy]-5-pyrimidinyl}-3-[2-(methylsulfonyl)-5-(trifluoromethyl)phenyl]urea.

[3] The salt as set forth in the above item [2], wherein the acid-addition salt is a p-toluenesulfonate, a benzenesulfonate, a methanesulfonate, a hydrochloride, or a hydrobromide.

[4] 1-{2-[4-(2-amino-5-chloro-3-pyridinyl)phenoxy]-5-pyrimidinyl}-3-[2-(methylsulfonyl)-5-(trifluoromethyl)phenyl]urea p-toluenesulfonate.

[5] The salt as set forth in the above item [4], wherein the salt is a crystal.

[6] The salt as set forth in the above item [5], having, in a powder X-ray diffraction spectrum, at least two or more peaks at 2θ selected from about 6.35, 7.74, 9.98, 11.08, 11.42, 12.68, 13.22, 14.83, 15.42, 15.98, 16.89, 17.33, 17.86, 18.29, 19.00, 19.46, 20.56, 20.92, 21.47, 22.04, 23.82, and 24.49.

[7] The salt as set forth in the above item [5] or [6], having, in a powder X-ray diffraction spectrum, peaks at 2θ selected from about 6.35, 7.74, 9.98, 11.08, 11.42, 12.68, 13.22, 14.83, 15.42, 15.98, 16.89, 17.33, 17.86, 18.29, 19.00, 19.46, 20.56, 20.92, 21.47, 22.04, 23.82, and 24.49.

[8] The salt as set forth in any one of the above items [5] to [7], characterized by having a powder X-ray diffraction spectrum chart shown in FIG. 1.

[9] 1-{2-[4-(2-amino-5-chloro-3-pyridinyl)phenoxy]-5-pyrimidinyl}-3-[2-(methylsulfonyl)-5-(trifluoromethyl)phenyl]urea benzenesulfonate.

[10] The salt as set forth in the above item [9], wherein the salt is a crystal.

[11] The salt as set forth in the above item [10], having, in a powder X-ray diffraction spectrum, at least two or more peaks at 2θ selected from about 6.77, 7.78, 10.26, 11.20, 11.50, 13.54, 15.65, 16.02, 17.13, 18.01, 18.41, 18.70, 19.52, 20.25, 20.64, 21.65, 21.95, 22.66, 23.49, and 24.57.

[12] The salt as set forth in the above item [10] or [11], having, in a powder X-ray diffraction spectrum, peaks at 2θ selected from about 6.77, 7.78, 10.26, 11.20, 11.50, 13.54, 15.65, 16.02, 17.13, 18.01, 18.41, 18.70, 19.52, 20.25, 20.64, 21.65, 21.95, 22.66, 23.49, and 24.57.

[13] The salt as set forth in any one of the above items [10] to [12], characterized by having a powder X-ray diffraction spectrum chart shown in FIG. 2.

[14] 1-{2-[4-(2-amino-5-chloro-3-pyridinyl)phenoxy]-5-pyrimidinyl}-3-[2-(methylsulfonyl)-5-(trifluoromethyl)phenyl]urea methanesulfonate.

[15] The salt as set forth in the above item [14], wherein the salt is a crystal.

[16] The salt as set forth in the above item [15], having, in a powder X-ray diffraction spectrum, at least two or more peaks at 2θ selected from about 4.63, 7.04, 9.33, 14.11, 18.74, 20.43, 21.35, 23.31, and 24.80.

[17] The salt as set forth in the above item [15] or [16], having, in a powder X-ray diffraction spectrum, peaks at 2θ selected from about 4.63, 7.04, 9.33, 14.11, 18.74, 20.43, 21.35, 23.31, and 24.80.

[18] The salt as set forth in any one of the above items [15] to [17], characterized by having a powder X-ray diffraction spectrum chart shown in FIG. 3.

[19] 1-{2-[4-(2-amino-5-chloro-3-pyridinyl)phenoxy]-5-pyrimidinyl}-3-[2-(methylsulfonyl)-5-(trifluoromethyl)phenyl]urea hydrochloride.

[20] The salt as set forth in the above item [19], wherein the salt is a crystal.

[21] The salt as set forth in the above item [20], having, in a powder X-ray diffraction spectrum, at least two or more peaks at 2θ selected from about 4.60, 5.95, 7.06, 7.75, 9.38, 10.19, 11.82, 12.21, 13.01, 15.27, 17.81, 18.49, 18.79, 19.89, 20.52, 21.12, 21.96, 22.51, 23.67, and 24.54.

[22] The salt as set forth in the above item [20] or [21], having, in a powder X-ray diffraction spectrum, peaks at 2θ selected from about 4.60, 5.95, 7.06, 7.75, 9.38, 10.19, 11.82, 12.21, 13.01, 15.27, 17.81, 18.49, 18.79, 19.89, 20.52, 21.12, 21.96, 22.51, 23.67, and 24.54.

[23] The salt as set forth in any one of the above items [20] to [22], characterized by having a powder X-ray diffraction spectrum chart shown in FIG. 4.

[24] The salt as set forth in the above item [1], which is an acid-addition salt of 1-{2-[4-(2-amino-5-fluoropyridin-3-yl)phenoxy]pyrimidin-5-yl}-3-[2-(pyridin-3-yl)-5-(trifluoromethyl)phenyl]urea.

[25] The salt as set forth in the above item [24], wherein the acid-addition salt is a p-toluenesulfonate, a benzenesulfonate, a methanesulfonate, a hydrochloride, or a hydrobromide.

[26] 1-{2-[4-(2-amino-5-fluoropyridin-3-yl)phenoxy]pyrimidin-5-yl}-3-[2-(pyridin-3-yl)-5-(trifluoromethyl)phenyl]urea di(p-toluenesulfonate).

[27] The salt as set forth in the above item [26], wherein the salt is a crystal.

[28] The salt as set forth in the above item [27], having, in a powder X-ray diffraction spectrum, at least two or more peaks at 2θ selected from about 6.11, 6.29, 7.76, 9.65, 10.18, 12.30, 12.57, 13.23, 13.59, 14.05, 14.85, 15.47, 16.94, 17.98, 18.52, 18.79, 19.32, 20.58, 21.25, 21.55, 22.11, 22.73, 23.20, and 24.36.

[29] The salt as set forth in the above item [27] or [28], having, in a powder X-ray diffraction spectrum, peaks at 2θ selected from about 6.11, 6.29, 7.76, 9.65, 10.18, 12.30, 12.57, 13.23, 13.59, 14.05, 14.85, 15.47, 16.94, 17.98, 18.52, 18.79, 19.32, 20.58, 21.25, 21.55, 22.11, 22.73, 23.20, and 24.36.

[30] The salt as set forth in any one of the above items [27] to [29], characterized by having a powder X-ray diffraction spectrum chart shown in FIG. 5.

[31] 1-{2-[4-(2-amino-5-fluoropyridin-3-yl)phenoxy]pyrimidin-5-yl}-3-[2-(pyridin-3-yl)-5-(trifluoromethyl)phenyl]urea dibenzenesulfonate.

[32] The salt as set forth in the above item [31], wherein the salt is a crystal.

[33] The salt as set forth in the above item [32], having, in a powder X-ray diffraction spectrum, at least two or more peaks at 2θ selected from about 5.99, 6.71, 7.78, 10.08, 10.42, 11.93, 12.53, 12.96, 13.41, 14.15, 15.16, 15.55, 16.03, 16.93, 17.52, 17.95, 18.63, 18.91, 19.50, 20.18, 20.73, 21.43, 22.43, 22.84, 23.60, and 23.97.

[34] The salt as set forth in the above item [32] or [33], having, in a powder X-ray diffraction spectrum, peaks at 2θ selected from about 5.99, 6.71, 7.78, 10.08, 10.42, 11.93, 12.53, 12.96, 13.41, 14.15, 15.16, 15.55, 16.03, 16.93, 17.52, 17.95, 18.63, 18.91, 19.50, 20.18, 20.73, 21.43, 22.43, 22.84, 23.60, and 23.97.

[35] The salt as set forth in any one of the above items [32] to [34], characterized by having a powder X-ray diffraction spectrum chart shown in FIG. 6.

[36] 1-{2-[4-(2-amino-5-fluoropyridin-3-yl)phenoxy]pyrimidin-5-yl}-3-[2-(pyridin-3-yl)-5-(trifluoromethyl)phenyl]urea dimethanesulfonate.

[37] The salt as set forth in the above item [36], wherein the salt is a crystal.

[38] The salt as set forth in the above item [37], having, in a powder X-ray diffraction spectrum, at least two or more peaks at 2θ selected from about 5.30, 5.93, 8.91, 9.34, 9.64, 10.55, 11.77, 12.52, 12.92, 13.72, 14.25, 15.47, 15.91, 16.87, 17.87, 18.77, 19.30, 19.62, 20.77, 21.23, 21.61, 22.47, 23.36, 23.78, and 24.51.

[39] The salt as set forth in the above item [37] or [38], having, in a powder X-ray diffraction spectrum, peaks at 2θ selected from about 5.30, 5.93, 8.91, 9.34, 9.64, 10.55, 11.77, 12.52, 12.92, 13.72, 14.25, 15.47, 15.91, 16.87, 17.87, 18.77, 19.30, 19.62, 20.77, 21.23, 21.61, 22.47, 23.36, 23.78, and 24.51.

[40] The salt as set forth in any one of the above items [37] to [39], characterized by having a powder X-ray diffraction spectrum chart shown in FIG. 7.

[41] 1-{2-[4-(2-amino-5-fluoropyridin-3-yl)phenoxy]pyrimidin-5-yl}-3-[2-(pyridin-3-yl)-5-(trifluoromethyl)phenyl]urea dihydrochloride.

[42] The salt as set forth in the above item [41], wherein the salt is a crystal.

[43] The salt as set forth in the above item [42], having, in a powder X-ray diffraction spectrum, at least two or more peaks at 2θ selected from about 6.03, 6.84, 8.30, 9.87, 12.52, 13.70, 13.93, 14.90, 15.88, 18.31, 19.81, 20.94, 22.47, 22.89, and 24.08.

[44] The salt as set forth in the above item [42] or [43], having, in a powder X-ray diffraction spectrum, peaks at 2θ selected from about 6.03, 6.84, 8.30, 9.87, 12.52, 13.70, 13.93, 14.90, 15.88, 18.31, 19.81, 20.94, 22.47, 22.89, and 24.08.

[45] The salt as set forth in any one of the above items [42] to [44], characterized by having a powder X-ray diffraction spectrum chart shown in FIG. 8.

[46] The salt as set forth in the above item [1], which is an acid-addition salt of 1-(2-(1H-pyrazol-1-yl)-5-(trifluoromethyl)phenyl)-3-(2-(4-(2-amino-5-chloropyridin-3-yl)phenoxy)pyrimidin-5-yl)urea.

[47] The salt as set forth in the above item [46], wherein the acid-addition salt is a p-toluenesulfonate, a benzenesulfonate, a methanesulfonate, a hydrochloride, or a hydrobromide.

[48] 1-(2-(1H-pyrazol-1-yl)-5-(trifluoromethyl)phenyl)-3-(2-(4-(2-amino-5-chloropyridin-3-yl)phenoxy)pyrimidin-5-yl)urea p-toluenesulfonate.

[49] The salt as set forth in the above item [48], characterized by having a powder X-ray diffraction spectrum chart shown in FIG. 9.

[50] 1-(2-(1H-pyrazol-1-yl)-5-(trifluoromethyl)phenyl)-3-(2-(4-(2-amino-5-chloropyridin-3-yl)phenoxy)pyrimidin-5-yl)urea benzenesulfonate.

[51] The salt as set forth in the above item [50], characterized by having a powder X-ray diffraction spectrum chart shown in FIG. 10.

[52] 1-(2-(1H-pyrazol-1-yl)-5-(trifluoromethyl)phenyl)-3-(2-(4-(2-amino-5-chloropyridin-3-yl)phenoxy)pyrimidin-5-yl)urea methanesulfonate.

[53] The salt as set forth in the above item [52], wherein the salt is a crystal.

[54] The salt as set forth in the above item [53], having, in a powder X-ray diffraction spectrum, at least two or more peaks at 2θ selected from about 5.42, 8.64, 8.97, 9.64, 10.39, 11.85, 13.13, 16.02, 16.27, 16.89, 17.39, 18.19, 19.53, 20.49, 20.83, 21.89, 22.59, and 23.90.

[55] The salt as set forth in the above item [53] or [54], having, in a powder X-ray diffraction spectrum, peaks at 2θ selected from about 5.42, 8.64, 8.97, 9.64, 10.39, 11.85, 13.13, 16.02, 16.27, 16.89, 17.39, 18.19, 19.53, 20.49, 20.83, 21.89, 22.59, and 23.90.

[56] The salt as set forth in any one of the above items [53] to [55], characterized by having a powder X-ray diffraction spectrum chart shown in FIG. 11.

[57] 1-(2-(1H-pyrazol-1-yl)-5-(trifluoromethyl)phenyl)-3-(2-(4-(2-amino-5-chloropyridin-3-yl)phenoxy)pyrimidin-5-yl)urea hydrochloride.

[58] The salt as set forth in the above item [57], wherein the salt is a crystal.

[59] The salt as set forth in the above item [58], having, in a powder X-ray diffraction spectrum, at least two or more peaks at 2θ selected from about 5.63, 10.37, 10.73, 11.29, 12.30, 12.73, 13.68, 14.03, 14.53, 16.07, 16.64, 17.93, 18.66, 18.91, 19.89, 20.76, 21.35, 22.52, 22.84, 24.33, and 24.74.

[60] The salt as set forth in the above item [58] or [59], having, in a powder X-ray diffraction spectrum, peaks at 2θ selected from about 5.63, 10.37, 10.73, 11.29, 12.30, 12.73, 13.68, 14.03, 14.53, 16.07, 16.64, 17.93, 18.66, 18.91, 19.89, 20.76, 21.35, 22.52, 22.84, 24.33, and 24.74.

[61] The salt as set forth in any one of the above items [58] to [60], characterized by having a powder X-ray diffraction spectrum chart shown in FIG. 12.

[62] A pharmaceutical composition containing the salt as set forth in the above item [1].

[63] A pharmaceutical composition containing an acid-addition salt of 1-{2-[4-(2-amino-5-chloro-3-pyridinyl)phenoxy]-5-pyrimidinyl}-3-[2-(methylsulfonyl)-5-(trifluoromethyl)phenyl]urea.

[64] A pharmaceutical composition containing an acid-addition salt of 1-{2-[4-(2-amino-5-fluoropyridin-3-yl)phenoxy]pyrimidin-5-yl}-3-[2-(pyridin-3-yl)-5-(trifluoromethyl)phenyl]urea.

[65] A pharmaceutical composition containing an acid-addition salt of 1-(2-(1H-pyrazol-1-yl)-5-(trifluoromethyl)phenyl)-3-(2-(4-(2-amino-5-chloropyridin-3-yl)phenoxy)pyrimidin-5-yl)urea.

[66] The composition as set forth in any one of the above items [62] to [65], which is a Trk inhibitor.

[67] The composition as set forth in any one of the above items [62] to [65], which is a prophylactic and/or therapeutic agent for Trk-related disease.

[68] The composition as set forth in the above item [67], wherein the Trk-related disease is pain, pruritus, lower urinary tract dysfunction, asthma, allergic rhinitis, inflammatory bowel disease, Chagas disease, or cancer.

[69] The composition as set forth in the above item [68], wherein the pain is pain of osteoarthritis, cancer pain, chronic low back pain, low back pain of osteoporosis, pain of bone fracture, pain of rheumatoid arthritis, neuropathic pain, postherpetic pain, pain of diabetic neuropathy, fibromyalgia, pain of pancreatitis, pain of interstitial cystitis, pain of endometriosis, pain of irritable bowel syndrome, migraine, postoperative pain, or pain of pulpitis

[70] The composition as set forth in the above item [68], wherein the cancer is breast cancer, colon cancer, lung cancer, thyroid cancer, skin cancer, leukemia, tumors of salivary gland, neuroendocrine tumor, lymphoma, cerebral tumor, neuroblastoma, ovarian cancer, pancreatic cancer, mesothelioma, esophageal carcinoma, pulmonary sarcoma, medulloblastoma, glioblastoma, colon cancer, liver cancer, retinoblastoma, kidney cancer, bladder cancer, osteosarcoma, stomach cancer, uterine cancer, vulvar cancer, small intestinal cancer, prostate cancer, bile duct cancer, ureterocele, adrenal cortical carcinoma, or head and neck cancer.

[71] A medicament containing a combination of the compound as set forth in the above item [1], [2], [24], or [46] with at least one selected from acetaminophen, a nonsteroid antiinflammatory drug, an opioid, an antidepressant, an antiepileptic agent, an N-methyl-D-aspartate antagonist, a muscle relaxant, an antiarrhythmic agent, a steroid, and a bisphosphonate.

[72] A medicament containing a combination of the compound as set forth in the above item [1], [2], [24], or [46] with at least one selected from an alkylating agent, a metabolic antagonist, an anticancer antibiotics, an anticancer vegetable preparation, a hormone drug, a platinum compound, a topoisomerase inhibitor, a kinase inhibitor, an anti-CD20 antibody, an anti-HER2 antibody, an anti-EGFR antibody, an anti-VEGF antibody, an anti-PD-1 antibody, and an anti-PD-L1 antibody.

[73] A method for preventing and/or treating Trk-related disease, characterized by administering, to a patient, an effective amount of the compound as set forth in the above item [1], [2], [24], or [46].

[74] The compound as set forth in the above item [1], [2], [24], or [46] for prophylaxis and/or therapy of Trk-related disease.

[75] Use of the compound as set forth in the above item [1], [2], [24], or [46] for producing a prophylactic and/or therapeutic agent for Trk-related disease.

[76] The salt as set forth in the above item [5], having, in a powder X-ray diffraction spectrum, at least two or more peaks at 2θ selected from about 5.16, 5.57, 7.01, 9.62, 9.97, 10.83, 11.15, 12.20, 13.47, 14.63, 15.81, 16.30, 17.63, 18.26, 19.28, 19.93, 20.72, 21.25, 21.73, 22.88, 23.51, 24.30, and 24.74.

[77] The salt as set forth in the above item [5] or [76], having, in a powder X-ray diffraction spectrum, peaks at 2θ selected from about 5.16, 5.57, 7.01, 9.62, 9.97, 10.83, 11.15, 12.20, 13.47, 14.63, 15.81, 16.30, 17.63, 18.26, 19.28, 19.93, 20.72, 21.25, 21.73, 22.88, 23.51, 24.30, and 24.74.

[78] The salt as set forth in the above item [5], [76], or [77], characterized by having a powder X-ray diffraction spectrum chart shown in FIG. 13.

[79] The salt as set forth in the above item [5], having, in a powder X-ray diffraction spectrum, at least two or more peaks at 2θ selected from about 6.30, 7.72, 9.63, 10.27, 11.44, 12.39, 13.11, 13.36, 14.10, 15.40, 16.14, 16.94, 17.69, 17.90, 18.65, 19.33, 19.73, 20.23, 20.68, 21.09, 22.44, 23.02, and 24.51.

[80] The salt as set forth in the above item [5] or [79], having, in a powder X-ray diffraction spectrum, peaks at 2θ selected from about 6.30, 7.72, 9.63, 10.27, 11.44, 12.39, 13.11, 13.36, 14.10, 15.40, 16.14, 16.94, 17.69, 17.90, 18.65, 19.33, 19.73, 20.23, 20.68, 21.09, 22.44, 23.02, and 24.51.

[81] The salt as set forth in the above item [5], [79], or [80], characterized by having a powder X-ray diffraction spectrum chart shown in FIG. 14.

[82] The salt as set forth in the above item [10], having, in a powder X-ray diffraction spectrum, at least two or more peaks at 2θ selected from about 6.96, 7.87, 8.69, 9.44, 10.02, 10.55, 12.51, 13.59, 15.02, 15.65, 16.42, 16.69, 17.00, 17.98, 18.91, 20.44, 20.74, 21.04, 21.44, 22.79, 24.22, and 24.37.

[83] The salt as set forth in the above item [10] or [82], having, in a powder X-ray diffraction spectrum, peaks at 2θ selected from about 6.96, 7.87, 8.69, 9.44, 10.02, 10.55, 12.51, 13.59, 15.02, 15.65, 16.42, 16.69, 17.00, 17.98, 18.91, 20.44, 20.74, 21.04, 21.44, 22.79, 24.22, and 24.37.

[84] The salt as set forth in the above item [10], [82], or [83], characterized by having a powder X-ray diffraction spectrum chart shown in FIG. 15.

[85] The salt as set forth in the above item [10], having, in a powder X-ray diffraction spectrum, at least two or more peaks at 2θ selected from about 6.70, 6.97, 7.37, 8.36, 8.88, 11.04, 13.40, 13.88, 14.84, 15.48, 16.59, 17.40, 18.24, 19.12, 19.73, 20.38, 20.83, 21.32, 22.30, 22.85, and 24.33.

[86] The salt as set forth in the above item [10] or [85], having, in a powder X-ray diffraction spectrum, peaks at 2θ selected from about 6.70, 6.97, 7.37, 8.36, 8.88, 11.04, 13.40, 13.88, 14.84, 15.48, 16.59, 17.40, 18.24, 19.12, 19.73, 20.38, 20.83, 21.32, 22.30, 22.85, and 24.33.

[87] The salt as set forth in the above item [10], [85], or [86], characterized by having a powder X-ray diffraction spectrum chart shown in FIG. 16.

[88] 1-{2-[4-(2-amino-5-chloro-3-pyridinyl)phenoxy]-5-pyrimidinyl}-3-[2-(methylsulfonyl)-5-(trifluoromethyl)phenyl]urea hydrobromide.

[89] The salt as set forth in the above item [88], wherein the salt is a crystal.

[90] The salt as set forth in the above item [89], having, in a powder X-ray diffraction spectrum, at least two or more peaks at 2θ selected from about 6.28 12.53, 14.15, 15.51, 17.35, 18.80, 19.40, 21.48, 22.67, 23.44, and 24.15.

[91] The salt as set forth in the above item [89] or [90], having, in a powder X-ray diffraction spectrum, peaks at 2θ selected from about 6.28 12.53, 14.15, 15.51, 17.35, 18.80, 19.40, 21.48, 22.67, 23.44, and 24.15.

[92] The salt as set forth in any one of the above items [89] to [91], characterized by having a powder X-ray diffraction spectrum chart shown in FIG. 17.

[93] The salt as set forth in the above item [5], having, in a powder X-ray diffraction spectrum, at least two or more peaks at 2θ selected from about 6.30, 12.44, 13.00, 14.68, 15.61, 17.79, 18.62, 21.54, and 23.82.

[94] The salt as set forth in the above item [5] or [93], having, in a powder X-ray diffraction spectrum, peaks at 2θ selected from about 6.30, 12.44, 13.00, 14.68, 15.61, 17.79, 18.62, 21.54, and 23.82.

[95] The salt as set forth in the above item [5], [93], or [94], characterized by having a powder X-ray diffraction spectrum chart shown in FIG. 18.

Effect of the Invention

The present compound exhibits selective Trk-inhibiting activity and thus is useful as a prophylactic and/or therapeutic agent for Trk-related diseases, such as pain, pruritus, lower urinary tract dysfunction, asthma, allergic rhinitis, inflammatory bowel disease, Chagas disease, cancer, etc.

BRIEF DESCRIPTION OF THE DRAWINGS

FIG. 1 shows a powder X-ray diffraction spectrum chart of a crystal (crystal A) of 1-{2-[4-(2-amino-5-chloro-3-pyridinyl)phenoxy]-5-pyrimidinyl}-3-[2-(methylsulfonyl)-5-(trifluoromethyl)phenyl]urea p-toluenesulfonate (in FIG. 1, the ordinate indicates an intensity (counts), and the abscissa indicates 2 θ (degree)).

FIG. 2 shows a powder X-ray diffraction spectrum chart of a crystal (crystal A) of 1-{2-[4-(2-amino-5-chloro-3-pyridinyl)phenoxy]-5-pyrimidinyl}-3-[2-(methylsulfonyl)-5-(trifluoromethyl)phenyl]urea benzenesulfonate (in FIG. 2, the ordinate indicates an intensity (counts), and the abscissa indicates 2 θ (degree)).

FIG. 3 shows a powder X-ray diffraction spectrum chart of a crystal of 1-{2-[4-(2-amino-5-chloro-3-pyridinyl)phenoxy]-5-pyrimidinyl}-3-[2-(methylsulfonyl)-5-(trifluoromethyl)phenyl]urea methanesulfonate (in FIG. 3, the ordinate indicates an intensity (counts), and the abscissa indicates 2 θ (degree)).

FIG. 4 shows a powder X-ray diffraction spectrum chart of a crystal of 1-{2-[4-(2-amino-5-chloro-3-pyridinyl)phenoxy]-5-pyrimidinyl}-3-[2-(methylsulfonyl)-5-(trifluoromethyl)phenyl]urea hydrochloride (in FIG. 4, the ordinate indicates an intensity (counts), and the abscissa indicates 2 θ (degree)).

FIG. 5 shows a powder X-ray diffraction spectrum chart of a crystal of 1-{2-[4-(2-amino-5-fluoropyridin-3-yl)phenoxy]pyrimidin-5-yl}-3-[2-(pyridin-3-yl)-5-(trifluoromethyl)phenyl]urea di(p-toluenesulfonate) (in FIG. 5, the ordinate indicates an intensity (counts), and the abscissa indicates 2 θ (degree)).

FIG. 6 shows a powder X-ray diffraction spectrum chart of a crystal of 1-{2-[4-(2-amino-5-fluoropyridin-3-yl)phenoxy]pyrimidin-5-yl}-3-[2-(pyridin-3-yl)-5-(trifluoromethyl)phenyl]urea dibenzenesulfonate (in FIG. 6, the ordinate indicates an intensity (counts), and the abscissa indicates 2 θ (degree)).

FIG. 7 shows a powder X-ray diffraction spectrum chart of a crystal of 1-{2-[4-(2-amino-5-fluoropyridin-3-yl)phenoxy]pyrimidin-5-yl}-3-[2-(pyridin-3-yl)-5-(trifluoromethyl)phenyl]urea dimethanesulfonate (in FIG. 7, the ordinate indicates an intensity (counts), and the abscissa indicates 2 θ (degree)).

FIG. 8 shows a powder X-ray diffraction spectrum chart of a crystal of 1-{2-[4-(2-amino-5-fluoropyridin-3-yl)phenoxy]pyrimidin-5-yl}-3-[2-(pyridin-3-yl)-5-(trifluoromethyl)phenyl]urea dihydrochloride (in FIG. 8, the ordinate indicates an intensity (counts), and the abscissa indicates 2 θ (degree)).

FIG. 9 shows a powder X-ray diffraction spectrum chart of an amorphous material of 1-(2-(1H-pyrazol-1-yl)-5-(trifluoromethyl)phenyl)-3-(2-(4-(2-amino-5-chloropyridin-3-yl)phenoxy)pyrimidin-5-yl)urea p-toluenesulfonate (in FIG. 9, the ordinate indicates an intensity (counts), and the abscissa indicates 2 θ (degree)).

FIG. 10 shows a powder X-ray diffraction spectrum chart of an amorphous material of 1-(2-(1H-pyrazol-1-yl)-5-(trifluoromethyl)phenyl)-3-(2-(4-(2-amino-5-chloropyridin-3-yl)phenoxy)pyrimidin-5-yl)urea benzenesulfonate (in FIG. 10, the ordinate indicates an intensity (counts), and the abscissa indicates 2 θ (degree)).

FIG. 11 shows a powder X-ray diffraction spectrum chart of a crystal of 1-(2-(1H-pyrazol-1-yl)-5-(trifluoromethyl)phenyl)-3-(2-(4-(2-amino-5-chloropyridin-3-yl)phenoxy)pyrimidin-5-yl)urea methanesulfonate (in FIG. 11, the ordinate indicates an intensity (counts), and the abscissa indicates 2 θ (degree)).

FIG. 12 shows a powder X-ray diffraction spectrum chart of a crystal of 1-(2-(1H-pyrazol-1-yl)-5-(trifluoromethyl)phenyl)-3-(2-(4-(2-amino-5-chloropyridin-3-yl)phenoxy)pyrimidin-5-yl)urea hydrochloride (in FIG. 12, the ordinate indicates an intensity (counts), and the abscissa indicates 2 θ (degree)).

FIG. 13 shows a powder X-ray diffraction spectrum chart of a crystal (crystal B) of 1-{2-[4-(2-amino-5-chloro-3-pyridinyl)phenoxy]-5-pyrimidinyl}-3-[2-(methylsulfonyl)-5-(trifluoromethyl)phenyl]urea p-toluenesulfonate (in FIG. 13, the ordinate indicates an intensity (counts), and the abscissa indicates 2 θ (degree)).

FIG. 14 shows a powder X-ray diffraction spectrum chart of a crystal (crystal I) of 1-{2-[4-(2-amino-5-chloro-3-pyridinyl)phenoxy]-5-pyrimidinyl}-3-[2-(methylsulfonyl)-5-(trifluoromethyl)phenyl]urea p-toluenesulfonate (in FIG. 14, the ordinate indicates an intensity (counts), and the abscissa indicates 2 θ (degree)).

FIG. 15 shows a powder X-ray diffraction spectrum chart of a crystal (crystal B) of 1-{2-[4-(2-amino-5-chloro-3-pyridinyl)phenoxy]-5-pyrimidinyl}-3-[2-(methylsulfonyl)-5-(trifluoromethyl)phenyl]urea benzenesulfonate (in FIG. 15, the ordinate indicates an intensity (counts), and the abscissa indicates 2 θ (degree)).

FIG. 16 shows a powder X-ray diffraction spectrum chart of a crystal (crystal F) of 1-{2-[4-(2-amino-5-chloro-3-pyridinyl)phenoxy]-5-pyrimidinyl}-3-[2-(methylsulfonyl)-5-(trifluoromethyl)phenyl]urea benzenesulfonate (in FIG. 16, the ordinate indicates an intensity (counts), and the abscissa indicates 2 θ (degree)).

FIG. 17 shows a powder X-ray diffraction spectrum chart of a crystal of 1-{2-[4-(2-amino-5-chloro-3-pyridinyl)phenoxy]-5-pyrimidinyl}-3-[2-(methylsulfonyl)-5-(trifluoromethyl)phenyl]urea hydrobromide (in FIG. 17, the ordinate indicates an intensity (counts), and the abscissa indicates 2 θ (degree)).

FIG. 18 shows a powder X-ray diffraction spectrum chart of a crystal (crystal F) of 1-{2-[4-(2-amino-5-chloro-3-pyridinyl)phenoxy]-5-pyrimidinyl}-3-[2-(methylsulfonyl)-5-(trifluoromethyl)phenyl]urea p-toluenesulfonate (in FIG. 18, the ordinate indicates an intensity (counts), and the abscissa indicates 2 θ (degree)).

EMBODIMENTS FOR CARRYING OUT THE INVENTION

The present invention is hereunder described in detail.

In the present invention, the 1-{2-[4-(2-amino-5-chloro-3-pyridinyl)phenoxy]-5-pyrimidinyl}-3-[2-(methylsulfonyl)-5-(trifluoromethyl)phenyl]urea (hereinafter sometimes abbreviated as "Compound (I)") is
a compound represented by the following structural formula:

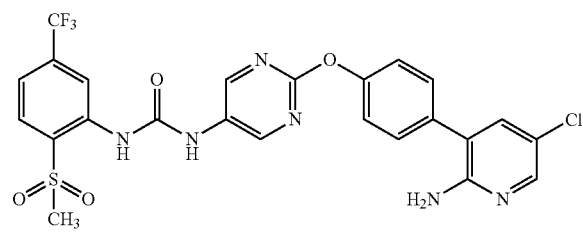

In the present invention, the 1-{2-[4-(2-amino-5-fluoropyridin-3-yl)phenoxy]pyrimidin-5-yl}-3-[2-(pyridin-3-yl)-5-(trifluoromethyl)phenyl]urea (hereinafter sometimes abbreviated as "Compound (II)") is
a compound represented by the following structural formula:

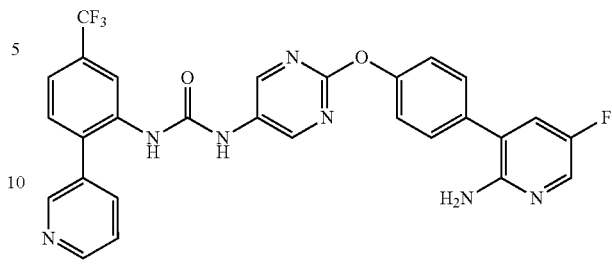

In the present invention, the 1-(2-(1H-pyrazol-1-yl)-5-(trifluoromethyl)phenyl)-3-(2-(4-(2-amino-5-chloropyridin-3-yl)phenoxy)pyrimidin-5-yl)urea (hereinafter sometimes abbreviated as "Compound (III)") is
a compound represented by the following structural formula:

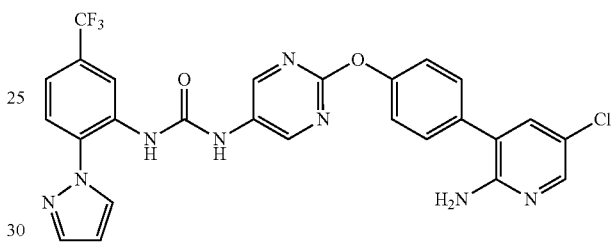

In the present invention, examples of the acid addition salt may include inorganic acid salts, such as hydrochlorides, hydrobromides, hydroiodides, sulfates, phosphates, nitrates, etc.; and organic acid salts, such as acetates, lactates, tartrates, benzoates, citrates, trifluoroacetates, glucoronates, gluconates, maleates, oxalates, maleates, aliphatic sulfonates, aromatic sulfonates, alkanol sulfonates, camphor sulfonates, etc. Examples of the aliphatic sulfonate may include methanesulfonates (MsOH salts), ethanesulfonates, propanesulfonates, butanesulfonates, pentanesulfonates, hexanesulfonates, decanesulfonates, dodecanesulfonates, 1,2-ethanedisulfonates, and the like. Examples of the aromatic sulfonate may include benzenesulfonates (BsOH salts), o-toluenesulfonates (o-TsOH salts), m-toluenesulfonates (m-TsOH salts), p-toluenesulfonates (p-TsOH salts), 1-naphthalenesulfonates, 2-naphthalenesulfonates, o-phenolsulfonates, m-phenolsulfonates, p-phenolsulfonates, naphtholsulfonates, xylenesulfonates, nitrobenzenesulfonates, sulfobenzoates, sulfosalicylates, benzaldehydesulfonates, and the like. Examples of the alkanol sulfonate may include isethionates (2-hydroxyethane-1-sulfonates), 2-hydroxypropane-1-sulfonates, 1-hydroxypropane-2-sulfonates, 3-hydroxypropane-1-sulfonates, 2-hydroxybutane-1-sulfonates, 4-hydroxybutane-1-sulfonates, 2-hydroxypentane-1-sulfonates, 2-hydroxyhexane-1-sulfonates, 2-hydroxydecane-1-sulfonates, 2-hydroxydodecane-1-sulfonates, and the like. Preferred are hydrochlorides, hydrobromides, acetates, maleates, oxalates, maleates, methanesulfonates, ethanesulfonates, isethionates, 1,2-ethanedisulfonates, camphor sulfonates, benzenesulfonates, p-toluenesulfonates, and 2-naphthalenesulfonates. More preferred are hydrochlorides, hydrobromides, methanesulfonates, benzenesulfonates, and p-toluenesulfonates.

In the present invention, the present compound may be converted into a solvate. It is preferred that the solvate is non-toxic and water-soluble. Examples of the solvate which is suitable may include solvates with water- or alcohol-based solvent (for example, ethanol, etc.).

In addition, the atoms constituting the present compound may be respectively substituted with isotopes thereof (for example, $^2$H, $^3$H, $^{13}$C, $^{14}$C, $^{15}$N, $^{16}$N, $^{17}$O, $^{18}$O, $^{18}$F, etc.), if desired.

In the present invention, the present compound is not restricted by the kind of its crystal form and may be either a crystal or an amorphous material. Alternatively, the compound may also be a mixture of a crystal and an amorphous material in an optional proportion. More preferred is a crystal. What crystal form does the present compound take may be decided by a known analysis method adopted for crystallographic analysis, for example, powder X-ray diffraction spectrum method, differential scanning calorimetry, infrared absorption spectrum method, melting point measurement method, or the like either singly or in combination.

All isomers are encompassed by the present invention unless specifically stated. For example, rotational isomers and mixtures thereof with any proportions are all encompassed by the present invention. In addition, isomers due to tautomerism are all encompassed by the present invention, too.

A crystal of 1-{2-[4-(2-amino-5-fluoropyridin-3-yl)phenoxy]pyrimidin-5-yl}-3-[2-(pyridin-3-yl)-5-(trifluoromethyl)phenyl]urea di(p-toluenesulfonate) is characterized by, for example, in an analysis by the powder X-ray diffraction spectrum method, having at least two or more (further three or more, still further four or more, and especially five or more) peaks at 2θ selected from about 6.11, 6.29, 7.76, 9.65, 10.18, 12.30, 12.57, 13.23, 13.59, 14.05, 14.85, 15.47, 16.94, 17.98, 18.52, 18.79, 19.32, 20.58, 21.25, 21.55, 22.11, 22.73, 23.20, and 24.36, preferably having peaks at 2θ of about 9.65, 22.11, and 23.20, more preferably having peaks at 2θ of about 6.11, 6.29, 7.76, 9.65, 10.18, 12.30, 12.57, 13.23, 13.59, 14.05, 14.85, 15.47, 16.94, 17.98, 18.52, 18.79, 19.32, 20.58, 21.25, 21.55, 22.11, 22.73, 23.20, and 24.36, still more preferably exhibiting the data described in Table 1 regarding Example 1 as described later, and especially preferably exhibiting data substantially identical with those in the powder X-ray diffraction spectrum chart shown in FIG. 5.

A crystal of 1-{2-[4-(2-amino-5-fluoropyridin-3-yl)phenoxy]pyrimidin-5-yl}-3-[2-(pyridin-3-yl)-5-(trifluoromethyl)phenyl]urea dibenzenesulfonate is characterized by, for example, in an analysis by the powder X-ray diffraction spectrum method, having at least two or more (further three or more, still further four or more, and especially five or more) peaks at 2θ selected from about 5.99, 6.71, 7.78, 10.08, 10.42, 11.93, 12.53, 12.96, 13.41, 14.15, 15.16, 15.55, 16.03, 16.93, 17.52, 17.95, 18.63, 18.91, 19.50, 20.18, 20.73, 21.43, 22.43, 22.84, 23.60, and 23.97, preferably having peaks at 2θ of about 20.18 and 23.97, more preferably having peaks at 2θ of about 5.99, 6.71, 7.78, 10.08, 10.42, 11.93, 12.53, 12.96, 13.41, 14.15, 15.16, 15.55, 16.03, 16.93, 17.52, 17.95, 18.63, 18.91, 19.50, 20.18, 20.73, 21.43, 22.43, 22.84, 23.60, and 23.97, still more preferably exhibiting the data described in Table 2 regarding Example 2 as described later, and especially preferably exhibiting data substantially identical with those in the powder X-ray diffraction spectrum chart shown in FIG. 6.

A crystal of 1-{2-[4-(2-amino-5-fluoropyridin-3-yl)phenoxy]pyrimidin-5-yl}-3-[2-(pyridin-3-yl)-5-(trifluoromethyl)phenyl]urea dimethanesulfonate is characterized by, for example, in an analysis by the powder X-ray diffraction spectrum method, having at least two or more (further three or more, still further four or more, and especially five or more) peaks at 2θ selected from about 5.30, 5.93, 8.91, 9.34, 9.64, 10.55, 11.77, 12.52, 12.92, 13.72, 14.25, 15.47, 15.91, 16.87, 17.87, 18.77, 19.30, 19.62, 20.77, 21.23, 21.61, 22.47, 23.36, 23.78, and 24.51, preferably having peaks at 2θ of about 10.55, 11.77, and 15.91, more preferably having peaks at 2θ of about 5.30, 5.93, 8.91, 9.34, 9.64, 10.55, 11.77, 12.52, 12.92, 13.72, 14.25, 15.47, 15.91, 16.87, 17.87, 18.77, 19.30, 19.62, 20.77, 21.23, 21.61, 22.47, 23.36, 23.78, and 24.51, still more preferably exhibiting the data described in Table 3 regarding Example 3 as described later, and especially preferably exhibiting data substantially identical with those in the powder X-ray diffraction spectrum chart shown in FIG. 7.

A crystal of 1-{2-[4-(2-amino-5-fluoropyridin-3-yl)phenoxy]pyrimidin-5-yl}-3-[2-(pyridin-3-yl)-5-(trifluoromethyl)phenyl]urea dihydrochloride is characterized by, for example, in an analysis by the powder X-ray diffraction spectrum method, having at least two or more (further three or more, still further four or more, and especially five or more) peaks at 2θ selected from about 6.03, 6.84, 8.30, 9.87, 12.52, 13.70, 13.93, 14.90, 15.88, 18.31, 19.81, 20.94, 22.47, 22.89, and 24.08, preferably having peaks at 2θ of about 8.30, 15.88, and 19.81, more preferably having peaks at 2θ of about 6.03, 6.84, 8.30, 9.87, 12.52, 13.70, 13.93, 14.90, 15.88, 18.31, 19.81, 20.94, 22.47, 22.89, and 24.08, still more preferably exhibiting the data described in Table 4 regarding Example 4 as described later, and especially preferably exhibiting data substantially identical with those in the powder X-ray diffraction spectrum chart shown in FIG. 8.

1-(2-(1H-pyrazol-1-yl)-5-(trifluoromethyl)phenyl)-3-(2-(4-(2-amino-5-chloropyridin-3-yl)phenoxy)pyrimidin-5-yl)urea p-toluenesulfonate is characterized by, for example, in an analysis by the powder X-ray diffraction spectrum method, exhibiting data substantially identical with those in the powder X-ray diffraction spectrum chart shown in FIG. 9.

1-(2-(1H-pyrazol-1-yl)-5-(trifluoromethyl)phenyl)-3-(2-(4-(2-amino-5-chloropyridin-3-yl)phenoxy)pyrimidin-5-yl)urea benzenesulfonate is characterized by, for example, in an analysis by the powder X-ray diffraction spectrum method, exhibiting data substantially identical with those in the powder X-ray diffraction spectrum chart shown in FIG. 10.

A crystal of 1-(2-(1H-pyrazol-1-yl)-5-(trifluoromethyl)phenyl)-3-(2-(4-(2-amino-5-chloropyridin-3-yl)phenoxy)pyrimidin-5-yl)urea methanesulfonate is characterized by, for example, in an analysis by the powder X-ray diffraction spectrum method, having at least two or more (further three or more, still further four or more, and especially five or more) peaks at 2θ selected from about 5.42, 8.64, 8.97, 9.64, 10.39, 11.85, 13.13, 16.02, 16.27, 16.89, 17.39, 18.19, 19.53, 20.49, 20.83, 21.89, 22.59, and 23.90, preferably having peaks at 2θ of about 5.42, 8.64, 8.97, 9.64, 10.39, 11.85, 13.13, 16.02, 16.27, 16.89, 17.39, 18.19, 19.53, 20.49, 20.83, 21.89, 22.59, and 23.90, more preferably exhibiting the data described in Table 5 regarding Example 7 as described later, and still more preferably exhibiting data substantially identical with those in the powder X-ray diffraction spectrum chart shown in FIG. 11.

A crystal of 1-(2-(1H-pyrazol-1-yl)-5-(trifluoromethyl)phenyl)-3-(2-(4-(2-amino-5-chloropyridin-3-yl)phenoxy)pyrimidin-5-yl)urea hydrochloride is characterized by, for example, in an analysis by the powder X-ray diffraction spectrum method, having at least two or more (further three or more, still further four or more, and especially five or more) peaks at 2θ selected from about 5.63, 10.37, 10.73, 11.29, 12.30, 12.73, 13.68, 14.03, 14.53, 16.07, 16.64, 17.93, 18.66, 18.91, 19.89, 20.76, 21.35, 22.52, 22.84, 24.33, and 24.74, preferably having peaks at 2θ of about 5.63, 10.37, 10.73, 11.29, 12.30, 12.73, 13.68, 14.03, 14.53, 16.07, 16.64, 17.93, 18.66, 18.91, 19.89, 20.76, 21.35, 22.52, 22.84, 24.33, and 24.74, more preferably exhibiting the data described in Table 6 regarding Example 8 as described later, and still more preferably exhibiting data substantially identical with those in the powder X-ray diffraction spectrum chart shown in FIG. 12.

A crystal of 1-{2-[4-(2-amino-5-chloro-3-pyridinyl)phenoxy]-5-pyrimidinyl}-3-[2-(methylsulfonyl)-5-(trifluoromethyl)phenyl]urea p-toluenesulfonate is characterized by, for example, in an analysis by the powder X-ray diffraction spectrum method, having at least two or more (further three or more, still further four or more, and especially five or more) peaks at 2θ selected from about 6.35, 7.74, 9.98, 11.08, 11.42, 12.68, 13.22, 14.83, 15.42, 15.98, 16.89, 17.33, 17.86, 18.29, 19.00, 19.46, 20.56, 20.92, 21.47, 22.04, 23.82, and 24.49, preferably having peaks at 2θ of about 6.35, 7.74, 9.98, 11.08, 11.42, 12.68, 13.22, 14.83, 15.42, 15.98, 16.89, 17.33, 17.86, 18.29, 19.00, 19.46, 20.56, 20.92, 21.47, 22.04, 23.82, and 24.49, more preferably exhibiting the data described in Table 7 regarding Example 9 as described later, and still more preferably exhibiting data substantially identical with those in the powder X-ray diffraction spectrum chart shown in FIG. 1.

A crystal of 1-{2-[4-(2-amino-5-chloro-3-pyridinyl)phenoxy]-5-pyrimidinyl}-3-[2-(methylsulfonyl)-5-(trifluoromethyl)phenyl]urea benzenesulfonate is characterized by, for example, in an analysis by the powder X-ray diffraction spectrum method, having at least two or more (further three or more, still further four or more, and especially five or more) peaks at 2θ selected from about 6.77, 7.78, 10.26, 11.20, 11.50, 13.54, 15.65, 16.02, 17.13, 18.01, 18.41, 18.70, 19.52, 20.25, 20.64, 21.65, 21.95, 22.66, 23.49, and 24.57, preferably having peaks at 2θ of about 6.77, 7.78, 10.26, 11.20, 11.50, 13.54, 15.65, 16.02, 17.13, 18.01, 18.41, 18.70, 19.52, 20.25, 20.64, 21.65, 21.95, 22.66, 23.49, and 24.57, more preferably exhibiting the data described in Table 8 regarding Example 10 as described later, and still more preferably exhibiting data substantially identical with those in the powder X-ray diffraction spectrum chart shown in FIG. 2.

A crystal of 1-{2-[4-(2-amino-5-chloro-3-pyridinyl)phenoxy]-5-pyrimidinyl}-3-[2-(methylsulfonyl)-5-(trifluoromethyl)phenyl]urea methanesulfonate is characterized by, for example, in an analysis by the powder X-ray diffraction spectrum method, having at least two or more (further three or more, still further four or more, and especially five or more) peaks at 2θ selected from about 4.63, 7.04, 9.33, 14.11, 18.74, 20.43, 21.35, 23.31, and 24.80, preferably having peaks at 2θ of about 4.63, 7.04, 9.33, 14.11, 18.74, 20.43, 21.35, 23.31, and 24.80, more preferably exhibiting the data described in Table 9 regarding Example 11 as described later, and still more preferably exhibiting data substantially identical with those in the powder X-ray diffraction spectrum chart shown in FIG. 3.

A crystal of 1-{2-[4-(2-amino-5-chloro-3-pyridinyl)phenoxy]-5-pyrimidinyl}-3-[2-(methylsulfonyl)-5-(trifluoromethyl)phenyl]urea hydrochloride is characterized by, for example, in an analysis by the powder X-ray diffraction spectrum method, having at least two or more (further three or more, still further four or more, and especially five or more) peaks at 2θ selected from about 4.60, 5.95, 7.06, 7.75, 9.38, 10.19, 11.82, 12.21, 13.01, 15.27, 17.81, 18.49, 18.79, 19.89, 20.52, 21.12, 21.96, 22.51, 23.67, and 24.54, preferably having peaks at 2θ of about 4.60, 5.95, 7.06, 7.75, 9.38, 10.19, 11.82, 12.21, 13.01, 15.27, 17.81, 18.49, 18.79, 19.89, 20.52, 21.12, 21.96, 22.51, 23.67, and 24.54, more preferably exhibiting the data described in Table 10 regarding Example 12 as described later, and still more preferably exhibiting data substantially identical with those in the powder X-ray diffraction spectrum chart shown in FIG. 4.

Although the crystal form of the present compound is specified by the physicochemical properties disclosed in the present specification, the respective data may be slightly variable from the standpoints of properties thereof, and the crystal form should not be strictly comprehended.

Data obtained by, for example, the powder X-ray diffraction spectrum method, for example, a relative intensity may be variable from the standpoints of properties thereof according to direction of crystal growth, grain size, measurement conditions, and so on. Thus, in determining the identity of crystal form, a diffraction angle (2θ) or an overall diffraction pattern is important. In addition, in determining the identity of crystal form, a half width may be read from a powder X-ray diffraction spectrum chart and used in combination with a diffraction angle (2θ) or an overall diffraction pattern or relative intensity, if desired.

In general, a measurement error of the diffraction angle (2θ) in the powder X-ray diffraction spectrum is, for example, generated due to the kind of measurement instrument, a sampling state of the compound to be measured, and so on.

Accordingly, all compounds in which an overall diffraction pattern of data obtained by the powder X-ray diffraction spectrum method is analogous to that of the crystal form of the present compound disclosed in the present specification are encompassed in the present invention.

While a person skilled in the art may easily understand, in the present specification, the powder X-ray diffraction spectrum charts described in the drawings as described later are one in which the diffraction angle 2 θ (degree) is indicated on the abscissa (2-Theta-Scale), and the diffraction intensity is indicated on the ordinate (Lin (Counts)).

In the present specification, the powder X-ray diffraction spectrum is one measured using a Cu-Kα ray.

[Toxicity]
The present compound has low toxicity and thus can be used with safe (for example, it does not have a drug interaction, or the like) as a medicament.

[Application to Medicaments]
The present compound exhibits Trk-inhibiting activity and thus is useful as a prophylactic and/or therapeutic agent for Trk-related diseases, for example, pain, pruritus, lower urinary tract dysfunction, asthma, allergic rhinitis, inflammatory bowel disease, Chagas disease, cancer, etc.

More specifically, examples of the pain may include pain of osteoarthritis, cancer pain, chronic low back pain, low back pain of osteoporosis, pain of bone fracture, pain of rheumatoid arthritis, neuropathic pain, postherpetic pain, pain of diabetic neuropathy, fibromyalgia, pain of pancreatitis, pain of interstitial cystitis, pain of endometriosis, pain of irritable bowel syndrome, migraine, postoperative pain, pain of pulpitis, and the like. Examples of the pruritus may include systemic cutaneous pruritus, localized cutaneous pruritus, senile cutaneous pruritus, gestational pruritus, pruritus ani, vulvar pruritus, and the like. Examples of the lower urinary tract dysfunction may include interstitial cystitis, difficulty of urination, bladder neck obstruction, bladder neck contracture, urethral syndrome, detrusor sphincter dyssynergia, unstable bladder, chronic prostatitis, chronic cystitis, psychogenic cystitis, drug-induced dysuria, Hinman syndrome, Fowler syndrome, and the like. Examples of the inflammatory bowel disease may include ulcerative colitis, Crohn's disease, and the like. Examples of the cancer may include breast cancer, ovarian cancer, large bowel cancer (for example, colon cancer, etc.), lung cancer (for example, non-small cell lung cancer, etc.), prostate cancer, head and neck cancer (for example, oral squamous cell carcinoma, squamous cell carcinoma of the head and neck, pharyngeal cancer, laryngeal cancer, tongue cancer, thyroid cancer, acoustic neuroma, etc.), skin cancer (for example, melanoma (malignant melanoma), etc.), lymphoma (for example, B-cell lymphoma, T-cell lymphoma, etc.), brain tumor, nerve glioma, pituitary adenoma, uveal malignant melanoma, meningioma, thymoma, mesothelioma, esophageal cancer, stomach cancer, liver cancer (for example, hepatocellular carcinoma, etc.), cholangiocarcinoma, gallbladder cancer, pancreatic cancer, kidney cancer (for example, renal cell carcinoma, renal pelvis ureter cancer, etc.), bladder cancer, penile cancer, testicular cancer, uterine cancer, vaginal cancer, vulvar cancer, malignant bone tumor, soft tissue sarcoma, chondrosarcoma, leukemia, myelodysplastic syndrome, multiple myeloma, salivary gland tumor, neuroendocrine tumor, neuroblastoma, pulmonary sarcoma, medulloblastoma, glioblastoma, retinoblastoma, osteosarcoma, small intestinal cancer, adrenal cortical carcinoma, and the like.

The present compound is particularly useful as a prophylactic and/or therapeutic agent for pain or cancer.

The present compound may be administered as a combination drug with other drug in order to:

(1) complement and/or enhance the prophylactic and/or therapeutic effect of the compound;

(2) improve the kinetics and absorption and reduce the dosage of the compound; and/or (3) alleviate the side effect of the compound.

The combination drug of the present compound and other drug may be administered in the form of one formulation containing both components or may be administered as separate formulations. Administration of separate formulations includes simultaneous administration and sequential administration. In addition, in the sequential administration, the present compound may be first administered, followed by administering other drug, or other drug may be first administered, followed by administering the present compound. The respective manners of administration may be the same as or different from each other.

The drug for which the combination drug exhibits the prophylactic and/or therapeutic effect is not particularly limited and has only to be a drug which complements and/or enhances the prophylactic and/or therapeutic effect of the present compound.

Examples of the other drug for complementing and/or enhancing the prophylactic and/or therapeutic effect of the present compound for pain may include acetaminophen, a nonsteroid antiinflammatory drug, an opioid, an antidepressant, an antiepileptic agent, an N-methyl-D-aspartate antagonist, a muscle relaxant, an antiarrhythmic agent, a steroid, a bisphosphonate, and the like.

Examples of the nonsteroid antiinflammatory drug may include sasapyrine, sodium salicylate, aspirin, aspirin formulations, such as those containing aspirin-dialuminate, etc., diflunisal, indomethacin, suprofen, ufenamate, dimethylisopropylazulene, bufexamac, felbinac, diclofenac, tolmetin sodium, Clinoril, fenbufen, nabumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, Tiaprofen, oxaprozin, pranoprofen, loxoprofen sodium, alminoprofen, zaltoprofen, mefenamic acid, aluminum mefenamate, tolfenamic acid, floctafenine, ketophenylbutazone, oxyphenbutazone, piroxicam, tenoxicam, ampiroxicam, Napageln ointment, epirizole, tiaramide hydrochloride, tinoridine hydrochloride, emorfazone, sulpyrine, Migrenin, Saridon, Sedes G, Amipylo-N, Sorbon, pilin-based cold remedies, acetaminophen, phenacetin, dimetotiazine mesilate, meloxicam, celecoxib, rofecoxib, valdecoxib, simetride-containing formulations, non-pilin-based cold remedies, and the like.

Examples of the opioid may include codeine, fentanyl, hydromorphone, levorphanol, meperidine, methadone, morphine, oxycodone, oxymorphone, propoxyphene, hydrocodone, tramadol, buprenorphine, tapentadol, pentazocine, butorphanol, and the like.

Examples of the antidepressant may include tricyclic antidepressants (for example, amitriptyline hydrochloride, imipramine hydrochloride, clomipramine hydrochloride, dosulepin hydrochloride, nortriptyline hydrochloride, lofepramine hydrochloride, trimipramine maleate, and amoxapine), tetracyclic antidepressants (for example, maprotiline hydrochloride, mianserin hydrochloride, and setiptiline maleate), monoamine oxidase (MAO) inhibitors (for example, safrazine hydrochloride), serotonin and noradrenaline reuptake inhibitors (SNRIs) (for example, milnacipran hydrochloride and venlafaxine hydrochloride), selective serotonin reuptake inhibitors (SSRIs) (for example, fluvoxamine maleate, paroxetine hydrochloride, fluoxetine hydrochloride, and citalopram hydrochloride), serotonin reuptake inhibitors (for example, trazodone hydrochloride), and the like.

Examples of the antiepileptic agent may include phenobarbital, Puridomin, phenytoin, ethosuximide, zonisamide, nitrazepam, clonazepam, carbamazepine, sodium valproate, acetazolamide, sulthiame, and the like.

Examples of the N-methyl-D-aspartate antagonist may include ketamine hydrochloride, amantadine hydrochloride, memantine hydrochloride, dextromethorphan, methadone, and the like.

Examples of the muscle relaxant may include succinylcholine, suxamethonium, vecuronium bromide, pancronium bromide, dantrolene sodium, and the like.

Examples of the antiarrhythmic agent may include procainamide, disopyramide, cibenzoline, pirmenol, lidocaine, mexiletine, aprindine, pilsicainide, flecainide, propafenone, propranolol, atenolol, bisoprolol, amiodarone, sotalol, verapamil, diltiazem, bepridil, and the like.

Examples of the steroid may include, as external medicines, clobetasol propionate, diflorasone diacetate, fluocinonide, mometasone furoate, betamethasone dipropionate, betamethasone butyrate propionate, betamethasone valerate, difluprednate, pudesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, peclometasone propionate, triamcinolone acetonide, flumethasone pivalate, alclometasone dipropionate, clobetasone butyrate, prednisolone, beclomethasone propionate, fludroxycortide, and the like.

As medicines for internal use or for injection, there may be included cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, betamethasone, and the like.

As inhalants, there may be included beclomethasone propionate, fluticasone propionate, budesonide, flunisolide, triamcinolone, ST-126P, ciclesonide, dexamethasone palmitate, mometasone furoate, prasterone sulfonate, deflazacort, methylprednisolone suleptanate, methylprednisolone sodium succinate, and the like.

Examples of the bisphosphonate may include etidronate, pamidronate, alendronate, risedronate, zoledronate, minodronate, and the like.

Examples of the other drug for complementing and/or enhancing the prophylactic and/or therapeutic effect of the present compound for cancer may include an alkylating agent, a metabolic antagonist, an anticancer antibiotics, an anticancer vegetable preparation, a hormone drug, a platinum compound, a topoisomerase inhibitor, a kinase inhibitor, an anti-CD20 antibody, an anti-HER2 antibody, an anti-EGFR antibody, an anti-VEGF antibody, a proteasome inhibitor, an HDAC inhibitor, an immune checkpoint inhibitor (for example, an anti-CTLA-4 antibody, an anti-PD-1 antibody, an anti-PD-L1 antibody, etc.), an immunomodulatory, other anticancer drugs, and the like.

Examples of the alkylating agent may include cyclophosphamide, ifosfamide, dacarbazine, nimustine hydrochloride, ranimustine, bendamustine, thiotepa, carboquone, and the like.

Examples of the metabolic antagonist may include methotrexate, pemetrexed, fluorouracil, tegafur, tegafur uracil, tegafur gimestat otastat potassium, doxifluridine, capecitabine, cytarabine, gemcitabine hydrochloride, fludarabine, nelarabine, carmofur, procarbazine hydrochloride, and the like.

Examples of the anticancer antibiotics may include mitomycin C, doxorubicin hydrochloride, aclarubicin hydrochloride, pirarubicin hydrochloride, epirubicin, chromomycin A3, bleomycin, peplomycin sulfate, therarubicin, and the like.

Examples of the anticancer vegetable preparation may include irinotecan hydrochloride, etoposide, vincristine sulfate, vinblastine sulfate, vindesine sulfate, vinorelbine ditartrate, docetaxel hydrate, eribulin mesylate, paclitaxel, and the like.

Examples of the hormone drug may include estramustine phosphate sodium, flutamide, bicalutamide, goserelin acetate, leuprorelin acetate, tamoxifen citrate, toremifene citrate, anastrozole, letrozole, exemestane, mepitiostane, medroxyprogesterone acetate, epitiostanol, fosfestrol, fadrozole hydrochloride hydrate, abiraterone, fulvestrant, aminoglutethimide, and the like.

Examples of the platinum compound may include carboplatin, cisplatin, nedaplatin, oxaliplatin, and the like.

Examples of the topoisomerase inhibitor may include topotecan, sobuzoxane, and the like.

Examples of the kinase inhibitor may include, as an EGFR inhibitor, erlotinib, gefitinib, and afatinib; as an HER2 inhibitor, lapatinib; as a BCR-ABL inhibitor, imatinib; as an ALK inhibitor, crizotinib; as a multikinase inhibitor, regorafenib and dasatinib; and the like.

Examples of the anti-CD20 antibody may include rituximab, ibritumomab, ibritumomab tiuxetan, ocrelizumab, and the like.

Examples of the anti-HER2 antibody may include trastuzumab, trastuzumab emtansine, pertuzumab, and the like.

Examples of the anti-EGFR antibody may include cetuximab, panitumumab, and the like.

Examples of the anti-VEGF antibody may include bevacizumab and the like.

Examples of the proteasome inhibitor may include bortezomib and the like.

Examples of the HDAC inhibitor may include vorinostat and the like.

Examples of the anti-CTLA-4 antibody may include ipilimumab and the like.

Examples of the anti-PD-1 antibody may include nivolumab, pembrolizumab, and the like.

Examples of the anti-PD-L1 antibody may include atezolizumab, avelumab, and the like.

Examples of the immunomodulatory include thalidomide, lenalidomide, pomalidomide, and the like.

A mass ratio of the present compound and other drugs is not particularly limited.

Any combination of two or more kinds of other drugs may be administered.

In addition, other drugs for complementing and/or enhancing the prophylactic and/or therapeutic effect of the present compound may encompass not only those which have been identified to date but also those which will be identified in the future based on the above mechanism.

The present compound or the combination drug of the present compound and other drug, which is used for the above-described purpose is generally formulated as an appropriate pharmaceutical composition together with a pharmaceutically acceptable carrier and then administered systemically or topically by oral or parenteral administration.

The dosage may vary according to age, weight, symptoms, therapeutic effect, mode of administration, treatment period, and the like and may be one to several oral administrations a day within the range of 1 mg to 1,000 mg per dose per adult or one to several parenteral administrations a day within the range of 0.1 mg to 100 mg per dose or intravenous continuous administration for 1 hour to 24 hours a day per adult.

As a matter of course, as described above, the dosage may vary according to various conditions, and thus, the sufficient dosage may be lower than the above-described amount, or the amount higher than the above-described amount may be required.

The present compound or the combination drug of the present compound and other drugs may be administered as an oral solid dosage form for internal use, an internal liquid medicine or an injection, an external medicine, a suppository, an ophthalmic solution, an inhalation, or the like for parenteral administration.

Examples of the oral solid dosage form for internal use may include a tablet, a pill, a capsule, a powder, a granule, and the like. Examples of the capsule may include a hard capsule and a soft capsule. In addition, examples of the tablet may include a sublingual tablet, an oral patch, an orally disintegrating tablet, and the like.

In the solid dosage form for internal use, one or more active substances per se may be formulated or may be formulated after mixing thereof with an excipient (e.g., lactose, mannitol, glucose, microcrystalline cellulose, starch, etc.), a binder (e.g., hydroxypropyl cellulose, polyvinylpyrrolidone, magnesium aluminate metasilicate, etc.), a disintegrant (e.g., calcium cellulose glycolate, etc.), a lubricant (e.g., magnesium stearate, etc.), a stabilizer, a solution adjuvant (e.g., glutamic acid, aspartic acid, etc.), or the like according to conventional methods. In addition, the solid dosage form may be optionally coated with a coating agent (e.g., sucrose, gelatin, hydroxypropyl cellulose, hydroxypropyl methylcellulose phthalate, etc.) and may be coated in two or more layers. The solid dosage form may further encompass a capsule of an absorbable substance, such as gelatin.

Examples of the internal liquid medicine may include a pharmaceutically acceptable water, a suspension, an emulsion, a syrup, an elixir, and the like. In the liquid medicine, one or more active substances are dissolved, suspended, or emulsified in a diluent of general use (e.g., purified water, ethanol, a mixed solution thereof, etc.). The liquid medicine may further contain a wetting agent, a suspending agent, an emulsifying agent, a sweetening agent, a flavoring agent, an aroma, a preservative, a buffering agent, and so on.

Examples of the dosage form of the external medicine for parenteral administration may include an ointment, a gel, a cream, a cataplasm, a plaster and pressure-sensitive adhesive, a liniment, an atomized agent, an inhalation, a spray, an aerosol, an ophthalmic solution, a nasal solution, and the like. The dosage forms contain one or more active substances and may be prepared according to a known method or a formulation generally used.

The atomized agent, the inhalation, or the spray may contain, in addition to a diluent that is generally used, a stabilizer, such as sodium hydrogen sulfite, and a buffering agent capable of conferring isotonicity, for example, sodium chloride, sodium citrate, an isotonicity agent, such as citric acid, or the like. A method of producing a spray is specifically described in, for example, U.S. Pat. Nos. 2,868,691 and 3,095,355.

The injection for parenteral administration may encompass injections in the form of a solution, a suspension, an emulsion, or a solid to be dissolved or suspended in a solvent upon use. The injection may be used by dissolving, suspending, or emulsifying one or more active substances in a solvent. As the solvent, there may be, for example, used distilled water for injection, saline, vegetable oil, propylene glycol, polyethylene glycol, an alcohol, such as ethanol, or a combinations thereof. The injection may further contain a stabilizer, a solution adjuvant (e.g., glutamic acid, aspartic acid, Polysorbate 80 (registered trademark), etc.), a suspending agent, an emulsifying agent, a soothing agent, a buffering agent, a preservative, or the like. The injection may be produced by sterilization in a final step or through an aseptic operation. In addition, an aseptic solid agent, for example, a lyophilized product may be produced and dissolved in sterilized or aseptic distilled water or other solvent for injection before use.

Examples of other composition for parenteral administration may include a suppository for rectal administration and a pessary for vaginal administration, each of which contains one or more active substances and is formulated according to a conventional method, and the like.

In the present invention, "an article of manufacture" comprises (1) a pharmaceutical composition including the present compound or a pharmaceutical composition in the form of a combination drug including the present compound with a concomitant drug other than the present compound, (2) a container containing the above-described composition, and (3) at least one of an instruction, a description, a package insert, and a product label (including those corresponding to a label or a labeling in the United States), all of which indicate that the composition can be used for prophylaxis and/or therapy of a Trk-related disease optionally in combination with an appropriate concomitant drug (preferably acetaminophen, a nonsteroid antiinflammatory drug, an opioid, an antidepressant, an antiepileptic agent, an N-methyl-D-aspartate antagonist, a muscle relaxant, an antiarrhythmic agent, a steroid, and/or a bisphosphonate; or an alkylating agent, a metabolic antagonist, an anticancer antibiotics, an anticancer vegetable preparation, a hormone drug, a platinum compound, a topoisomerase inhibitor, a kinase inhibitor, an anti-CD20 antibody, an anti-HER2 antibody, an anti-EGFR antibody, an anti-VEGF antibody, a proteasome inhibitor, an HDAC inhibitor, an immune checkpoint inhibitor, and/or an immunomodulatory; or the like).

The package insert as referred to herein means an official document attached to a medicament which provides necessary information for appropriate use of the medicament and corresponds to "Tenpu Bunsho" (also referred to as "Nougaki") in accordance with the Pharmaceutical Affairs Act in Japan, "Summary of Product Characteristics (SPC or SmPC)" in accordance with Directive in EU, "US Package Insert (USPI)" in accordance with Federal Regulations in the United States and equivalent documents elsewhere.

The information provided by these documents is specifically prescribed by Articles 52, 54, and 68(4), and the like in the Pharmaceutical Affairs Act (see, if necessary, Notification Nos. 606 and 607 of Pharmaceutical Affairs Bureau as of Apr. 25, 1997 and/or related notifications, or the like) for "Tenpu Bunsho" in Japan, by Directive 2001/83/EC Article 11 and the like (see, if necessary, A guideline on SmPC and/or related guidelines) for Summary of Product Characteristics in EU, and by 21 CFR 201.100 and the like (see, if necessary, 21 CFR 201.57 and/or related Federal Regulations) for US Package Insert in the United States and generally includes information on indications, dosage and administration, method of administration, warnings and/or contraindications.

In the United States, 21 CFR 201 Subpart B requires that in addition to the US Package Insert, a label or a labeling (or labelling) should contain a part or all information provided on the US Package Insert. A label herein means the one directly provided on a container and a labeling means the concept encompassing the label, printing on packages, and printed matters attached to articles of manufacture.

In the present invention, the term "container" means the one which directly accommodates the pharmaceutical composition comprising the present compound or the pharmaceutical composition in the form of a combination drug including the present compound with a concomitant drug other than the present compound and may also be referred to as "an immediate container", "an immediate wrapper", "an inner seal" or the like. Examples of the container may include cans/tins, bottles, boxes, ampoules, vials, tubes, unit dose containers for eye drops, paper, cloth, plastics, plastic bags, SP sheets, PTP sheets, plastic containers, and the like.

The container containing the pharmaceutical composition therein is combined with at least one of an instruction, a description, a package insert, and a product label (including the one corresponding to a label or labeling in the United Stated) as described above and may be generally packaged in an outer container or an outer wrapper and distributed to the market.

In addition, the present invention also discloses a method for advertisement of a pharmaceutical composition comprising the present compound or a pharmaceutical composition in the form of a combination drug including the present compound with a concomitant drug, the method including encouraging a target viewer to use the composition for prophylaxis and/or therapy of a Trk-related disease.

The above-described method involves publicly distributing information that describes the value, particularly a health benefit of using, in prophylaxis and/or therapy for a Trk-related disease, the pharmaceutical composition including the present compound or the pharmaceutical composition in the form of the combination drug including the present compound with another concomitant drug. Such information is distributed through an appropriate advertising medium in addition to verbal communication. The advertising medium may be any of newspaper, magazines, television, radio, video, brochures, leaflets, posters, social networking systems, e-mail, electronic signboards, digital signage, internet advertisements (homepages/websites, banner advertisements and the like), outdoor advertisements (poster boards, neon signs, large screen displays and the like), transportation advertisements (advertisements suspended in trains, buses, cabs and the like, advertisements above windows and beside doors of trains, buses, cabs and the like, advertisements in stations), movie theatre slide advertisements (advertisements on screens in movie theatres), POP advertisements (advertisements at shop front and in shops), direct advertisements (direct mails, newspaper inserts, flyers), specialty advertisements (novelty advertisements such as calendars, pens and the like), other advertisements (skywriting, advertisements on benches and the like). A person skilled in the art can easily produce the advertising media.

Unless otherwise defined, all technical and scientific terms and abbreviations used herein have the same meanings as those usually understood by a person skilled in the art to which the present invention pertains.

The contents of all the Patent Documents and Non-Patent Documents or references explicitly cited herein may be entirely incorporated herein as a part of the present specification.

EXAMPLES

The present invention is hereunder described in detail by way of Examples, but it should not be construed that the present invention is limited by these Examples.

Solvents indicated in brackets described in chromatographic separation and TLC sections indicate elution solvents or development solvents used, and proportions are expressed in a volume ratio.

Each of solvents indicated in brackets described in NMR sections indicates a solvent used for measurement.

[1] LC-MS/ELSD:

The measurement was carried out under the following conditions:

{Column: Waters ACQUITY $C_{18}$ (particle diameter: 1.7×$10^{-6}$ m; column length: 30×2.1 mm I.D.); flow rate: 1.0 mL/min; column temperature: 40° C.; mobile phase (A): 0.1% formic acid aqueous solution; mobile phase (B): 0.1% formic acid-acetonitrile solution; gradient (a ratio of the mobile phase (A) to the mobile phase (B) is described): [0 min] 95/5; [0.1 min] 95/5; [1.2 min] 5/95; [1.4 min] 5/95; [1.41 min]95/5; [1.5 min] 95/5; detector: UV(PDA), ELSD, MS}

[2] Powder X-Ray Diffraction Spectrum:
<Measurement Conditions>
Apparatus: BRUKER D8 DISCOVER with GADDS, manufactured by BRUKER axa
Target: Cu
Voltage: 40 kV
Current: 40 mA
Exposure time: 3 min

[General Synthesis Method of Acid-Addition Salts of Compound (I), Compound (II), and Compound (III)]

Using Compound (I), Compound (II), and Compound (III) and various acids, acid-addition salts were produced by the following methods. In solutions of Compound (I), Compound (II), and Compound (III) dissolved in various solvents, in the case of Compound (I) and Compound (III), equimolar equivalent of the acid was added thereto and mixed therewith, and in the case of Compound (II), two molar equivalents of the acid was added thereto and mixed therewith. A precipitated crystal was collected by means of filtration and then dried. In the case where a crystal was not precipitated, the solvent was distilled off under reduced pressure, and the residue was dried. The thus obtained crystal or amorphous material was measured with respect to physical properties data through powder X-ray diffraction spectrum, TLC, LC-MS, NMR, and so on. The physical properties data are described in detail in the following Examples.

The compounds used in the present specification were named by using a computer program generally according to IUPAC nomenclature system, ACD/Name (registered trademark), or Chemdraw Ultra (version 12.0, manufactured by Cambridge Soft), or according to IUPAC nomenclature system.

Reference Example 1

2,2,2-Trichloroethyl(2-(pyridin-3-yl)-5-(trifluoromethyl)phenyl)carbamate

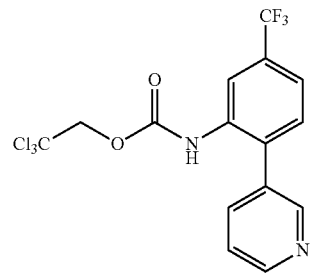

To an ethyl acetate (5.7 mL) solution of 2-(pyridin-3-yl)-5-(trifluoromethyl)benzeneamine (574 mg), sodium bicarbonate (404 mg) and 2,2,2-trichloroethyl chloroformate (398 μL) were added, followed by stirring for 30 minutes. Water was added to the reaction mixture, and the resultant was extracted with ethyl acetate. The resulting organic layer was washed with a saturated sodium chloride aqueous solution, dried over anhydrous sodium sulfate, and then concentrated under reduced pressure. The resulting residue was purified by means of silica gel chromatography (hexane/ethyl acetate=4/1), thereby obtaining the titled compound (959 mg) having the following physical properties value.

Properties: White solid

TLC:Rf 0.62 (hexane/ethyl acetate=1/1)

$^1$H-NMR (DMSO-$d_6$): δ4.82 (s, 2H), 7.44-7.52 (m, 1H), 7.64 (d, 1H), 7.73 (d, 1H), 7.75-7.88 (m, 2H), 8.55-8.65 (m, 2H), 9.83 (brs, 1H)

Reference Example 2

5-Nitro-2-(4-(4,4,5,5-tetramethyl-1,3,2-dioxaborolan-2-yl)phenoxy)pyrimidine

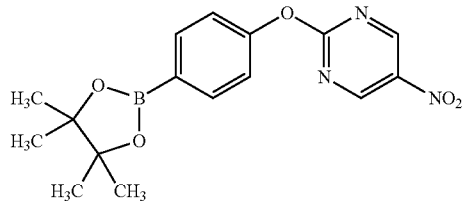

To a tetrahydrofuran (hereinafter abbreviated as "THF") (8.2 mL) solution of 4-(4,4,5,5-tetramethyl-1,3,2-dioxaborolan-2-yl)phenol (900 mg), triethylamine (0.63 mL) and 2-chloro-5-nitropyrimidine (684 mg) were added. The reaction mixture was stirred at 0° C. for one hour. The reaction mixture was diluted with ethyl acetate, and the resulting reaction mixture was washed with a saturated sodium bicarbonate aqueous solution, water, and a saturated sodium chloride aqueous solution. The resulting organic layer was dried over sodium sulfate and then concentrated under reduced pressure, thereby obtaining the titled compound (1.53 g) having the following physical properties value.

Properties: Yellow solid
TLC:Rf 0.45 (hexane/ethyl acetate=4/1)
$^1$H-NMR (CDCl$_3$): δ1.35 (s, 12H), 7.20 (d, 2H), 7.93 (d, 2H), 9.31 (s, 2H)

Reference Example 3

2-(4-(4,4,5,5-Tetramethyl-1,3,2-dioxaborolan-2-yl)phenoxy)pyridine-5-amine

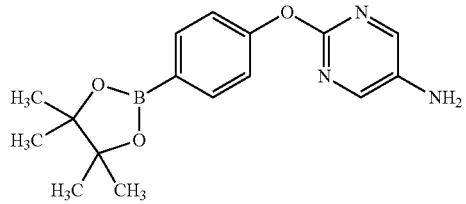 [SMILES: CC1(C)OB(c2ccc(Oc3ncc(N)cn3)cc2)OC1(C)C]

To a mixed solution of ethanol (16.7 mL) and ethyl acetate (8.4 mL) of the compound (1.52 g) produced in Reference Example 2, palladium hydroxide (20% wet, 139 mg) was added. The reaction mixture was stirred in a hydrogen atmosphere at 35° C. for 4 hours. To the resulting reaction mixture, methanol (8 mL) and activated carbon (29 mg) were added, followed by stirring at room temperature for 5 minutes. The reaction mixture was filtered by Celite (trade name), and the filtrate was concentrated. To the resulting residue, a tert-butyl methyl ether/hexane (1/1) mixed solvent was added, and the precipitated solid was collected by means of filtration, thereby obtaining the titled compound (1.14 g) having the following physical properties value.

Properties: White solid
TLC:Rf 0.29 (hexane/ethyl acetate=1/1)
$^1$H-NMR (CDCl$_3$): δ1.33 (s, 12H), 3.51 (brs, 2H), 7.14 (d, 2H), 7.85 (d, 2H), 8.06 (s, 2H)

Reference Example 4

2-(4-(2-amino-5-fluoropyridin-3-yl)phenoxy)pyrimidine-5-amine

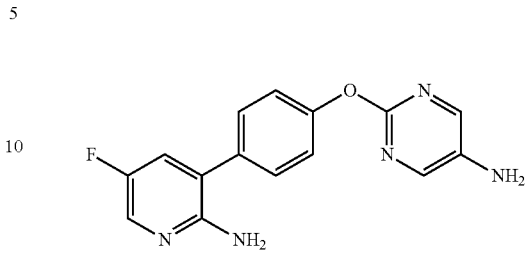

To a 1,4-dioxane (20 mL) solution of the compound (1.1 g) produced in Reference Example 3 and 2-amino-3-bromo-5-fluoropyridine (738 mg), a potassium phosphate aqueous solution (2 mol/L, 24 mL) and tetrakis(triphenylphosphine)palladium(0) (203 mg) were added in an argon atmosphere. The reaction mixture was stirred at 100° C. overnight. Water was added to the reaction mixture, and the resultant was extracted with ethyl acetate. The resulting organic layer was washed with a saturated sodium chloride aqueous solution, dried over anhydrous sodium sulfate, and then concentrated under reduced pressure. The resulting residue was washed with isopropyl alcohol and collected by means of filtration, thereby obtaining the titled compound (737 mg) having the following physical properties value.

Properties: Yellowish brown solid
TLC:Rf 0.41 (ethyl acetate)
$^1$H-NMR (DMSO-d$_6$): δ5.28 (s, 2H), 5.53 (s, 2H), 7.15 (d, 2H), 7.35 (dd, 1H), 7.48 (d, 2H), 7.93 (d, 1H), 7.99 (s, 2H)

Example 1

1-{2-[4-(2-amino-5-fluoropyridin-3-yl)phenoxy]pyrimidin-5-yl}-3-[2-(pyridin-3-yl)-5-(trifluoromethyl)phenyl]urea di(p-toluenesulfonate)

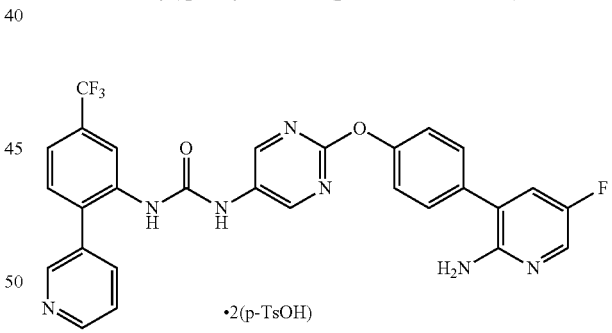

To an N,N-dimethylacetamide (hereinafter abbreviated as "DMA") (5 mL) solution of the compound (500 mg) produced in Reference Example 4 and the compound (765 mg) of the compound produced in Reference Example 1, triethylamine (0.067 mL) was added. The reaction mixture was stirred in an argon atmosphere at 70° C. for 1.5 hours. Water was added to the reaction mixture, and the reaction mixture was extracted with ethyl acetate and then washed with a saturated sodium chloride aqueous solution. The resulting organic layer was dried over sodium sulfate, filtered, and then concentrated under reduced pressure. The resulting residue was purified by means of silica gel column chromatography (ethyl acetate/ethanol=19/1), thereby obtaining 1-{2-[4-(2-amino-5-fluoropyridin-3-yl)phenoxy]pyrimidin- 5-yl}-3-[2-(pyridin-3-yl)-5-(trifluoromethyl)phenyl]urea (444 mg, Compound (II)). To this Compound (II) (100 mg), 5 mL of acetone and 0.5 mL of water were added, followed by stirring at 50° C. To this solution, p-toluenesulfonic acid monohydrate (68 mg; p-TsOH.H₂O) was added. The reaction mixture was stirred at 50° C. for 10 minutes. Thereafter, heating of the reaction mixture was stopped, and the resulting reaction mixture was stirred overnight. On that occasion, a crystal started to be precipitated at 40° C. The crystal was collected at room temperature by means of filtration and then dried, thereby obtaining the present compound (100 mg) having the following physical properties value.

Properties: Crystalline white solid
LC-MS: 562 (M+H)⁺
¹H-NMR (DMSO-d₆): δ2.27 (s, 6H), 3.50-5.50 (br, 4H), 7.10 (dd, 4H), 7.29-7.36 (m, 2H), 7.41-7.49 (m, 4H), 7.50-7.57 (m, 2H), 7.58 (s, 2H), 7.88-8.00 (m, 2H), 8.16 (t, 1H), 8.30-8.39 (m, 2H), 8.47 (s, 1H), 8.65 (s, 2H), 8.84 (dd, 1H), 8.93 (d, 1H), 9.20 (s, 1H)

The powder X-ray diffraction spectrum of the present compound (crystalline white solid) is shown in FIG. 5.
(1) Powder X-Ray Diffraction Spectrum The foregoing crystal is characterized by, in a powder X-ray diffraction spectrum obtained using a Cu-Kα ray, data of a diffraction angle (2θ) and a relative intensity shown in the following Table 1.

TABLE 1

| Diffraction angle (2θ) | Relative intensity |
| --- | --- |
| 6.109 | 18.5 |
| 6.294 | 18.1 |
| 7.762 | 27.2 |
| 9.645 | 81.7 |
| 10.181 | 24.4 |
| 12.300 | 25.7 |
| 12.565 | 42.7 |
| 13.227 | 35.4 |
| 13.585 | 29.7 |
| 14.052 | 19.3 |
| 14.849 | 67.3 |
| 15.467 | 21.3 |
| 16.944 | 29.5 |
| 17.983 | 54.8 |
| 18.522 | 45.2 |
| 18.788 | 46.1 |
| 19.320 | 50.2 |
| 20.581 | 30.0 |
| 21.250 | 35.0 |
| 21.551 | 58.5 |
| 22.110 | 100 |
| 22.727 | 23.8 |
| 23.196 | 37.9 |
| 24.360 | 47.9 |

Example 2

1-{2-[4-(2-amino-5-fluoropyridin-3-yl)phenoxy]pyrimidin-5-yl}-3-[2-(pyridin-3-yl)-5-(trifluoromethyl)phenyl]urea dibenzenesulfonate The same operations as in Example 1 were followed, except for using benzenesulfonic acid in place of the p-toluenesulfonic acid monohydrate, thereby obtaining the present compound having the following physical properties value. That is, Compound (II) (100 mg) was added with and dissolved in 2 mL of acetone. To this solution, 56 mg of benzenesulfonic acid in 0.5 mL of acetone was added. The reaction mixture was concentrated under reduced pressure. To the resulting residue, isopropyl acetate was added, followed by stirring at 85° C. The resulting solid was collected by means of filtration and then dried, thereby obtaining the present compound.

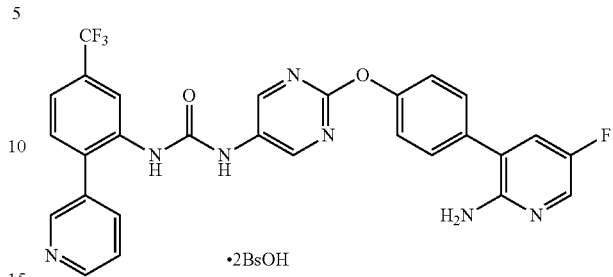

·2BsOH

Properties: Crystalline white solid
LC-MS: 562 (M+H)⁺
¹H-NMR (DMSO-d₆): δ3.50-6.00 (br, 4H), 7.27-7.41 (m, 8H), 7.51-7.68 (m, 8H), 7.95-8.05 (m, 2H), 8.20 (t, 1H), 8.34 (s, 1H), 8.40-8.47 (m, 1H), 8.52 (s, 1H), 8.66 (s, 2H), 8.88 (dd, 1H), 8.99 (d, 1H), 9.21 (s, 1H)

The powder X-ray diffraction spectrum of the present compound (crystalline white solid) is shown in FIG. 6.
(1) Powder X-Ray Diffraction Spectrum The foregoing crystal is characterized by, in a powder X-ray diffraction spectrum obtained using a Cu-Kα ray, data of a diffraction angle (2θ) and a relative intensity shown in the following Table 2.

TABLE 2

| Diffraction angle (2θ) | Relative intensity |
| --- | --- |
| 5.991 | 15.4 |
| 6.713 | 19.1 |
| 7.776 | 27.7 |
| 10.078 | 68.9 |
| 10.415 | 23.7 |
| 11.929 | 14.4 |
| 12.532 | 18.6 |
| 12.961 | 34.7 |
| 13.409 | 76.8 |
| 14.145 | 15.5 |
| 15.159 | 77.0 |
| 15.550 | 20.3 |
| 16.031 | 17.5 |
| 16.932 | 21.1 |
| 17.518 | 28.5 |
| 17.950 | 19.6 |
| 18.631 | 23.8 |
| 18.914 | 36.7 |
| 19.495 | 56.8 |
| 20.182 | 100 |
| 20.734 | 37.2 |
| 21.426 | 25.0 |
| 22.432 | 52.0 |
| 22.841 | 33.5 |
| 23.600 | 28.3 |
| 23.974 | 94.3 |

Example 3

1-{2-[4-(2-amino-5-fluoropyridin-3-yl)phenoxy]pyrimidin-5-yl}-3-[2-(pyridin-3-yl)-5-(trifluoromethyl)phenyl]urea dimethanesulfonate The same operations as in Example 1 were followed, except for using methanesulfonic acid in place of the p-toluenesulfonic acid monohydrate, thereby obtaining the present compound having the following physical properties value.

That is, Compound (II) (100 mg) was added with and dissolved in 10 mL of ethanol at 50 to 70° C. To this solution, 0.024 mL of methanesulfonic acid was added, followed by stirring. The reaction mixture was stirred for one hour, and the resulting crystal was then collected by means of filtration and dried, thereby obtaining the present compound.

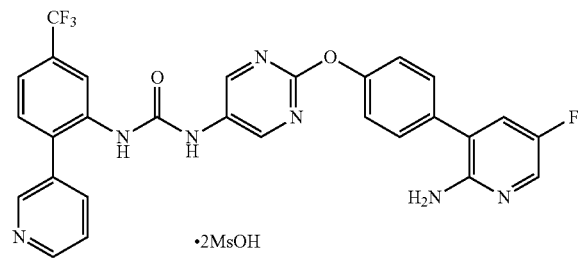 [SMILES: Nc1ncc(F)cc1-c1ccc(Oc2ncc(NC(=O)Nc3cc(C(F)(F)F)ccc3-c3cccnc3)cn2)cc1]

•2MsOH

Properties: Crystalline white solid
LC-MS: 562 (M+H)$^+$
$^1$H-NMR (DMSO-d$_6$): δ2.34 (s, 6H), 3.50-5.50 (br, 4H), 7.33 (d, 2H), 7.52-7.62 (m, 4H), 7.88-7.97 (m, 2H), 8.14-8.19 (m, 1H), 8.29-8.37 (m, 2H), 8.50 (s, 1H), 8.67 (s, 2H), 8.85 (dd, 1H), 8.92 (d, 1H), 9.26 (s, 1H)

The powder X-ray diffraction spectrum of the present compound (crystalline white solid) is shown in FIG. 7.

(1) Powder X-Ray Diffraction Spectrum

The foregoing crystal is characterized by, in a powder X-ray diffraction spectrum obtained using a Cu-Kα ray, data of a diffraction angle (2θ) and a relative intensity shown in the following Table 3.

TABLE 3

| Diffraction angle (2θ) | Relative intensity |
|---|---|
| 5.304 | 100 |
| 5.932 | 24.1 |
| 8.913 | 33.5 |
| 9.344 | 23.8 |
| 9.638 | 22.2 |
| 10.546 | 75.2 |
| 11.774 | 27.5 |
| 12.515 | 20.7 |
| 12.919 | 37.3 |
| 13.721 | 20.2 |
| 14.253 | 19.7 |
| 15.469 | 31.6 |
| 15.910 | 48.9 |
| 16.873 | 26.8 |
| 17.866 | 49.0 |
| 18.768 | 28.2 |
| 19.300 | 40.2 |
| 19.620 | 68.7 |
| 20.770 | 49.0 |
| 21.226 | 73.2 |
| 21.608 | 54.7 |
| 22.472 | 64.1 |
| 23.355 | 48.0 |
| 23.781 | 33.2 |
| 24.505 | 54.0 |

Example 4

1-{2-[4-(2-amino-5-fluoropyridin-3-yl)phenoxy]pyrimidin-5-yl}-3-[2-(pyridin-3-yl)-5-(trifluoromethyl)phenyl]urea dihydrochloride The same operations as in Example 1 were followed, except for using hydrochloric acid in place of the p-toluenesulfonic acid monohydrate, thereby obtaining the present compound having the following physical properties value. That is, a DMSO solution of Compound (II) was added to 1N hydrochloric acid, followed by stirring. A precipitated crystal was collected by means of filtration and then dried, thereby obtaining the present compound.

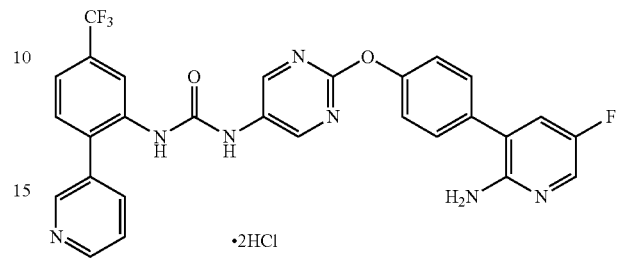

•2HCl

Properties: Crystalline white solid
LC-MS: 562 (M+H)$^+$
$^1$H-NMR (DMSO-d$_6$): δ4.00-5.50 (br, 4H), 7.34 (d, 2H), 7.52-7.62 (m, 4H), 7.90-8.01 (m, 2H), 8.21 (t, 1H), 8.32-8.39 (m, 1H), 8.42 (s, 1H), 8.67 (s, 2H), 8.76 (s, 1H), 8.87 (dd, 1H), 8.93-9.00 (m, 1H), 9.84 (s, 1H)

The powder X-ray diffraction spectrum of the present compound (crystalline white solid) is shown in FIG. 8.

(1) Powder X-Ray Diffraction Spectrum

The foregoing crystal is characterized by, in a powder X-ray diffraction spectrum obtained using a Cu-Kα ray, data of a diffraction angle (2θ) and a relative intensity shown in the following Table 4.

TABLE 4

| Diffraction angle (2θ) | Relative intensity |
|---|---|
| 6.025 | 26.6 |
| 6.838 | 26.4 |
| 8.300 | 39.2 |
| 9.867 | 22.3 |
| 12.516 | 32.3 |
| 13.700 | 25.7 |
| 13.931 | 29.9 |
| 14.896 | 24.0 |
| 15.884 | 31.5 |
| 18.306 | 42.8 |
| 19.812 | 50.2 |
| 20.935 | 47.2 |
| 22.469 | 100 |
| 22.889 | 38.0 |
| 24.080 | 22.1 |

Example 5

1-(2-(1H-pyrazol-1-yl)-5-(trifluoromethyl)phenyl)-3-(2-(4-(2-amino-5-chloropyridin-3-yl)phenoxy)pyrimidin-5-yl)urea p-Toluenesulfonate The same operations as those in Reference Example 1→Reference Example 2→Reference Example 3→Reference Example 4→Example 1 were followed, except for using corresponding 2-(1H-pyrazol-1-yl)-5-(trifluoromethyl)aniline (CAS No.: 883881-78-5) in place of the 2-(pyridin-3-yl)-5-(trifluoromethyl)benzeneamine and 2-amino-3-bromo-5-chloropyridine in place of the 2-amino-3-bromo-5-fluoropyridine, respectively, thereby obtaining the present compound having the following physical properties value. The properties of the resulting present compound were amorphous.

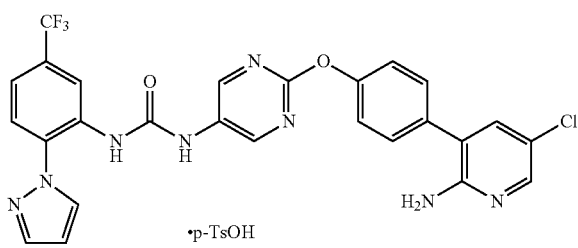 [SMILES: Nc1ncc(Cl)cc1-c1ccc(Oc2ncc(NC(=O)Nc3cc(C(F)(F)F)ccc3-n3cccn3)cn2)cc1]

•p-TsOH

Properties: Amorphous white solid
LC-MS: 567 (M+H)$^+$
$^1$H-NMR (DMSO-d$_6$): δ2.29 (s, 3H), 3.35-4.20 (br, 3H), 6.67-6.71 (m, 1H), 7.11 (d, 2H), 7.32 (d, 2H), 7.47 (d, 2H), 7.51-7.57 (m, 1H), 7.69-7.73 (m, 3H), 7.74-7.80 (m, 1H), 7.97 (d, 1H), 8.09 (d, 1H), 8.43 (d, 1H), 8.57-8.61 (m, 1H), 8.72 (s, 2H), 9.74 (s, 1H), 10.00 (s, 1H)
The powder X-ray diffraction spectrum of the present compound (amorphous white solid) is shown in FIG. 9.

Example 6

1-(2-(1H-pyrazol-1-yl)-5-(trifluoromethyl)phenyl)-3-(2-(4-(2-amino-5-chloropyridin-3-yl)phenoxy)pyrimidin-5-yl)urea Benzenesulfonate The same operations as in Example 5 were followed, except for using benzenesulfonic acid in place of the p-toluenesulfonic acid monohydrate, thereby obtaining the present compound having the following physical properties value. The properties of the resulting present compound were amorphous.

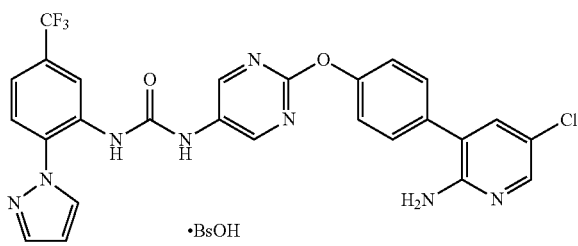

•BsOH

Properties: Amorphous white solid
LC-MS: 567 (M+H)$^+$
$^1$H-NMR (DMSO-d$_6$): δ3.20-3.90 (br, 3H), 6.65-6.74 (m, 1H), 7.26-7.39 (m, 5H), 7.50-7.64 (m, 5H), 7.72-7.83 (m, 2H), 7.95-8.01 (m, 1H), 8.10 (d, 1H), 8.40-8.47 (m, 1H), 8.57-8.64 (m, 1H), 8.72 (s, 2H), 9.74 (s, 1H), 10.00 (s, 1H)
The powder X-ray diffraction spectrum of the present compound (amorphous white solid) is shown in FIG. 10.

Example 7

1-(2-(1H-pyrazol-1-yl)-5-(trifluoromethyl)phenyl)-3-(2-(4-(2-amino-5-chloropyridin-3-yl)phenoxy)pyrimidin-5-yl)urea Methanesulfonate The same operations as in Example 5 were followed, except for using methanesulfonic acid in place of the p-toluenesulfonic acid monohydrate, thereby obtaining the present compound having the following physical properties value. That is, Compound (III) (100 mg) was added with and dissolved in 1.0 mL of ethyl acetate at 50 to 70° C. To this solution, an ethyl acetate solution containing methanesulfonic acid (0.011 mL) was added. The reaction mixture was stirred at room temperature for 15 minutes and subsequently stirred on an ice bath for 15 minutes. The resulting crystal was collected by means of filtration and then dried, thereby obtaining the present compound.

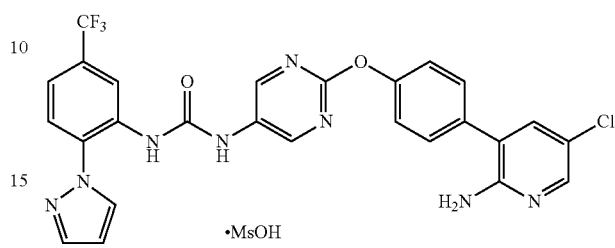

•MsOH

Properties: Crystalline white solid
LC-MS: 567 (M+H)$^+$
$^1$H-NMR (DMSO-d$_6$): δ2.31 (s, 3H), 3.35-3.85 (br, 3H), 6.69 (dd, 1H), 7.32 (d, 2H), 7.50-7.58 (m, 3H), 7.72 (d, 1H), 7.77 (d, 1H), 7.97 (d, 1H), 8.09 (d, 1H), 8.43 (dd, 1H), 8.59 (d, 1H), 8.72 (s, 2H), 9.74 (s, 1H), 10.00 (s, 1H)
The powder X-ray diffraction spectrum of the present compound (crystalline white solid) is shown in FIG. 11.
(1) Powder X-Ray Diffraction Spectrum
The foregoing crystal is characterized by, in a powder X-ray diffraction spectrum obtained using a Cu-Kα ray, data of a diffraction angle (2θ) and a relative intensity shown in the following Table 5.

TABLE 5

| Diffraction angle (2θ) | Relative intensity |
| --- | --- |
| 5.422 | 86.8 |
| 8.639 | 58.3 |
| 8.971 | 100 |
| 9.643 | 67.5 |
| 10.393 | 48.9 |
| 11.846 | 92.0 |
| 13.125 | 90.2 |
| 16.019 | 66.4 |
| 16.270 | 69.5 |
| 16.889 | 78.1 |
| 17.388 | 54.6 |
| 18.185 | 52.6 |
| 19.528 | 72.0 |
| 20.488 | 77.5 |
| 20.827 | 78.9 |
| 21.892 | 98.3 |
| 22.586 | 74.7 |
| 23.898 | 67.6 |

Example 8

1-(2-(1H-pyrazol-1-yl)-5-(trifluoromethyl)phenyl)-3-(2-(4-(2-amino-5-chloropyridin-3-yl)phenoxy)pyrimidin-5-yl)urea Hydrochloride The same operations as in Example 5 were followed, except for using hydrochloric acid in place of the p-toluenesulfonic acid monohydrate, thereby obtaining the present compound having the following physical properties value. That is, Compound (III) (90 mg) was added with and dissolved in 1.8 mL of ethyl acetate and 1.8 mL of ethanol. To this solution, 0.079 mL of a 4N hydrochloric acid-ethyl acetate solution was added. The reaction mixture was stirred at room temperature and then concentrated under reduced pressure. To the resulting residue, ethyl acetate was added, followed by stirring. The resulting crystal was collected by means of filtration and then dried, thereby obtaining the present compound (97 mg).

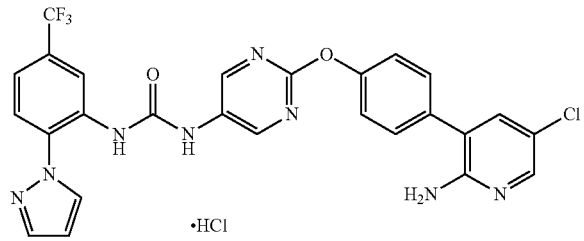 [SMILES: Nc1ncc(Cl)cc1-c1ccc(Oc2ncc(NC(=O)Nc3cc(C(F)(F)F)ccc3-n3cccn3)cn2)cc1 ; Cl]

Properties: Crystalline white solid

LC-MS: 567 (M+H)$^+$ $^1$H-NMR (DMSO-d$_6$): δ3.70-5.20 (br, 3H), 6.69 (t, 1H), 7.30-7.35 (m, 2H), 7.52-7.57 (m, 3H), 7.75-7.80 (m, 2H), 7.97 (d, 1H), 8.16 (d, 1H), 8.43 (d, 1H), 8.59 (d, 1H), 8.73 (d, 2H), 9.75 (s, 1H), 10.06 (s, 1H)

The powder X-ray diffraction spectrum of the present compound (crystalline white solid) is shown in FIG. 12.

(1) Powder X-Ray Diffraction Spectrum

The foregoing crystal is characterized by, in a powder X-ray diffraction spectrum obtained using a Cu-Kα ray, data of a diffraction angle (2θ) and a relative intensity shown in the following Table 6.

TABLE 6

| Diffraction angle (2θ) | Relative intensity |
| --- | --- |
| 5.628 | 26.1 |
| 10.371 | 31.4 |
| 10.725 | 67.1 |
| 11.289 | 32.5 |
| 12.303 | 22.4 |
| 12.733 | 53.3 |
| 13.680 | 25.8 |
| 14.028 | 37.5 |
| 14.531 | 31.2 |
| 16.071 | 41.9 |
| 16.639 | 78.3 |
| 17.932 | 63.8 |
| 18.660 | 63.6 |
| 18.910 | 92.9 |
| 19.891 | 62.8 |
| 20.755 | 53.8 |
| 21.350 | 87.7 |
| 22.519 | 100 |
| 22.840 | 62.5 |
| 24.327 | 80.1 |
| 24.740 | 41.9 |

Example 9

1-{2-[4-(2-amino-5-chloro-3-pyridinyl)phenoxy]-5-pyrimidinyl}-3-[2-(methylsulfonyl)-5-(trifluoromethyl)phenyl]urea p-Toluenesulfonate (Crystal A)

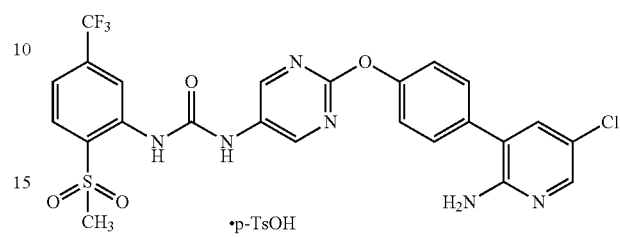

The same operations as those in Reference Example 1→Reference Example 2→Reference Example 3→Reference Example 4→Example 1 were followed, except for using corresponding 2-(methylsulfonyl)-5-(trifluoromethyl) aniline (CAS No.: 402-19-7) in place of the 2-(pyridin-3-yl)-5-(trifluoromethyl)benzeneamine and 2-amino-3-bromo-5-chloropyridine in place of the 2-amino-3-bromo-5-fluoropyridine, respectively, thereby obtaining the present compound having the following physical properties value. As the recrystallization solvent of Example 1, ethanol was used in place of the acetone.

Properties: Crystalline white solid (crystal A)

LC-MS: 579 (M+H)$^+$ $^1$H-NMR (DMSO-d$_6$): δ2.29 (s, 3H), 3.39 (s, 3H), 3.70-4.60 (br, 3H), 7.11 (d, 2H), 7.34 (d, 2H), 7.47 (d, 2H), 7.55 (d, 2H), 7.62-7.72 (m, 1H), 7.79 (d, 1H), 8.08 (d, 1H), 8.13 (d, 1H), 8.61-8.68 (m, 1H), 8.77 (s, 2H), 8.99 (s, 1H), 10.32 (s, 1H)

The powder X-ray diffraction spectrum of the present compound (crystalline white solid) is shown in FIG. 1.

(1) Powder X-Ray Diffraction Spectrum

The foregoing crystal is characterized by, in a powder X-ray diffraction spectrum obtained using a Cu-Kα ray, data of a diffraction angle (2θ) and a relative intensity shown in the following Table 7.

TABLE 7

| Diffraction angle (2θ) | Relative intensity |
| --- | --- |
| 6.349 | 100 |
| 7.739 | 28.5 |
| 9.976 | 29.0 |
| 11.081 | 21.9 |
| 11.417 | 25.1 |
| 12.681 | 72.7 |
| 13.223 | 26.8 |
| 14.832 | 53.4 |
| 15.417 | 58.1 |
| 15.981 | 23.3 |
| 16.886 | 37.3 |
| 17.327 | 29.1 |
| 17.862 | 35.9 |
| 18.293 | 66.6 |
| 19.003 | 68.4 |
| 19.464 | 76.4 |
| 20.556 | 23.4 |
| 20.922 | 37.6 |
| 21.470 | 44.1 |
| 22.040 | 34.1 |
| 23.824 | 25.9 |
| 24.486 | 40.1 |

Example 10

1-{2-[4-(2-amino-5-chloro-3-pyridinyl)phenoxy]-5-pyrimidinyl}-3-[2-(methylsulfonyl)-5-(trifluoromethyl)phenyl]urea Benzenesulfonate (Crystal A)

The same operations as in Example 9 were followed, except for using benzenesulfonic acid in place of the p-toluenesulfonic acid monohydrate, thereby obtaining the present compound having the following physical properties value. As the recrystallization solvent of Example 1 to be adopted in Example 9, acetonitrile was used in place of the acetone.

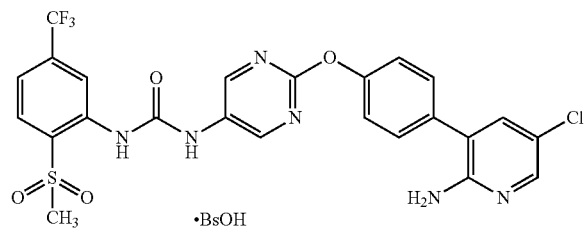

Properties: Crystalline white solid (crystal A)
LC-MS: 579 (M+H)$^+$
$^1$H-NMR (DMSO-d$_6$): δ3.39 (s, 3H), 3.45-4.10 (br, 3H), 7.27-7.37 (m, 5H), 7.52-7.62 (m, 4H), 7.63-7.69 (m, 1H), 7.73 (d, 1H), 8.06-8.13 (m, 2H), 8.61-8.66 (m, 1H), 8.77 (s, 2H), 8.99 (s, 1H), 10.33 (s, 1H)

The powder X-ray diffraction spectrum of the present compound (crystalline white solid) is shown in FIG. 2.

(1) Powder X-Ray Diffraction Spectrum

The foregoing crystal is characterized by, in a powder X-ray diffraction spectrum obtained using a Cu-Kα ray, data of a diffraction angle (2θ) and a relative intensity shown in the following Table 8.

TABLE 8

| Diffraction angle (2θ) | Relative intensity |
| --- | --- |
| 6.774 | 81.7 |
| 7.779 | 21.2 |
| 10.256 | 31.6 |
| 11.201 | 20.3 |
| 11.502 | 19.4 |
| 13.540 | 55.9 |
| 15.649 | 100 |
| 16.015 | 42.9 |
| 17.127 | 21.5 |
| 18.005 | 59.4 |
| 18.412 | 70.5 |
| 18.700 | 48.4 |
| 19.522 | 68.3 |
| 20.254 | 31.7 |
| 20.638 | 42.5 |
| 21.649 | 30.6 |
| 21.950 | 29.9 |
| 22.659 | 29.4 |
| 23.487 | 37.3 |
| 24.572 | 67.8 |

Example 11

1-{2-[4-(2-amino-5-chloro-3-pyridinyl)phenoxy]-5-pyrimidinyl}-3-[2-(methylsulfonyl)-5-(trifluoromethyl)phenyl]urea Methanesulfonate The same operations as in Example 9 were followed, except for using methanesulfonic acid in place of the p-toluenesulfonic acid monohydrate, thereby obtaining the present compound having the following physical properties value. That is, 120 mg of Compound (I) was added with and dissolved in 8.4 mL of acetonitrile at 50 to 70° C. To this solution, 0.22 mL of a 1 mol/L methanesulfonic acid-acetonitrile solution was added. The reaction mixture was stirred at room temperature for 2 hours and then stirred on ice bath for one hour. The resulting crystal was collected by means of filtration and then dried, thereby obtaining the present compound.

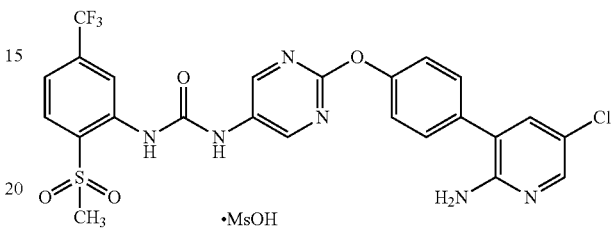

Properties: Crystalline white solid
LC-MS: 579 (M+H)$^+$
$^1$H-NMR (DMSO-d$_6$): δ2.32 (s, 3H), 3.39 (s, 3H), 3.45-3.95 (br, 3H), 7.33 (d, 2H), 7.55 (d, 2H), 7.66 (d, 1H), 7.72-7.77 (m, 1H), 8.06-8.12 (m, 2H), 8.62-8.67 (m, 1H), 8.77 (s, 2H), 8.99 (s, 1H), 10.33 (s, 1H)

The powder X-ray diffraction spectrum of the present compound (crystalline white solid) is shown in FIG. 3.

(1) Powder X-Ray Diffraction Spectrum

The foregoing crystal is characterized by, in a powder X-ray diffraction spectrum obtained using a Cu-Kα ray, data of a diffraction angle (2θ) and a relative intensity shown in the following Table 9.

TABLE 9

| Diffraction angle (2θ) | Relative intensity |
| --- | --- |
| 4.626 | 32.8 |
| 7.039 | 43.9 |
| 9.333 | 37.1 |
| 14.113 | 49.0 |
| 18.742 | 100 |
| 20.433 | 83.9 |
| 21.352 | 59.9 |
| 23.308 | 65.7 |
| 24.803 | 41.1 |

Example 12

1-{2-[4-(2-amino-5-chloro-3-pyridinyl)phenoxy]-5-pyrimidinyl}-3-[2-(methylsulfonyl)-5-(trifluoromethyl)phenyl]urea Hydrochloride The same operations as in Example 9 were followed, except for using hydrochloric acid in place of the p-toluenesulfonic acid monohydrate, thereby obtaining the present compound having the following physical properties value.

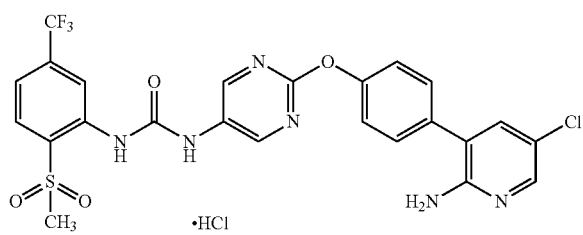 [SMILES: CS(=O)(=O)c1ccc(C(F)(F)F)cc1NC(=O)Nc1cnc(Oc2ccc(-c3cc(Cl)cnc3N)cc2)nc1 ; Cl]

Properties: Crystalline white solid
LC-MS: 579 (M+H)$^+$
$^1$H-NMR (DMSO-d$_6$): δ3.40 (s, 3H), 3.45-3.95 (br, 3H), 7.30-7.35 (m, 2H), 7.52-7.57 (m, 2H), 7.66 (dd, 1H), 7.70 (d, 1H), 8.07-8.11 (m, 2H), 8.62-8.65 (m, 1H), 8.77 (s, 2H), 8.99 (s, 1H), 10.36 (s, 1H)

The powder X-ray diffraction spectrum of the present compound (crystalline white solid) is shown in FIG. 4.

(1) Powder X-Ray Diffraction Spectrum

The foregoing crystal is characterized by, in a powder X-ray diffraction spectrum obtained using a Cu-Kα ray, data of a diffraction angle (2θ) and a relative intensity shown in the following Table 10.

TABLE 10

| Diffraction angle (2θ) | Relative intensity |
| --- | --- |
| 4.599 | 48.4 |
| 5.952 | 33.1 |
| 7.057 | 67.1 |
| 7.750 | 33.5 |
| 9.381 | 27.9 |
| 10.187 | 33.7 |
| 11.824 | 58.7 |
| 12.213 | 51.2 |
| 13.013 | 28.3 |
| 15.273 | 43.3 |
| 17.808 | 100 |
| 18.494 | 49.8 |
| 18.787 | 72.7 |
| 19.887 | 34.0 |
| 20.520 | 60.8 |
| 21.117 | 59.5 |
| 21.956 | 37.1 |
| 22.514 | 51.9 |
| 23.669 | 37.7 |
| 24.537 | 41.1 |

Example 13

1-{2-[4-(2-amino-5-chloro-3-pyridinyl)phenoxy]-5-pyrimidinyl}-3-[2-(methylsulfonyl)-5-(trifluoromethyl)phenyl]urea p-Toluenesulfonate (Crystal B)

The compound (10 mg) produced in Example 9 was added with and dissolved in 0.7 mL of acetonitrile at 60 to 80° C. This solution was stirred at room temperature overnight, and the resulting crystal was dried, thereby obtaining the present compound having the following physical properties value.

Properties: Crystalline white solid (crystal B)
LC-MS: 579 (M+H)$^+$
$^1$H-NMR (DMSO-d$_6$): δ2.29 (s, 3H), 3.39 (s, 3H), 3.70-4.60 (br, 3H), 7.11 (d, 2H), 7.34 (d, 2H), 7.47 (d, 2H), 7.55 (d, 2H), 7.62-7.72 (m, 1H), 7.79 (d, 1H), 8.08 (d, 1H), 8.13 (d, 1H), 8.61-8.68 (m, 1H), 8.77 (s, 2H), 8.99 (s, 1H), 10.32 (s, 1H)

The powder X-ray diffraction spectrum of the present compound (crystalline white solid) is shown in FIG. 13.

(1) Powder X-Ray Diffraction Spectrum

The foregoing crystal is characterized by, in a powder X-ray diffraction spectrum obtained using a Cu-Kα ray, data of a diffraction angle (2θ) and a relative intensity shown in the following Table 11.

TABLE 11

| Diffraction angle (2θ) | Relative intensity |
| --- | --- |
| 5.16 | 28.2 |
| 5.57 | 20.7 |
| 7.01 | 100 |
| 9.62 | 22.4 |
| 9.97 | 23.1 |
| 10.83 | 18.4 |
| 11.15 | 15.4 |
| 12.20 | 21.0 |
| 13.47 | 19.6 |
| 14.63 | 25.2 |
| 15.81 | 24.5 |
| 16.30 | 24.8 |
| 17.63 | 24.0 |
| 18.26 | 18.7 |
| 19.28 | 40.1 |
| 19.93 | 39.4 |
| 20.72 | 53.5 |
| 21.25 | 27.1 |
| 21.73 | 22.9 |
| 22.88 | 22.8 |
| 23.51 | 18.7 |
| 24.30 | 16.4 |
| 24.74 | 21.4 |

Example 14

1-{2-[4-(2-amino-5-chloro-3-pyridinyl)phenoxy]-5-pyrimidinyl}-3-[2-(methylsulfonyl)-5-(trifluoromethyl)phenyl]urea p-Toluenesulfonate (Crystal I)

The compound (10 mg) produced in Example 9 was added with and dissolved in 110 μL of 30% hydrated ethanol at 50 to 75° C. This solution was stirred at room temperature overnight, and the resulting crystal was dried, thereby obtaining the present compound having the following physical properties value.

Properties: Crystalline white solid (crystal I)
LC-MS: 579 (M+H)$^+$
$^1$H-NMR (DMSO-d$_6$): δ2.29 (s, 3H), 3.39 (s, 3H), 3.70-4.60 (br, 3H), 7.11 (d, 2H), 7.34 (d, 2H), 7.47 (d, 2H), 7.55 (d, 2H), 7.62-7.72 (m, 1H), 7.79 (d, 1H), 8.08 (d, 1H), 8.13 (d, 1H), 8.61-8.68 (m, 1H), 8.77 (s, 2H), 8.99 (s, 1H), 10.32 (s, 1H)

The powder X-ray diffraction spectrum of the present compound (crystalline white solid) is shown in FIG. 14.

(1) Powder X-Ray Diffraction Spectrum

The foregoing crystal is characterized by, in a powder X-ray diffraction spectrum obtained using a Cu-Kα ray, data of a diffraction angle (2θ) and a relative intensity shown in the following Table 12.

TABLE 12

| Diffraction angle (2θ) | Relative intensity |
| --- | --- |
| 6.30 | 33.8 |
| 7.72 | 49.5 |
| 9.63 | 77.1 |
| 10.27 | 18.5 |

TABLE 12-continued

| Diffraction angle (2θ) | Relative intensity |
| --- | --- |
| 11.44 | 13.2 |
| 12.39 | 19.3 |
| 13.11 | 18.3 |
| 13.36 | 17.7 |
| 14.09 | 20.2 |
| 15.40 | 91.0 |
| 16.14 | 30.8 |
| 16.94 | 84.6 |
| 17.69 | 100 |
| 17.90 | 82.7 |
| 18.65 | 35.9 |
| 19.33 | 29.8 |
| 19.73 | 62.9 |
| 20.23 | 34.1 |
| 20.68 | 35.8 |
| 21.09 | 88.0 |
| 22.44 | 29.6 |
| 23.02 | 26.9 |
| 24.51 | 21.1 |

Example 15

1-{2-[4-(2-amino-5-chloro-3-pyridinyl)phenoxy]-5-pyrimidinyl}-3-[2-(methylsulfonyl)-5-(trifluoromethyl)phenyl]urea Benzenesulfonate (Crystal B)

The compound (10 mg) produced in Example 10 was added with and dissolved in 40 μL of 30% hydrated ethanol at 50 to 75° C. This solution was stirred at room temperature overnight, and the resulting crystal was dried, thereby obtaining the present compound having the following physical properties value.

Properties: Crystalline white solid (crystal B)
LC-MS: 579 (M+H)$^+$
$^1$H-NMR (DMSO-d$_6$): δ3.39 (s, 3H), 3.45-4.10 (br, 3H), 7.27-7.37 (m, 5H), 7.52-7.62 (m, 4H), 7.63-7.69 (m, 1H), 7.73 (d, 1H), 8.06-8.13 (m, 2H), 8.61-8.66 (m, 1H), 8.77 (s, 2H), 8.99 (s, 1H), 10.33 (s, 1H)

The powder X-ray diffraction spectrum of the present compound (crystalline white solid) is shown in FIG. 15.
(1) Powder X-Ray Diffraction Spectrum
The foregoing crystal is characterized by, in a powder X-ray diffraction spectrum obtained using a Cu-Kα ray, data of a diffraction angle (2θ) and a relative intensity shown in the following Table 13.

TABLE 13

| Diffraction angle (2θ) | Relative intensity |
| --- | --- |
| 6.96 | 25.0 |
| 7.87 | 30.0 |
| 8.69 | 23.2 |
| 9.44 | 15.7 |
| 10.02 | 20.4 |
| 10.55 | 30.6 |
| 12.51 | 23.5 |
| 13.59 | 27.9 |
| 15.02 | 18.6 |
| 15.65 | 43.3 |
| 16.42 | 49.7 |
| 16.69 | 80.6 |
| 17.00 | 28.4 |
| 17.98 | 98.2 |
| 18.91 | 98.2 |
| 20.44 | 18.2 |
| 20.74 | 29.9 |
| 21.04 | 48.7 |
| 21.44 | 100 |

TABLE 13-continued

| Diffraction angle (2θ) | Relative intensity |
| --- | --- |
| 22.79 | 30.2 |
| 24.22 | 49.2 |
| 24.37 | 50.8 |

Example 16

1-{2-[4-(2-amino-5-chloro-3-pyridinyl)phenoxy]-5-pyrimidinyl}-3-[2-(methylsulfonyl)-5-(trifluoromethyl)phenyl]urea Benzenesulfonate (crystal F)

The compound (10 mg) produced in Example 10 was added with and dissolved in 200 μL of acetone and 50 μL of acetic acid at 40 to 60° C. This solution was stirred at room temperature overnight, and the resulting crystal was dried, thereby obtaining the present compound having the following physical properties value.

Properties: Crystalline white solid (crystal F)
LC-MS: 579 (M+H)$^+$
$^1$H-NMR (DMSO-d$_6$): δ3.39 (s, 3H), 3.45-4.10 (br, 3H), 7.27-7.37 (m, 5H), 7.52-7.62 (m, 4H), 7.63-7.69 (m, 1H), 7.73 (d, 1H), 8.06-8.13 (m, 2H), 8.61-8.66 (m, 1H), 8.77 (s, 2H), 8.99 (s, 1H), 10.33 (s, 1H)

The powder X-ray diffraction spectrum of the present compound (crystalline white solid) is shown in FIG. 16.
(1) Powder X-Ray Diffraction Spectrum
The foregoing crystal is characterized by, in a powder X-ray diffraction spectrum obtained using a Cu-Kα ray, data of a diffraction angle (2θ) and a relative intensity shown in the following Table 14.

TABLE 14

| Diffraction angle (2θ) | Relative intensity |
| --- | --- |
| 6.70 | 35.5 |
| 6.97 | 76.6 |
| 7.37 | 53.4 |
| 8.36 | 14.4 |
| 8.88 | 48.7 |
| 11.04 | 22.5 |
| 13.40 | 14.9 |
| 13.88 | 27.8 |
| 14.84 | 17.7 |
| 15.48 | 25.0 |
| 16.59 | 41.7 |
| 17.40 | 15.2 |
| 18.24 | 23.6 |
| 19.12 | 81.1 |
| 19.73 | 100 |
| 20.38 | 45.5 |
| 20.83 | 38.5 |
| 21.32 | 28.3 |
| 22.30 | 21.3 |
| 22.85 | 20.8 |
| 24.33 | 37.6 |

Example 17

1-{2-[4-(2-amino-5-chloro-3-pyridinyl)phenoxy]-5-pyrimidinyl}-3-[2-(methylsulfonyl)-5-(trifluoromethyl)phenyl]urea Hydrobromide The same operations as in Example 9 were followed, except for using hydrobromic acid in place of the p-toluenesulfonic acid monohydrate, thereby obtaining the present compound having the following physical properties value.

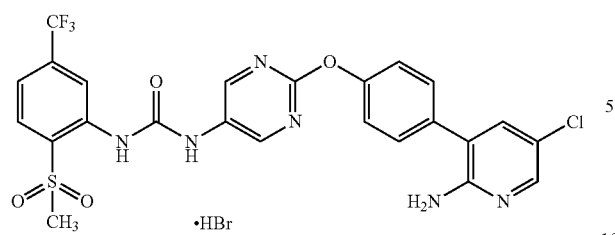

Properties: Crystalline white solid
LC-MS: 579 (M+H)+
$^1$H-NMR (DMSO-$d_6$): δ3.40 (s, 3H), 4.41-5.34 (br, 3H), 7.33 (d, 2H), 7.55 (d, 2H), 7.66 (dd, 1H), 7.74 (d, 1H), 8.05-8.14 (m, 2H), 8.61-8.66 (m, 1H), 8.77 (s, 2H), 8.99 (s, 1H), 10.32 (s, 1H)

The powder X-ray diffraction spectrum of the present compound (crystalline white solid) is shown in FIG. 17.
(1) Powder X-Ray Diffraction Spectrum
The foregoing crystal is characterized by, in a powder X-ray diffraction spectrum obtained using a Cu-Kα ray, data of a diffraction angle (2θ) and a relative intensity shown in the following Table 15.

TABLE 15

| Diffraction angle (2θ) | Relative intensity |
|---|---|
| 6.28 | 47.5 |
| 12.53 | 35.0 |
| 14.15 | 43.5 |
| 15.51 | 41.1 |
| 17.35 | 26.1 |
| 18.80 | 100 |
| 19.40 | 90.5 |
| 21.48 | 76.3 |
| 22.67 | 51.9 |
| 23.44 | 39.7 |
| 24.15 | 55.0 |

Example 18

1-{2-[4-(2-amino-5-chloro-3-pyridinyl)phenoxy]-5-pyrimidinyl}-3-[2-(methylsulfonyl)-5-(trifluoromethyl)phenyl]urea p-Toluenesulfonate (Crystal F)

The compound (10 mg) produced in Example 9 was added with and dissolved in 60 μL of 50% hydrated dioxane at 60 to 80° C. This solution was stirred at room temperature overnight, and the resulting solid was collected by means of filtration and then dried, thereby obtaining the present compound having the following physical properties value.
Properties: Crystalline white solid (crystal F)
LC-MS: 579 (M+H)+
$^1$H-NMR (DMSO-$d_6$): δ2.29 (s, 3H), 3.39 (s, 3H), 3.70-4.60 (br, 3H), 7.11 (d, 2H), 7.34 (d, 2H), 7.47 (d, 2H), 7.55 (d, 2H), 7.62-7.72 (m, 1H), 7.79 (d, 1H), 8.08 (d, 1H), 8.13 (d, 1H), 8.61-8.68 (m, 1H), 8.77 (s, 2H), 8.99 (s, 1H), 10.32 (s, 1H)

The powder X-ray diffraction spectrum of the present compound (crystalline white solid) is shown in FIG. 18.
(1) Powder X-Ray Diffraction Spectrum
The foregoing crystal is characterized by, in a powder X-ray diffraction spectrum obtained using a Cu-Kα ray, data of a diffraction angle (2θ) and a relative intensity shown in the following Table 16.

TABLE 16

| Diffraction angle (2θ) | Relative intensity |
|---|---|
| 6.30 | 100.0 |
| 12.44 | 74.0 |
| 13.00 | 29.6 |
| 14.68 | 37.5 |
| 15.61 | 67.2 |
| 17.79 | 84.4 |
| 18.62 | 86.6 |
| 21.54 | 44.8 |
| 23.82 | 37.3 |

Experimental Examples of Compound Characteristics

Compound Characteristics Experiment 1: Test Regarding Solubility

About 5 mg of the present compound was weighed in a test tube, a stirrer and 5 mL of an artificial intestinal juice (FaSSIF; Reference 1: *Pharmaceutical Research*, Vol. 20, pp. 1674-1680, 2003, and Reference 2: *Biological & Pharmaceutical Bulletin*, Vol. 34, pp. 401-407, 2011) were added in the test tube, and the test tube was then hermetically sealed. The test tube was placed in a solubility test apparatus (Gilson, Quad-Z 215), and stirring was performed at 37° C. and 700 rpm. A part of the liquid in the test tube was collected after lapsing 0.25, 0.5, 1, 3, 6, and 24 hours, respectively. The collected liquid was filtered with a filter, and the filtrate was diluted to 2-fold with acetonitrile. The diluted liquid was centrifuged at 3,000 rpm for 5 minutes. A supernatant after centrifugation was used as a sample solution and calculated for solubility by means of high-performance liquid chromatography.

High-Performance Liquid Chromatography Measurement Conditions

Case of 1-{2-[4-(2-amino-5-chloro-3-pyridinyl)phenoxy]-5-pyrimidinyl}-3-[2-(methylsulfonyl)-5-(trifluoromethyl)phenyl]urea (Compound (I)) and Its Acid-Addition Salts (1)
Apparatus: Agilent HPLC 1100 Series
Column: Waters Xbridge C18 (4.6 mm in inside diameter× 50 mm, 3.5 μm)
Column temperature: 40° C.
Mobile phase components: 20 mM Potassium dihydrogenphosphate (pH 3.0)/Acetonitrile (0 min: 55/45, 8 min: 20/80)
UV: 308 nm
Flow rate: 1.0 mL/min
Sample rack temperature: 20° C.
Sample injection amount: 40 μL
Measurement time: 8 min
Retention time: 3.3 min
(2)
Apparatus: HITACHI HPLC La Chrom ELITE
Column: Waters Xbridge C18 (4.6 mm in inside diameter× 50 mm, 3.5 m)
Column temperature: 40° C.
Mobile phase components: 20 mM Potassium dihydrogenphosphate (pH 3.0)/Acetonitrile (0 min: 55/45, 8 min: 20/80)
UV: 308 nm
Flow rate: 1.0 mL/min
Sample rack temperature: 20° C.

Sample injection amount: 10 μL
Measurement time: 8 min
Retention time: 4.3 min

As a result, for example, the solubility of the foregoing Compound (I) and the solubility of its acid-addition salts after lapsing 0.25 hours are shown below. For example, the solubility as the p-toluenesulfonate was 96 μg/mL (corresponding to the solubility of 74 μg/mL per Compound (I) as a free base), and the solubility as the methanesulfonate was 55 μg/mL (corresponding to the solubility of 47 μg/mL per Compound (I) as a free base). Meanwhile, the solubility of the foregoing Compound (I) was 7 μg/mL.

Case of 1-{2-[4-(2-amino-5-fluoropyridin-3-yl)phenoxy]pyrimidin-5-yl}-3-[2-(pyridin-3-yl)-5-(trifluoromethyl)phenyl]urea (Compound (II)) and Its Acid-Addition Salts (1)
Apparatus: HITACHI HPLC La Chrom ELITE
Column: Waters Xbridge Shield RP-18 (4.6 mm in inside diameter×50 mm, 3.5 μm)
Column temperature: 40° C.
Mobile phase components: 20 mM Potassium dihydrogenphosphate (pH 3.0)/Acetonitrile (0 min: 75/25, 10 min: 20/80, 10.1 min: 75/25, 15 min: 75/25)
UV: 312 nm
Flow rate: 1.0 mL/min
Sample rack temperature: 25° C.
Sample injection amount: 5 μL
Measurement time: 10 min
Retention time: 5.9 min
(2)
Apparatus: Agilent HPLC 1100 Series
Column: Waters Xbridge Shield RP-18 (4.6 mm in inside diameter×50 mm, 3.5 μm)
Column temperature: 40° C.
Mobile phase components: 20 mM Potassium dihydrogenphosphate (pH 3.0)/Acetonitrile (0 min: 75/25, 10 min: 20/80, 10.1 min: 75/25, 15 min: 75/25)
UV: 312 nm
Flow rate: 1.0 mL/min
Sample rack temperature: 20° C.
Sample injection amount: 5 μL
Measurement time: 10 min
Retention time: 5.6 min As a result, for example, the solubility of the foregoing Compound (II) and the solubility of its acid-addition salts after lapsing 0.25 hours are shown below. For example, the solubility as the di(p-toluenesulfonate) was 99 μg/mL (corresponding to the solubility of 61 μg/mL per Compound (II) as a free base), and the solubility as the dibenzenesulfonate was 81 μg/mL (corresponding to the solubility of 52 μg/mL per Compound (II) as a free base). Meanwhile, the solubility of the foregoing Compound (II) was 4 μg/mL.

Case of 1-(2-(1H-pyrazol-1-yl)-5-(trifluoromethyl)phenyl)-3-(2-(4-(2-amino-5-chloropyridin-3-yl)phenoxy)pyrimidin-5-yl)urea (Compound (III)) and Its Acid-Addition Salts Apparatus: Agilent HPLC 1100 Series
Column: Waters Xbridge Shield RP-18 (4.6 mm in inside diameter×50 mm, 3.5 μm)
Column temperature: 25° C.
Mobile phase components: 20 mM Potassium dihydrogenphosphate (pH 3.0)/Acetonitrile (0 min: 52/48, 10 min: 20/80, 10.1 min: 52/48, 15 min: 52/48)
UV: 304 nm
Flow rate: 1.0 mL/min
Sample rack temperature: 25° C.
Sample injection amount: 20 μL
Measurement time: 10 min
Retention time: 4.5 min As a result, for example, the solubility of the foregoing Compound (III) and the solubility of its acid-addition salts after lapsing 0.25 hours are shown below. For example, the solubility as the p-toluenesulfonate was 55 μg/mL (corresponding to the solubility of 42 μg/mL per Compound (III) as a free base), and the solubility as the methanesulfonate was 53 μg/mL (corresponding to the solubility of 45 μg/mL per Compound (III) as a free base). Meanwhile, the solubility of the foregoing Compound (II) was 26 μg/mL.

Compound Characteristics Experiment 2:
Experiment Regarding Pharmacokinetics

A suspension of each of the present compounds and free bases thereof (Compound (I), Compound (II), and Compound (III)) was prepared. The suspension was prepared in a content of 0.2 mg/mL with a 0.5% methyl cellulose aqueous solution. The present compound was prepared in a content of 0.2 mg/mL as converted into the corresponding free base. Each of the suspensions was administered by gavage through a probe into the stomach of a monkey (male crab-eating macaque) which had been fasted in advance from the day before the administration. After lapsing 0.25, 0.5, 1, 2, 4, 6, 8, and 24 hours, respectively after administration of the suspension (drug solution), 1 mL of blood was collected from a cephalic vein with a heparinized syringe. The collected blood was centrifuged at 12,000 rpm for 3 minutes, thereby fractionating a plasma.
[Preparation and Analysis of Analytical Sample]

To 10 μL of the plasma, 200 μl of acetonitrile/ethanol (7/3, v/v) containing an internal standard substance (a deuterated body of the free base corresponding to the present compound) was added and stirred. The mixture was centrifuged at 15,000 rpm at room temperature for 2 minutes. A supernatant was diluted to 2-fold with ultrapure water and then analyzed by means of LC/MC/MS.

The analysis by LC/MS/MS was performed under the following conditions.
[LC/MS/MS Conditions]
Analytical instrument: API-4000 (manufactured by Applied Biosystems)
Analytical column: CAPCELL PAK CR18 (2.0 mm I.D.×50 mm, 5 m)
Flow rate: 0.4 mL/min
Mobile phase components: 10 mM Ammonium acetate/Acetonitrile (0 min: 55/45, 0.50 min: 55/45, 1.01 min: 10/90, 2.00 min: 10/90, 2.01 min: 55/45, 3.99 min: 55/45)
Scan type: MRM (multiple reaction monitoring)
Polarity: Positive As a result, the present compounds were excellent in pharmacokinetics relative to the corresponding free bases, respectively.

Compound Characteristics Experiment 3:
Experiment Regarding Drug Interaction 319.92 μL of ultrapure water, 30 μL of a 4/3 mol/L phosphate buffer solution (pH 7.4), 0.08 μL of 500 mmol/L EDTA.2Na (ethylenediaminetetraacetic acid dihydrogen disodium), and 2 µL of 20 mg/mL human liver microsome were mixed to prepare a reaction mixture. The reaction mixture was incubated for 5 minutes on a water bath at 37° C., and 4 µL of a 1 mmol/L test substance preparation was then added, followed by stirring. Furthermore, the reaction mixture was incubated at 37° C. for 5 minutes, and 40 µL of 20 mmol/L NADPH (reduced nicotinamide adenine dinucleotide phosphate) was then added, followed by stirring. The reaction mixture was incubated at 37° C. for 30 minutes, and 4 µL of a 15 mmol/L testosterone preparation was then added, followed by stirred. The reaction mixture was incubated at 37° C. for 5 minutes, and 100 µL of the reaction mixture was then collected and added to acetonitrile containing an internal standard substance ($d_7$-6β-hydroxytestosterone), and the contents were stirred, thereby terminating the reaction. A sample obtained by this method is a test substance-added sample. Meanwhile, a sample obtained under a condition under which in the above-described method, only acetonitrile/dimethyl sulfoxide (9/1, v/v) that is a preparation medium of the test substance was added in place of the test substance is a control sample. The whole amounts of the respective samples were individually centrifuged at 1,500 rpm for 5 minutes using a filter plate (MultiScreen (registered trademark) Solvinert Filter Plates, 0.45 µm Low-Binding Hydrophilic PTFE). The centrifuged samples were each filtered with a filter, and the filtrate was diluted to 2-fold with ultrapure water and then provided for analysis. The analysis by LC/MS/MS was performed under the following conditions.

[LC/MS/MS Conditions]

Analytical instrument: API-4000 (manufactured by Applied Biosystems)

Analytical column: Shim-pack XR-ODSII, 2.2 µm, 150 mm×2 mm I.D.

Column temperature: 40° C.

Mobile phase: 0.1% Formic acid/Acetonitrile (50/50)

Flow rate: 0.3 mL/min

Scan type: MRM (multiple reaction monitoring)

Polarity: Positive

[Data Analysis Method]

Using a peak area ratio of a testosterone metabolite (6β-hydroxytestosterone) {(peak area of testosterone metabolite)/(peak area of internal standard substance)} in the test substance-added sample and a peak ratio of a testosterone metabolite (6β-hydroxytestosterone) {(peak area of testosterone metabolite)/(peak area of internal standard substance)} in the control sample, an inhibition rate (%) was calculated according to the following Equation 1.

Inhibition rate={(Peak area ratio of testosterone metabolite in the test substance-added sample)/ (Peak area ratio of testosterone metabolite in the control sample)}×100(%)    [Eq. 1]

As a result, even when the concentration of the present compound was 10 µM, its inhibition rate was about 21 to 34%, and thus, it was noted that the drug interaction of the present compound was extremely weak. On the other hand, the inhibition rate of Example 85-226 described in Patent Document 2 was 58% (10 µM), and its 50% inhibition concentration ($IC_{50}$) was 10 µM or less, and thus, the compound was high in the drug interaction.

Pharmacological Experiment Examples

Pharmacological Experiment Example 1: Measurement of TrkA Kinase-Inhibiting Activity Using Human TrkA-Expressing Cells TrkA kinase-inhibiting activity in cell systems was measured using CHO-K1 cells expressing human TrkA and NFAT-bla (CellSenser™ TrkA-NFAT-bla CHO-K1 cells, Invitrogen).

On the day before the assay, CellSenser™ TrkA-NFAT-bla CHO-K1 cells were suspended in an assay medium (Opti-MEM1 Reduced Serum Medium (Invitrogen) containing 0.5% dialysed fetal bovine serum (Invitrogen), 0.1 mM nonessential amino acids (Invitrogen), 1 mM sodium pyruvate (Invitrogen), and antibiotics (100 U/mL penicillin and 100 µg/mL streptomycin (Invitrogen))) and plated at a density of $2.4 \times 10^4$ cells/40 µL/well in a 96-well clear bottom plate (Corning, Catalogue No.: 3882). In addition, in some wells were added only the assay medium at 40 µL/well (Cell-free). On the day of the assay, 10 mM of the present compound (DMSO solution) was distributed in a 96-well plate (Costar, Catalogue No.: 3363) and serially diluted with DMSO, thereby preparing serial solutons with the geometrical ratio of 3. The serial dilutions were diluted with the assay medium to 100-fold, thereby preparing a solution of the present compound with a 10-fold concentration (DMSO concentration: 1%). To the plate where cells were plated was added the present compound at 5 µL/well, and the plate was incubated in a $CO_2$ incubator with 5% $CO_2$ and 95% air at 37° C. for 30 minutes. For a control and a blank, the assay medium containing 1% DMSO was added at 5 µL/well in place of the solution of the present compound. Subsequently, the assay medium containing NGF (Mouse 2.5s, Natural, Invitrogen) was added to the plate at 5 µL/well (final concentration of NGF: 50 ng/ml), and the plate was incubated in a $CO_2$ incubator with 5% $CO_2$ and 95% air at 37° C. for 5 hours. For the blank group, the assay medium was added in place of the NGF at 5 µL/well. A reporter assay detection reagent was added at 10 µL/well to the plate, followed by incubation in the dark at room temperature for 120 minutes. The reporter assay detection reagent was prepared from LiveBLAzer™-FRET B/G Loading Kit (Invitrogen). Using Analyst GT (Molecular Devices Japan, K.K.), the wells were each irradiated with excitation light at 405 nm, and the fluorescence intensities at 460 nm and 530 nm were measured. The time resolved fluorescence resonance energy transfer (TR-FRET) ratio of each of the wells was calculated according to the following Equation 2.

TR-FRET ratio=$(A_{460X}-A_{460F})/(A_{530X}-A_{530F})$    [Eq. 2]

$A_{460X}$: Fluorescence intensity at 460 nm of the present compound, the control, or the blank $A_{460F}$: Fluorescence intensity at 460 nm of the Cell-free $A_{530X}$: Fluorescence intensity at 530 nm of the present compound, the control, or the blank $A_{530F}$: Fluorescence intensity at 530 nm of the Cell-free The TR-FRET inhibition rate (%) of the present compound was calculated according to the following Equation 3.

Inhibition rate (%)=$\{1-(A_X-A_B)/(A_C-A_B)\} \times 100$    [Eq. 3]

$A_X$: TR-FRET ratio at the time of adding the present compound $A_B$: TR-FRET ratio of the blank $A_C$: TR-FRET ratio of the control The IC$_{50}$ value of the present compound was calculated from an inhibition curve based on the inhibition rate of the present compound at respective concentrations.

As a result, it was noted that the TrkA-inhibiting activity (IC$_{50}$ value) of the present compound was less than 1 nM and very strongly inhibited the TrkA.

Pharmacological Experiment Example 2:
Enzyme-Inhibiting Activity Test of KDR

The present compound was dissolved in dimethyl sulfoxide, thereby preparing a 100-fold concentration of the test concentration, 3 μM. The solution was further diluted to 25-fold with an assay buffer (20 mM HEPES, 0.01% Triton X-100, 2 mM DTT, pH 7.5), thereby preparing a solution of the present compound. In a similar manner, a positive control substance solution was prepared with a positive control substance.

A 4-times concentration solution (5 μL) of the present compound adjusted with the assay buffer, 5 μL of a 4-times concentration solution of substrate/ATP/metal (Mg) and 10 μL of a 2-times concentration solution of kinase were mixed in a well of a polypropylene-made 384-well plate and allowed to react at room temperature for one hour. The reaction was terminated by adding 60 μL of a Termination Buffer (QuickScout Screening Assist MSA; Carna Biosciences). The substrate peptide and the phosphorylated peptide in the reaction solution were separated and quantified. The kinase reaction was assessed from the product ratio (P/(P+S)) calculated from the height (S) of the peak of the substrate peptide and the height (P) of the peak of the phosphorylated peptide. The following Table 17 indicates a substrate, a substrate concentration, an ATP concentration, and a positive control substance used in the KDR enzyme inhibition activity test.

TABLE 17

| Kinase | Substrate Name | Concentration (nM) | ATP concentration (μM) | Positive control substance |
|---|---|---|---|---|
| KDR | CSKtide | 1,000 | 75 | Staurosporine |

The inhibition rate was calculated from the average signal of the test wells of the present compound while defining the average signal of control wells each containing all reaction components as 0% inhibition and defining the average signal of background wells (without addition of the enzyme) as 100% inhibition, respectively. As a result, the present compound at a concentration of 3 μM had an inhibition rate of KDR of 0 to 18%.

From this result, it was noted that the present compound was very weak in the inhibition of KDR and selectively strongly inhibited the TrkA.

Pharmacological Experiment Example 3: Inhibiting Effect of Rat NGF-Induced Vascular Hyper Permeability TrkA-inhibiting activity of the present compound was evaluated in vivo. The present compound dissolved in a medium was orally administered (adminstered volume: 5 mL/kg) to male CD(SD)IGS rats (7- to 9-week old, Charles River Laboratories Japan, Inc.) shaved on the back. A medium was orally administered (adminstered volume: 5 mL/kg) to the control and normal groups. After 12 or 14 hours of administration, 3 μg/mL of an NGF (Mouse 2.5s, Natural, Invitrogen) solution prepared in 0.1% BSA (Sigma-Aldrich)-containing saline was intracutaneously administered (adminstered volume; 50 μL/site) at 3 sites on the back of animals under halothane anesthesia. For the normal group, 0.1% BSA-containing saline was intracutaneously administered (adminstered volume; 50 μL/site) at 3 sites on the back. Immediately after intracutaneous administration, 1% Evans Blue (Tokyo Chemical Industriy Co., Ltd.) dissolved in saline was administered intravenously from tail (adminstered volume: 3 mL/kg). After 10 minutes of administration, the animals were sacrificed by bleeding due to incision of the abdominal aorta. The sites of intracutaneous administration on the back (3 sites) were excised, and the skin samples were respectively transferred to the wells in a 48-well plate (Asahi Glass Co., Ltd.). Formamide (0.8 mL/well) was added to the plate, and the plate was sealed and incubated overnight at 60° C. The formamide extraction solution (200 μL) was transferred to a 96-well plate, and the absorbance (wavelength: 620 nm) of Evans Blue extracted in formamide was measured on an absorbance microplate reader (SpectraMAX 190, Molecular Devices Japan, K.K.). Standard samples of Evans Blue dissolved in formamide (0, 0.78, 1.56, 3.13, 6.25, 12.5, 25, and 50 μg/mL) were measured at the same time for the absorbance (wavelength: 620 nm), thereby preparing a calibration curve. Based on the calibration curve and the absorbances of the respective samples, the concentrations of Evans Blue in each sample was calculated. The concentrations of Evans Blue for three skin samples collected from one aminal were averaged to obtain the value for the animal. The rate of inhibition for rat NGF-induced vascular hyper permeability of the present compound was calculated according to the following Equation 4.

$$\text{Inhibition rate (\%)} = \{1 - (A_X - A_N)/(A_C - A_N)\} \times 100 \quad \text{[Eq. 4]}$$

$A_X$: Concentration of Evans Blue of the present compound (an average value of 3 samples from one animal)

$A_N$: Concentration of Evans Blue of the normal group (an average value of 3 samples from one animal)

$A_C$: Concentration of Evans Blue of the control group (an average value of 3 samples from one animal)

As a result, it was noted that the present compound (administered in an amount of 1 mg/kg as converted into the corresponding free base (Compound (I), Compound (II), or Compound (III)) strongly inhibited rat NGF-induced vascular hyper permeability even after lapsing a long period of time. For example, the hydrochloride of Compound (I) had an inhibition rate of about 100% (14 hours before administration); the di(p-toluenesulfonate) of Compound (II) had an inhibition rate of about 78% (12 hours before administration); and the methanesulfonate of Compound (III) had an inhibition rate of about 97% (14 hours before administration). On the other hand, Example 85-90 and Example 85-146 described in Patent Document 2 had an inhibition rate of rat NGF-induced vascular hyper permeability of 54% (1 mg/kg; 12 hours before administration) and 26% (1 mg/kg; 14 hours before administration), respectively.

Pharmacological Experiment Example 4: Analgesic Effect on Sodium Monoiodoacetate-Induced Model Rats Using model rats induced with sodium monoiodoacetate (hereinafter abbreviated as "MIA") (Sigma-Aldrich Japan), the present compound was evaluated for the analgesic effect thereof.

(1) Preparation of MIA-Induced Model Rats

Under isoflurane anaesthesia, rats were shaved on around knees of right hind limbs, and 25 µL of a 120 mg/mL MIA solution was administered into the right hind limb knee joint using a syringe (BD Lo-Dose, Beckton Dickinson Japan) with a 29 G needle. To a normal control group, 25 µL of saline was administered.

(2) Group Organization and Grouping

The groups included were a normal control group, a disease control group, a present compound-administered group, and a tramadol-administered group or morphine-administered group. Other than the normal control group, rats were grouped so that the right hind limb weight load ratio (the measurement method will be described later) of model rats 14 days after induction with MIA prepared according to the method as described in the above (1) was equivalent between all groups.

(3) Administration of Present Compound, Tramadol, or Morphine

The present compound was dissolved in Wellsolve (Celeste Corporation) to prepare a solution of 0.1, 0.3, or 1 mg/mL (concentration as converted into corresponding free bases, Compound (I), Compound (II), or Compound (III), respectively). The prepared 0.1, 0.3, or 1 mg/mL solution was diluted to 5-fold with distilled water, thereby preparing a 0.02, 0.06, or 0.2 mg/mL solution (final concentration of Wellsolve: 20%). The tramadol that is the positive control drug was dissolved in saline to prepare a 2 mg/mL solution. Alternatively, the morphine that is the positive control drug was dissolved in saline to prepare a 0.6 mg/mL solution. From day 14 to day 23 after induction with MIA, a solution of the present compound (0.1, 0.3, or 1 mg/kg) (concentration as converted into corresponding free bases, Compound (I), Compound (II), or Compound (III), respectively) was repeatedly orally administered to the present compound group twice a day over 10 days. On day 24 after induction with MIA, the present compound solution was further orally administered 3 hours before the measurement of the right hind limb weight load ratio, and saline was subcutaneously administered one hour before the measurement. The tramadol group or the morphine group was repeatedly orally administered with 20% Wellsolve twice a day over 10 days from day 14 to day 23 after induction with MIA. On day 24 after induction with MIA, 20% Wellsolve was further orally administered 3 hours before the measurement of the right hind limb weight load ratio, and a tramadol solution (10 mg/kg) or a morphine solution (3 mg/kg) was subcutaneously administered one hour before the measurement. In addition, the normal control group and the disease control group were repeatedly orally administered with 20% Wellsolve twice a day over 10 days from day 14 to day 23 after induction with MIA. On day 24 after induction with MIA, 20% Wellsolve was further orally administered 3 hours before the measurement of the right hind limb weight load ratio, and saline was subcutaneously administered one hour before the measurement.

(4) Measurement of Right Hind Limb Weight Load Ratio

The weight load on right and left hind limbs was measured with the Linton Incapacitance Tester (MJS Technology INC., UK). Namely, a rat was transferred into an exclusive cage on the Linton Incapacitance Tester and adjusted so that right and left hind limbs were respectively on each of two pairs of gravimetric sensors. After confirming that the rat was balanced on left and right and forward and back, the weight load of left and right hind limbs was respectively measured for 3 seconds. The measurement of weight load was repeated 3 times per rat. In order to obtain stable measured values, rats were conditioned in the exclusive cage for 20 minutes or longer per day over 5 or more days between the day of induction with MIA and day 14 after induction. Further, rats were also conditioned in the cage immediately before the measurement of weight load for about 10 minutes. The weight load of right and left hind limbs was measured before grouping on day 14 after induction with MIA and day 24 after induction for the normal control group, the disease control group, the present compound-administered group (3 hours after administration), the tramadol-administered group (one hour after administration), and the morphine-administered group (one hour after administration). Based on the average values of right and left hind limb weight loads, the right hind limb weight load ratio with respect to the weight load of both hind limbs was calculated according to the following Equation 5. The measurement was carried out in a blind manner. A percent improvement of the present compound was calculated based on the right hind limb weight load ratio of each group at day 24 after induction with MIA according to the following Equation 6, thereby evaluating analgesic effect of the present compound.

$$\text{Right hind limb weight load ratio } B\ (\%) = \{A_R/(A_R + A_L) \times 100\} \quad [\text{Eq. 5}]$$

$A_R$: Weight load of right hind limb (average value of three measurements per rat)

$A_L$: Weight load of left hind limb (average value of three measurements per rat)

$$\text{Percent improvement of present compound } (\%) = \{1 - (B_T - B_C)/(B_N - B_C)\} \times 100 \quad [\text{Eq. 6}]$$

$B_C$: Average value of the normal control group
$B_N$: Average value of the disease control group
$B_T$: Average value of the present compound group.

As a result, the present compound had a percent improvement equivalent to or higher than that of tramadol (percent improvement: 43%) and morphine (percent improvement: 54%), each of which is commonly used as an analgesic agent. For example, the hydrochloride of Compound (I) had a percent improvement of about 54% (positive control drug: morphine); the di(p-toluenesulfonate) of Compound (II) had a percent improvement of about 53% (positive control drug: morphine); and the methanesulfonate of Compound (III) had a percent improvement of about 61% (positive control drug: tramadol). Accordingly, it was noted that the present compound had an analgesic effect equivalent to or higher than that of tramadol and morphine.

Pharmacological Experiment Example 5:
Anti-Tumor Effect on Human Colon Cancer Cell Line KM12

Using KM12 (ATCC, Inc., Catalogue No. RBC0805) that is a human colon cancer cell line, the anti-tumor effect of the present compound was evaluated. KM12 was plated in DMEM (Life Technologies Corporation, Catalogue No. 11965) containing a 10 volume % inactivated fetal bovine serum (FBS) and a 1 volume % penicillin-streptomycin liquid (Life Technologies Corporation) and subcultured. On the day before the treatment with the present compound, the KM12 was floated using 0.25% Trysin-EDTA, and the KM12 was recovered into a centrifugal tube from the dish. The KM12 was centrifuged at 180 g at room temperature for 3 minutes, and a cell sediment was then suspended in 10 mL of a DMEM medium. A part of the KM12 suspension was collected, the number of cells thereof was counted, and the KM12 was then suspended in a cell density of 5×10⁴ cells/mL in a DMEM medium, thereby preparing a cell suspension. In a 96-well tissue culture plate (Asahi Glass Co., Ltd.), 100 µL/well of the KM12 suspension was plated, and the plate was allowed to stand for 16 hours under conditions at 37° C. in 5% $CO_2$ and 95% air. On the day of the treatment with the present compound, 10 mmol/L of the present compound (DMSO solution) was serially diluted with DMSO, thereby preparing solutions of the present compound having a concentration of 0.03, 0.1, 0.3, 1, 3, 10, 30, and 100 µmol/L, respectively. Furthermore, these DMSO solutions were diluted to 100-fold with the medium, thereby preparing media containing the present compound having a concentration of 0.3, 1, 3, 10, 30, 100, 300, and 1,000 nmol/L, respectively. The medium within the 96-well tissue culture plate in which the KM12 was subjected to static culture for 16 hours was removed by means of decantation. Thereafter, each of the wells was added with the DMEM medium and the above-prepared medium containing the present compound in an amount of 90 and 10 µL/well, respectively (the final concentration of the present compound became 0.03, 0.1, 0.3, 1, 3, 10, 30, and 100 nmol/L). Thereafter, the plate was subjected to static culture for 72 hours under conditions at 37° C. in 5% $CO_2$ and 95% air. After completion of the static culture, using a CellTiter-Glo Luminescent Cell Viability Assay kit (Promega, G7571), a luminescence signal (relative luminescence unit, RLU) of each well was measured by a micro plate reader. An average value of RLU of the three wells of the medium group (group in which the DMSO solution having a concentration of the present compound of zero (0) was treated) was calculated, and a KM12 proliferation rate in each well was calculated according to the following Equation 7.

KM12 proliferation rate (%)=(RLU of each well)÷(Average value of RLU of the medium group)×100 [Eq. 7]

Next, with respect to the group treated with the present compound, a KM12 proliferation inhibition rate in each well was calculated according to the following Equation 8.

KM12 proliferation inhibition rate (%)=100−(KM12 proliferation rate (%)) [Eq. 8]

As a result, it was noted that the present compound strongly inhibited the proliferation of KM12.

Formulation Examples

Formulation Example 1

The following components were mixed according to a conventional method, compressed to tablets, thereby obtaining 10,000 tablets containing 10 mg of the active ingredient per tablet.
1-{2-[4-(2-amino-5-chloro-3-pyridinyl)phenoxy]-5-pyrimidinyl}-3-[2-(methylsulfonyl)-5-(trifluoromethyl)phenyl]urea hydrochloride: 100 g
Calcium carboxymethyl cellulose (disintegrating agent): 20 g
Magnesium stearate (lubricant): 10 g
Microcrystalline cellulose: 870 g Formulation Example 2

The following components were mixed according to a conventional method, filtered through a dust filter, distributed to ampoules at 5 ml, and thermally sterilized in an autoclave, thereby obtaining 10,000 ampoules containing 20 mg of the active ingredient per ampoule.
1-{2-[4-(2-amino-5-chloro-3-pyridinyl)phenoxy]-5-pyrimidinyl)}-3-[2-(methylsulfonyl)-5-(trifluoromethyl)phenyl]urea hydrochloride: 200 g
Mannitol: 20 g
Distilled water: 50 L

INDUSTRIAL APPLICABILITY

The present compound exhibits Trk-inhibiting activity and thus is useful as a prophylactic and/or therapeutic agent for Trk-related diseases, such as pain, pruritus, lower urinary tract dysfunction, asthma, allergic rhinitis, inflammatory bowel disease, Chagas disease, cancer, etc.

The invention claimed is:
1. 1-{2-[4-(2-amino-5-chloro-3-pyridinyl)phenoxy]-5-pyrimidinyl}-3-[2-(methylsulfonyl)-5-(trifluoromethyl)phenyl]urea p-toluenesulfonate.
2. The salt according to claim 1, wherein the salt is a crystal.
3. The salt according to claim 2, having, in a powder X-ray diffraction spectrum, at least two or more peaks at 2θ selected from about 6.35, 7.74, 9.98, 11.08, 11.42, 12.68, 13.22, 14.83, 15.42, 15.98, 16.89, 17.33, 17.86, 18.29, 19.00, 19.46, 20.56, 20.92, 21.47, 22.04, 23.82, and 24.49.
4. 1-{2-[4-(2-amino-5-fluoropyridin-3-yl)phenoxy]pyrimidin-5-yl}-3-[2-(pyridin-3-yl)-5-(trifluoromethyl)phenyl]urea di(p-toluenesulfonate).
5. The salt according to claim 4, wherein the salt is a crystal.
6. The salt according to claim 5, having, in a powder X-ray diffraction spectrum, at least two or more peaks at 2θ selected from about 6.11, 6.29, 7.76, 9.65, 10.18, 12.30, 12.57, 13.23, 13.59, 14.05, 14.85, 15.47, 16.94, 17.98, 18.52, 18.79, 19.32, 20.58, 21.25, 21.55, 22.11, 22.73, 23.20, and 24.36.
7. A pharmaceutical composition comprising the acid-addition salt of claim 1.
8. A pharmaceutical composition comprising the acid-addition salt of claim 4.
9. The composition according to claim 7, which is a Trk inhibitor.
10. The composition according to claim 7, which is a prophylactic and/or therapeutic agent for Trk-related disease.
11. The composition according to claim 10, wherein the Trk-related disease is pain, pruritus, lower urinary tract dysfunction, asthma, allergic rhinitis, inflammatory bowel disease, Chagas disease, or cancer.
12. The composition according to claim 11, wherein the pain is pain of osteoarthritis, cancer pain, chronic low back pain, low back pain of osteoporosis, pain of bone fracture, pain of rheumatoid arthritis, neuropathic pain, postherpetic pain, pain of diabetic neuropathy, fibromyalgia, pain of pancreatitis, pain of interstitial cystitis, pain of endometriosis, pain of irritable bowel syndrome, migraine, postoperative pain, or pain of pulpitis.
13. The composition according to claim 11, wherein the cancer is breast cancer, colon cancer, lung cancer, thyroid cancer, skin cancer, leukemia, tumors of salivary gland, neuroendocrine tumor, lymphoma, cerebral tumor, neuroblastoma, ovarian cancer, pancreatic cancer, mesothelioma, esophageal carcinoma, pulmonary sarcoma, medulloblastoma, glioblastoma, colon cancer, liver cancer, retinoblastoma, kidney cancer, bladder cancer, osteosarcoma, stomach cancer, uterine cancer, vulvar cancer, small intestinal cancer, prostate cancer, bile duct cancer, ureterocele, adrenal cortical carcinoma, or head and neck cancer.

\* \* \* \* \*